United States Patent
Bailey et al.

(10) Patent No.: US 10,532,130 B2
(45) Date of Patent: Jan. 14, 2020

(54) SOFT TISSUE MIMETICS AND THERMOPLASTIC ELASTOMER HYDROGELS

(71) Applicant: Colorado State University Research Foundation, Fort Collins, CO (US)

(72) Inventors: Travis S. Bailey, Fort Collins, CO (US); Kristine Fischenich, Fort Collins, CO (US); Jackson T. Lewis, Fort Collins, CO (US); Tammy Haut Donahue, Fort Collins, CO (US); Chen Guo, Newark, DE (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 15/539,475

(22) PCT Filed: Dec. 5, 2016

(86) PCT No.: PCT/US2016/064921
§ 371 (c)(1),
(2) Date: Jun. 23, 2017

(87) PCT Pub. No.: WO2017/096352
PCT Pub. Date: Jun. 8, 2017

(65) Prior Publication Data
US 2019/0151511 A1 May 23, 2019

Related U.S. Application Data

(60) Provisional application No. 62/263,025, filed on Dec. 4, 2015, provisional application No. 62/281,497, filed (Continued)

(51) Int. Cl.
*C08J 3/075* (2006.01)
*A61L 27/52* (2006.01)
(Continued)

(52) U.S. Cl.
CPC .............. *A61L 27/52* (2013.01); *A61L 27/26* (2013.01); *B01D 69/02* (2013.01); *B01D 71/80* (2013.01);
(Continued)

(58) Field of Classification Search
CPC ..... C08J 3/075; C08L 53/005; C08L 2201/54; C08L 71/02
See application file for complete search history.

(56) References Cited

U.S. PATENT DOCUMENTS

| 2002/0159982 A1 | 10/2002 | Bonassar et al. |
| 2003/0232895 A1 | 12/2003 | Omidian et al. |

(Continued)

FOREIGN PATENT DOCUMENTS

| WO | WO 2015/038577 A1 | 3/2015 |
| WO | WO 2017/096352 A1 | 6/2017 |
| WO | WO 2017/096367 A1 | 6/2017 |

OTHER PUBLICATIONS

Guo C, Bailey TS. Highly distensible nanostrucured elastic hydrogels from AB diblock and ABA triblock copolymer melt blends. Soft Matter (online). Aug. 16, 2010 (retrieved on Jan. 26, 2017 from the internet), vol. 6, issue 19, pp. 4807-4818.
(Continued)

*Primary Examiner* — Mark S Kaucher
(74) *Attorney, Agent, or Firm* — Polsinelli PC

(57) ABSTRACT

Provided herein is a soft tissue mimetic formed from a block copolymer hydrogel and methods of making such. The hydrogel comprises a glass formed from a dry blend of polystyrene-poly(ethylene oxide) diblock copolymer (SO) and polystyrene-poly(ethylene oxide)-polystyrene triblock copolymer (SOS) in a molar ratio from between 95:5 and 1:99 SO/SOS and a liquid medium at a concentration between about 32:1 and about 2:1 liquid medium/SO-SOS
(Continued)

by weight. The soft tissue mimetic has a fatigue resistance to at least 500,000 compression cycles.

33 Claims, 57 Drawing Sheets

Related U.S. Application Data on Jan. 21, 2016, provisional application No. 62/306,340, filed on Mar. 10, 2016.

(51) Int. Cl.
    *B01D 69/02*     (2006.01)
    *B01D 71/80*     (2006.01)
    *B01J 13/00*     (2006.01)
    *C08L 53/00*     (2006.01)
    *H01M 2/16*     (2006.01)
    *A61L 27/26*     (2006.01)
    *C08G 81/02*     (2006.01)

(52) U.S. Cl.
    CPC ........ *B01J 13/0052* (2013.01); *C08G 81/025* (2013.01); *C08J 3/075* (2013.01); *C08L 53/00* (2013.01); *H01M 2/1653* (2013.01); *B01J 2219/00051* (2013.01); *B01J 2219/00162* (2013.01); *C08J 2325/06* (2013.01); *C08J 2353/00* (2013.01); *C08J 2371/02* (2013.01); *C08L 2203/02* (2013.01); *C08L 2207/04* (2013.01)

(56) References Cited

U.S. PATENT DOCUMENTS

| | | |
|---|---|---|
| 2003/0236513 A1 | 12/2003 | Schwarz et al. |
| 2004/0101518 A1 | 5/2004 | Vacanti et al. |
| 2008/0191200 A1 | 8/2008 | Frisbie et al. |
| 2010/0221614 A1 | 9/2010 | Bertin et al. |
| 2011/0104452 A1 | 5/2011 | Grozea et al. |
| 2015/0110772 A1 | 4/2015 | Scherman et al. |
| 2019/0031835 A1* | 1/2019 | Bailey .................... C08J 3/075 |

OTHER PUBLICATIONS

Guo C, Bailey TS. Tailoring mechanical response through coronal layer overlap in tethered micelle hydrogel networks. Soft Matter (online). Aug. 14, 2015 (retrieved on Jan. 26, 2017 from the internet), vol. 11, issue 37, pp. 7345-7355.
International Search Report and Written Opinion, PCT/US2016/064921, dated Feb. 21, 2017.

* cited by examiner

FIG. 6A
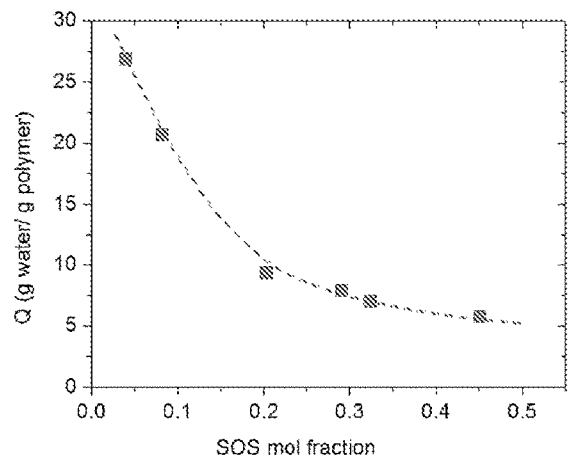
FIG. 6B
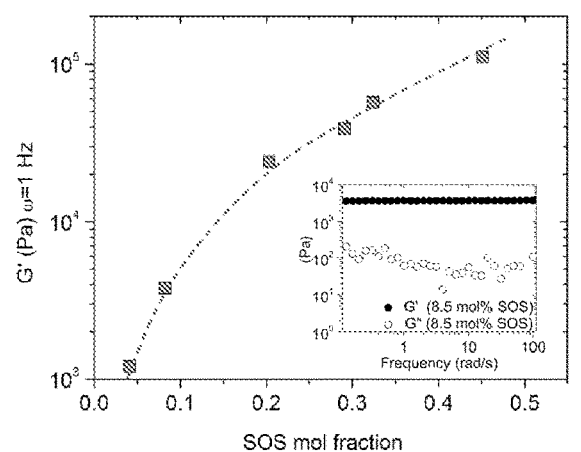
FIG. 6C
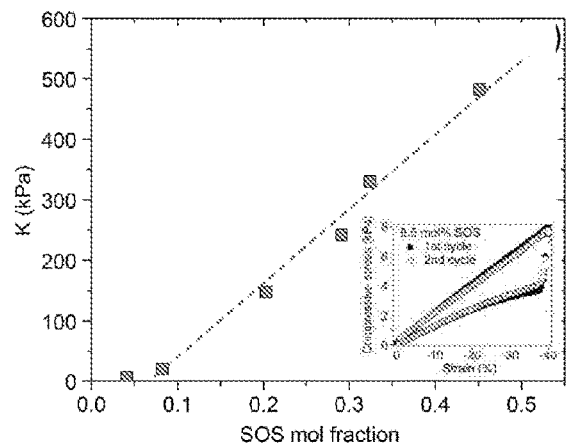
FIG. 6D
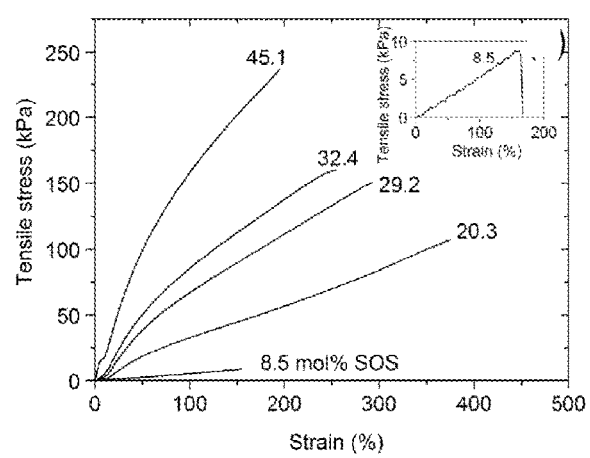
FIG. 6

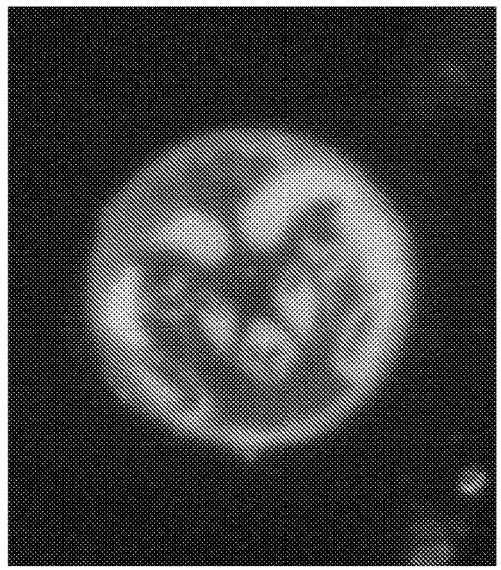
$t_{rinse}$ = 0
FIG. 55A
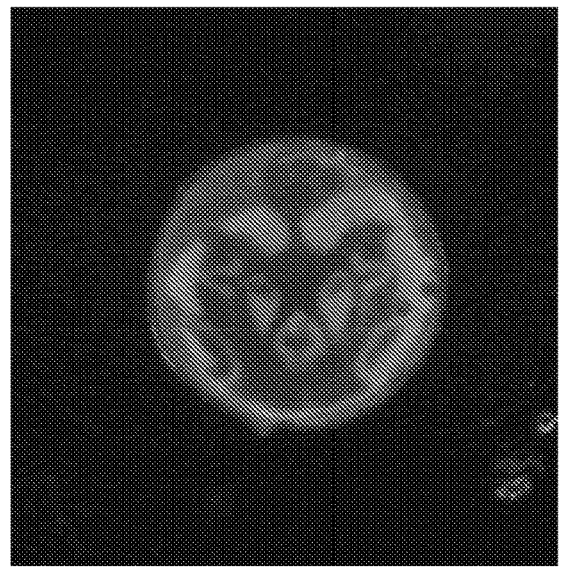
$t_{rinse}$ = 60 hours
FIG. 55B
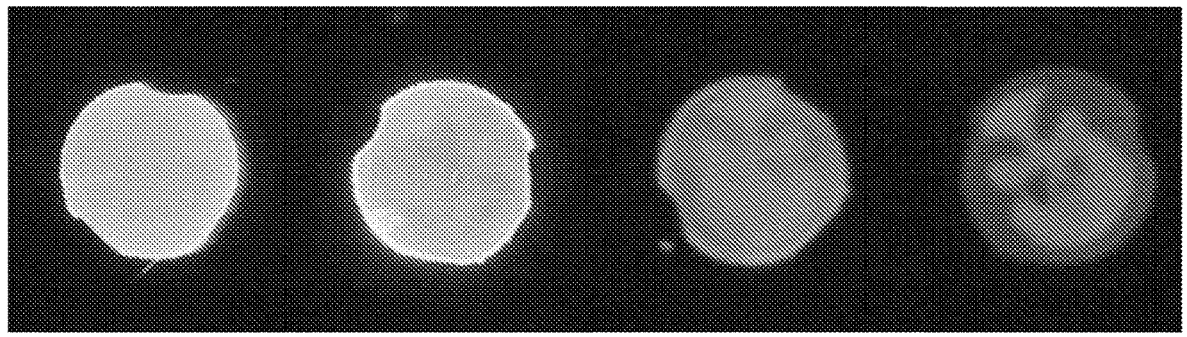
FIG. 56A  FIG. 56B  FIG. 56C  FIG. 56D

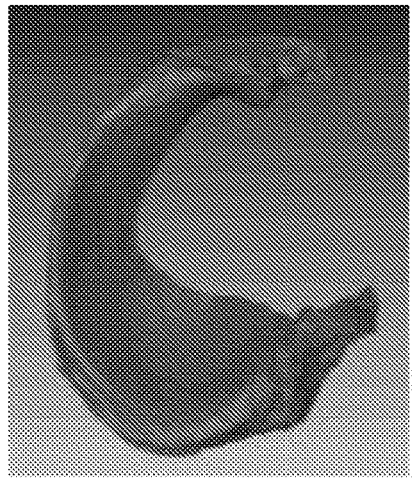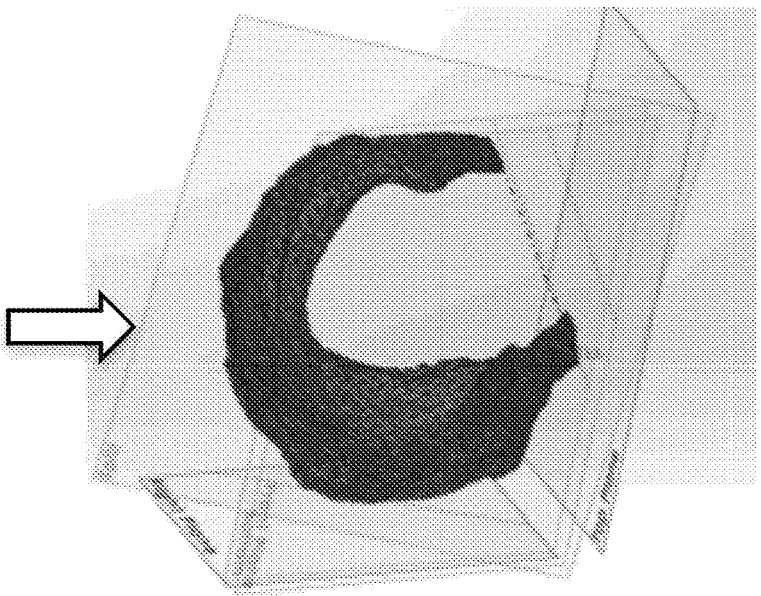
FIG. 58A  FIG. 58B
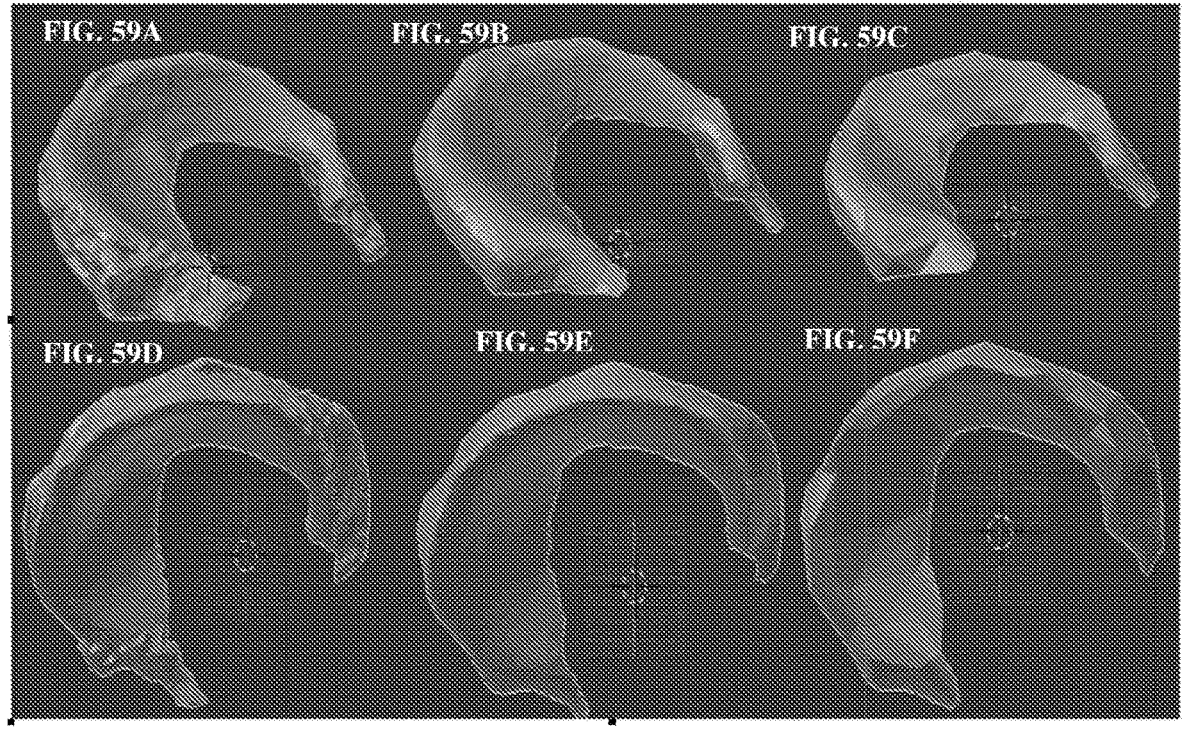
FIG. 59

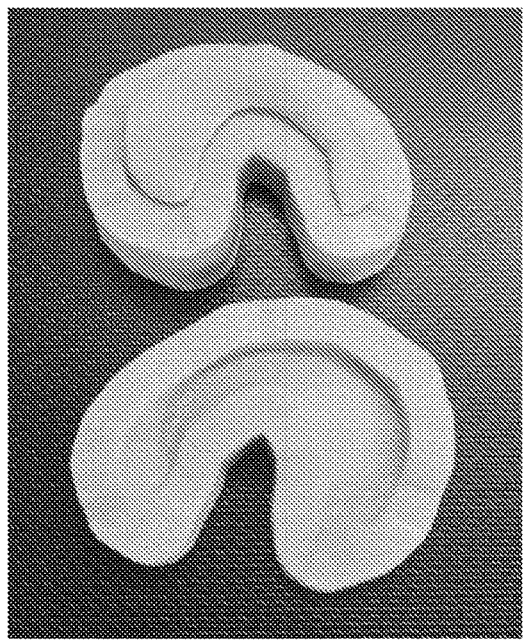 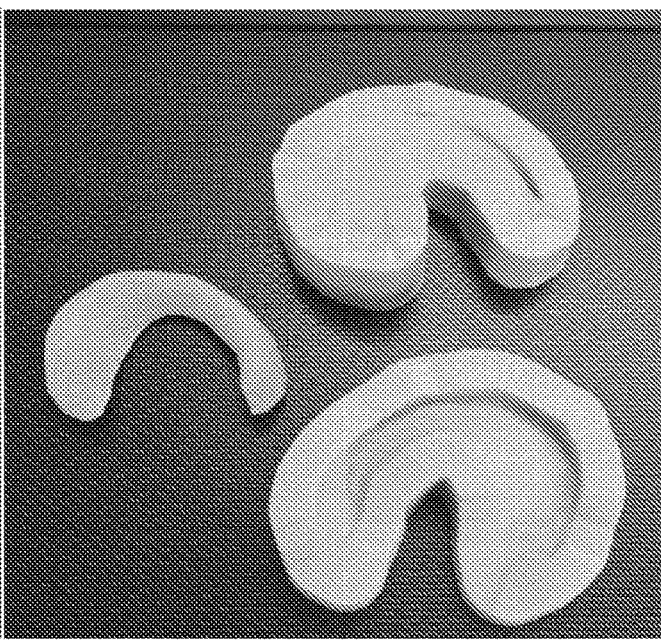
FIG. 60A  FIG. 60B
 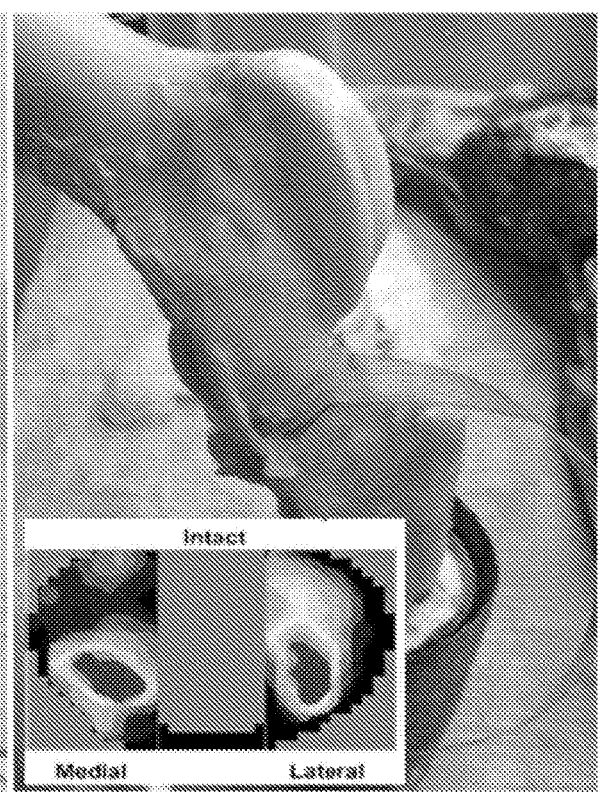
FIG. 61A  FIG. 61B

SOFT TISSUE MIMETICS AND THERMOPLASTIC ELASTOMER HYDROGELS

CROSS-REFERENCE

This application claims the benefit under 35 U.S.C. § 119(e) of U.S. Provisional application Ser. No. 62/263,025 entitled "Mechanically Elastic RTIL Composite Membranes for Efficient Carbon Dioxide Separations from Light Gas Mixtures," filed Dec. 4, 2015; U.S. Provisional application Ser. No. 62/281,497 entitled "Thermoplastic Elastomer Hydrogels," filed Jan. 21, 2016; and U.S. Provisional application Ser. No. 62/306,340 entitled "Thermoplastic Elastomer Hydrogels," filed Mar. 10, 2016, the disclosures of which are herein incorporated by reference in their entireties for all purposes.

GOVERNMENT SUPPORT

This invention was made with government support under Grants CBET1160026 and DMR0645781 awarded by the National Science Foundation; and R21 AR069826 awarded by the National Institutes of Health. The government has certain rights in the invention.

TECHNICAL FIELD

Aspects of the present disclosure relate to copolymer blends. More specifically, the present disclosure relates to soft tissue mimetics using thermoplastic elastomer hydrogels, which have a high water content while maintaining superior fatigue resistance and modulus recovery.

BACKGROUND

About 130,000 anterior cruciate ligament (ACL) reconstructions are performed each year in the U.S. These repairs involve repairing tears in the knee meniscus. The standard treatment is to leave asymptomatic damage alone or perform partial or total meniscectomies (removing damaged meniscal tissue). Both solutions increase the risk of developing osteoarthritis and the eventual need for a total knee replacement. Meniscal allograft research has given mixed results and no long-term data, leaving meniscal allografts as a procedure that few surgeons perform. Nonetheless, healthy joints to have intact and functional menisci to prevent osteoarthritis.

One of the difficulties in creating artificial and tissue-engineered menisci is the complex structure-function relationship of the native tissue. The meniscus is a biphasic tissue composed of interstitial fluid and a matrix composed of predominantly circumferential collagen fibers and glycosaminoglycan-rich proteoglycans. The hierarchical structure and surface network of randomly oriented collagen fibers have a highly aligned circumferential fibers throughout, which enables its mechanical function. This collagen organization transfers compressive loads into tensile hoop stress. These collagen fibers provide the tissue's mechanical anisotropy with the tensile elastic modulus one to two orders of magnitude larger than the compressive elastic modulus.

Conventional hydrogels lack the resistance to fatigue and fracture under continue cyclic loading or extensive compressive strain required for biomedical implants. Mechanical performance in hydrogels ranges from very soft and brittle gels to extremely tough and stiff gels, all of which may be widely applied. Conventional hydrogels, such as highly crosslinked polyvinyl alcohols, have been particularly successful in low-load bearing biomedical applications including drug delivery, wound dressings, and injectable fillers, due to their high water content and biocompatibility. Thus, there exists a need for new hydrogels that can be used to form soft tissue mimetics, such as knee meniscus replacements.

SUMMARY

The claimed soft tissue mimetics achieves both the relaxation behavior consistent with a biphasic material, while also exhibiting the necessary fatigue resistance. The diblock copolymer hydrogels exploit reversible (minimally dissipative) energy absorption mechanisms to achieve exceptional fatigue resistance, long-term mechanical stability, and elastic recovery for soft tissue mimetics, particularly handling repetitive cyclic loading. The exceptional properties of these hydrogels are possible through the nanoscale structure imparted by block copolymer self-assembly in the diblock melt. Without wishing to be bound by theory, this nanostructure consists of trillions of flexibly tethered spherical domains per milligram to efficiently and rapidly distribute stress across the material, similar to native biological soft tissues.

Provided herein is a soft tissue mimetic formed from a block copolymer hydrogel. The hydrogel comprises a glass formed from a dry blend of polystyrene-poly(ethylene oxide) diblock copolymer (SO) and polystyrene-poly(ethylene oxide)-polystyrene triblock copolymer (SOS) in a molar ratio from between 95:5 and 1:99 SO/SOS, and a liquid medium at a concentration between about 32:1 and about 2:1 liquid medium/SO-SOS by weight. The soft tissue mimetic has a fatigue resistance to at least 500,000 compression cycles.

The molar ratio may be between about 80:20 and about 20:80 SO/SOS, such as between about 70:30 and about 20:80 SO/SOS. The soft tissue mimetic may have a content of liquid medium between about 16:1 and about 4:1 liquid medium/SO-SOS by weight. The liquid medium may be chosen from an aqueous medium.

The soft tissue mimetic may further comprise one or more reinforcements selected from polyamide fibers, methacrylate-functionalized polyamide fibers, acrylate-functionalized polyamide fibers, and photo-crosslinked tie lines. The reinforcements may be located circumferentially and radially within the soft tissue mimetic. The soft tissue mimetic may also further comprise one or more suture tabs adapted for implanting the soft tissue mimetic into a patient.

The compression cycles may operate with at least 12% compression at a frequency of about 1 Hz. The compression cycles may operate with at least 50% compression at least every eleventh cycle. The fatigue resistance may be characterized by a modulus recoverable to at least 80% of its value before the compression cycles were run, such as to at least 92% of its value before the compression cycles were run, such as at least 98% of its value before the compression cycles were run.

The soft tissue mimetic may have a lunate shape reinforced circumferentially and radially with polyamide fibers and tie lines. The soft tissue mimetic may have an instantaneous modulus between about 0.5 MPa and about 3 MPa, an equilibrium compressive modulus between about 0.05 and about 0.8 MPa, and or a tensile modulus between about 0.5 MPa and about 140 MPa. The soft tissue mimetic may have chain ends of the SO which are functionalized with azide and alkyne groups.

The present disclosure further provides a knee meniscus replacement, comprising a lunate body formed from a block copolymer hydrogel and reinforcements circumferentially and radially disposed within the lunate body. The block copolymer hydrogel comprises a glass formed from a dry blend of polystyrene-poly(ethylene oxide) diblock copolymer (SO) and polystyrene-poly(ethylene oxide)-polystyrene triblock copolymer (SOS) in a molar ratio from between 95:5 and 1:99 SO/SOS; and a liquid medium at a concentration between about 32:1 and about 2:1 liquid medium/SO-SOS by weight. The reinforcements are selected from polyamide fibers, methylmethacrylate-functionalized polyamide fibers, acrylate-functionalized polyamide fibers, photo-crosslinked tie lines, and combinations thereof. The knee meniscus replacement has a fatigue resistance to at least 500,000 compression cycles.

Also provided herein are methods for preparing a soft tissue mimetic. In the method, a pair of negative molds are printed having an interior volume defined by a three-dimensional model of a native soft tissue. The interior volume of the pair of negative molds, a dry blend of polystyrene-poly(ethylene oxide) diblock copolymer (SO) and polystyrene-poly(ethylene oxide)-polystyrene triblock copolymer (SOS) in a molar ratio from between 95:5 and 1:99 SO/SOS is injected. The SO-SOS dry blend is heated to form an SO-SOS melt. The SO-SOS melt is allowed to attain ambient temperature to form an SO-SOS glass. The SO-SOS glass is contacted with a liquid medium to form a block copolymer hydrogel. Once completed, the method produces a soft tissue mimetic having a fatigue resistance to at least 500,000 compression cycles.

The SO-SOS dry blend may be formed by dissolving the SO and SOS in an organic solvent and removing the organic solvent. The molar ratio may be between about 80:20 and about 20:80 SO/SOS, such as between about 70:30 and about 20:80 SO/SOS. The SO-SOS dry blend may be heated to a temperature between about 100° C. and about 180° C. within the negative mold. The SO-SOS dry blend may be heated under a pressure between about 50 psig and about 800 psig within the negative mold, such as between about 400 psig and about 600 psig within the negative mold. The SO-SOS dry blend may be heated for between about 5 minutes and about 50 minutes within the negative mold. The SO-SOS glass may be contacted with the liquid medium occurs at a temperature above 0° C. and below about 20° C. The block copolymer hydrogel may have a content of liquid medium between about 32:1 and 2:1 liquid medium/SO-SOS by weight, such as between about 16:1 and about 4:1 liquid medium/SO-SOS by weight. In particular the liquid medium may be water or aqueous buffer.

The method may further comprise using a scan to prepare the three-dimensional model of the native soft tissue. The method may also further comprise placing reinforcement fibers in the negative mold before injecting the SO-SOS dry blend. The reinforcement fibers may be selected from polyamide fibers, methylmethacrylate-functionalized polyamide fibers, and acrylate-functionalized polyamide fibers. The method may further comprise photo-crosslinking a portion of block copolymer hydrogel to from a reinforcement tie line. The chain ends of the SO may be functionalized with azide and alkyne groups, and the method further may further comprise coupling the SO chain ends in the liquid medium to modify the SO/SOS molar ratio.

BRIEF DESCRIPTION OF THE DRAWINGS

In addition to the exemplary aspects and embodiments described above, further aspects and embodiments will become apparent by reference to the drawings and by study of the following descriptions.

FIG. 6. Behavior of baseline SO/SOS hydrogels as a function of SOS triblock copolymer composition. FIG. 6A Swelling ratio (Q). FIG. 6B Elastic modulus (G') under dynamic shear (ω=1 Hz); FIG. 6C Compressive modulus (K) in unconfined compression (strain rate=20% min$^{-1}$). FIG. 6D Tensile tests, (strain rate=5 mm s$^{-1}$). Insets in FIG. 6B and FIG. 6C describe the dynamic frequency sweep and unconfined compression data for the baseline SO/SOS hydrogel containing 8.5 mol % SOS triblock copolymer. The inset in FIG. 6D provides a zoomed representation of the 8.5 mol % SOS hydrogel.

FIG. 10. Unconfined compression testing results showing stress (kPa) vs. extension ratio of swollen hydrogels of three distinct SOS blends (22, 46, and 72 mol %).

FIGS. 14(C-F) SOS61 held with tweezers. Elastomer-like bending (SOS61). Twisting ability (SOS30) from left to right.

FIG. 35A shows all 5000 cycles and FIG. 35B shows only the first 500 cycles of the test.

FIG. 39A shows all 5000 cycles and FIG. 39B shows only the first 500 cycles of the test.

FIG. 46A shows the first portion of the process, where a primary mesh is formed in the melt-state then swollen in water and then exposed to ultraviolet light.

FIGS. 55A&B. Photographs indicating the crosslinking of HA guest molecule in polymeric materials, without photobleaching the fluorescent label.

FIGS. 56A-D. Photographs indicating the effect of an attenuator on samples exposed to UV light.

FIG. 58A. Reconstruction of the microtomographic (μCT) slices into an object. FIG. 58B shows the object of FIG. 58A converted to a solid model with faces.

FIG. 59. Three-dimensional models of the human meniscus with different levels of smoothing. FIGS. 59A&D have 10,000 faces and no smoothing. FIGS. 59B&E have 500 faces with smoothing. FIGS. 59C&F have 300 faces with smoothing.

FIG. 60. Three-dimensional prints of the negative mold and the meniscus shape printed using a surface mesh reduced to 300 faces with smoothing. Print material used is acrylonitrile butadiene styrene material (ABS). FIG. 60A shows the meniscus shape in one half of the negative mold. FIG. 60B shows the meniscus shape removed from the negative mold.

FIG. 61. Examples of Tekscan implantation. FIG. 61A ovine knee with excess musculature removed. FIG. 61B depicts a joint more completely dissected showing a Tekscan™ sensor (model 6900) and 3D hydrogel construct. The inset image of FIG. 61B is an example of the pressure distribution data accessible through use of the Tekscan sensors (data from model 4010 shown).

DETAILED DESCRIPTION

Figure 1:
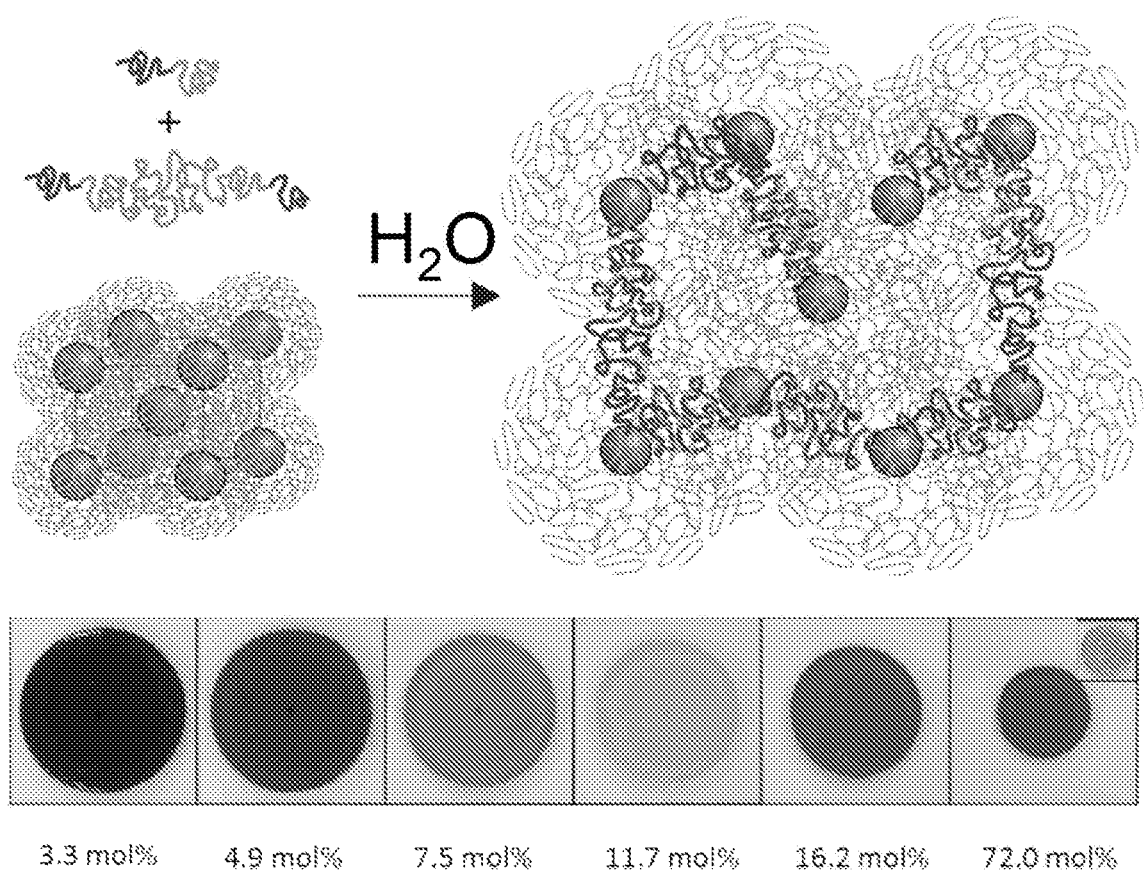
FIG. 1. Generalized fabrication strategy for block copolymer based hydrogels based on sphere-forming SO diblock and SOS triblock copolymer blends. Constituent block copolymers are pre-assembled in the melt and vitrified prior to swelling. SOS triblock copolymer (in bold) acts to tether adjacent spherical PS domains. The change in the amount of SOS triblock copolymer is labeled in mol %.

The present disclosure may be understood by reference to the following detailed description, taken in conjunction with the drawings as described above.

Provided herein is a soft tissue mimetic formed from a block copolymer hydrogel. "Hydrogel" as used herein refers to a gel (substantially dilute cross-linked system) in which the liquid component is a liquid medium comprising an aqueous medium. The hydrogel comprises a glass formed from a dry blend of polystyrene-poly(ethylene oxide) diblock copolymer (SO) and polystyrene-poly(ethylene oxide)-polystyrene triblock copolymer (SOS) in a molar ratio from between 95:5 and 1:99 SO/SOS, and a liquid medium at a concentration between about 32:1 and about 2:1 liquid medium/SO-SOS by weight. The soft tissue mimetic has a fatigue resistance to at least 500,000 compression cycles. In particular the soft tissue mimetic may be a knee meniscus replacement, comprising a lunate body formed from a block copolymer hydrogel and reinforcements circumferentially and radially disposed within the lunate body.

Also provided herein are methods for preparing a soft tissue mimetic. In the method, a pair of negative molds are printed having an interior volume defined by a three-dimensional model of a native soft tissue. The interior volume of the pair of negative modes, a dry blend of polystyrene-poly (ethylene oxide) diblock copolymer (SO) and polystyrene-poly(ethylene oxide)-polystyrene triblock copolymer (SOS) in a molar ratio from between 95:5 and 1:99 SO/SOS is injected. The SO-SOS dry blend is heated to form an SO-SOS melt. The SO-SOS melt is allowed to attain ambient temperature to form an SO-SOS glass. The SO-SOS glass is contacted with a liquid medium to form a block copolymer hydrogel. Once completed, the method produces a soft tissue mimetic having a fatigue resistance to at least 500,000 compression cycles.

The swellable polymer network is produced by using melt-state self-assembly of blends of poly(A)-block-poly(B) or AB diblock copolymers, with ABA triblock copolymers, synthetically designed to thermodynamically adopt a sphere morphology during microphase separation of the blocks. Each spherical aggregate contains a number of block copolymer chains, depending on the overall molecular weight of the block copolymer and its composition. Mass fractions of A block in the 0.05 to 0.20 range typically formed spherical aggregates during microphase separation in melt-state, with the A block (known as the minority component) forming a spherical core, and the B block forming a coronal brush-like layer coating that core. Spherical aggregates can contain from 100 to 400 A block chains, depending on molecular weight and composition of the AB diblock copolymer. In any specific system, the number of chains in an aggregate is fairly constant, providing aggregates with very narrow size distributions.

Core diameters typically range between 5 nm and 40 nm, depending on the molecular weight and composition of the specific block copolymer. The core diameters were centered about a mean value plus or minus a couple nanometers, with the breadth of this distribution narrowing with increased annealing time in the melt. The ABA triblock copolymer tethered the spherical aggregates and formed the network. ABA triblock copolymer compositions with greater than 17 mol % impart exceptional fatigue resistance. Changing the B block lengths in the ABA triblock copolymer enhanced swelling and improved modulus. The in-situ formation of dangling-end double networks using functionalized AB diblock copolymer dramatically improves the fatigue resistance and elasticity at low ABA triblock copolymer concentrations.

Additional embodiments and features are set forth in part in the description that follows, and in part will become apparent to those skilled in the art upon examination of the specification, or may be learned by the practice of the embodiments discussed herein. A further understanding of the nature and advantages of certain embodiments may be realized by reference to the remaining portions of the specification, the drawings, the chemical structures, and descriptions, which forms a part of this disclosure. Any description of any R-group or chemical substituent, alone or in any combination, may be used in any chemical Formula described herein, and Formulae include all conformational and stereoisomers, including diastereomers, epimers, and enantiomers. Moreover, any feature of a copolymer disclosed herein may be used in combination with any other feature of a copolymer disclosed herein, including but not limited to the physical properties of the copolymer, properties of the guest molecule disposed therein or thereupon, or any intermediate structures, metastructures or combinations.

(a) Soft Tissue Mimetics

"Soft tissue" includes tendons, ligaments, fascia, skin, fibrous tissues (such as fibrocartilage), fat, and synovial membranes (which are connective tissue), and muscles, nerves and blood vessels (which are not connective tissue). A "soft tissue mimetic" is an artificial material which mimics the behavior a natural soft tissue. The mimics should exhibit in-vivo mechanical anisotropy, biocompatibility, antifouling, and lubricity.

By way of non-limiting examples, the soft tissue may be a tendon, ligament, facium, skin, fibrous tissue, fat, synovial membrane, muscle, nerve, or blood vessel. The soft tissue may be a tendon, for example, rotator cuff tendons at the shoulder, including teres minor tendon, infraspinatus tendon, supraspinatus tendon, and subscapularis tendon; tendons that help bend the elbow or rotate the forearm, including deltoid tendon, biceps tendon, triceps tendon, brachioradialis tendon, and supinator tendon; tendons that help bend the wrist, including flexor carpi radialis tendon, flexor carpi ulnaris tendon, extensor carpi radialis tendon, and extensor carpi radialis brevis tendon; tendons that help move the legs and hips, including liopsoas tendon, obturator internus tendon, adductor longus tendon, adductor brevis tendon, adductor magnus tendons, gluteus maximus tendon, and gluteus medius tendon; tendons that help bend or straighten the knee, including quadriceps tendons, which includes the patellar tendon that contains the kneecap (patella), hamstring tendon, and sartorius tendon; tendons that cross the ankle joint and help move the foot up and down or side to side, including gastrocnemius tendon, which includes the Achilles tendon, soleus tendon, tibialis anterior tendon, and peroneus longus tendon; tendons that help finger movement, including flexor digitorum longus tendon, interosseus tendon, flexor digitorum profundus tendon, and abductor digiti minimi tendon; tendons that help thumb movement, including opponens pollicis tendon, flexor pollicis longus tendon, and extensor and abductor pollicis tendon; tendons that help bend and straighten toes, including flexor hallucis longus tendon, flexor digitorum brevis tendon, lumbrical tendon, abductor hallucis tendon, flexor digitorum longus tendon, and abductor digiti minimi tendon; tendon that help move the eyes, eyelids and jaw, including ocular tendon, levator palpebrae tendon, masseter tendon, and temporalis tendon; tendons that attach parts of the head to the collarbone, breastbone, shoulder blades or bones in the back that help move the head and neck, including trapezius tendon, sternocleidomastoid tendon, semispinalis capitis tendon, splenius capitis tendon, mylohyoid tendon, thyrohyoid tendon, and sternohyoid tendon; and tendons in the torso that twist and turn the body, maintain posture, or bend and straighten the trunk, including rectus abdominis tendon, external oblique tendon, transversus abdominis tendon, latissimus dorsi tendon, and erector spinae tendons.

The soft tissue may be a muscle, for example, rotator cuff muscle at the shoulder, including teres minor, nfraspinatus, supraspinatus, and subscapularis; muscles that bend the elbow or rotate the forearm, including deltoid, biceps, triceps, brachioradialis, and supinator; muscles that bend the wrist, including flexor carpi radialis, flexor carpi ulnaris, extensor carpi radialis, and extensor carpi radialis brevis; muscles that move the legs and hips, including liopsoas, obturator internus, adductor longus, adductor brevis, adductor magnus, gluteus maximus, and gluteus medius; muscles that bend or straighten the knee, including quadriceps, hamstring, and sartorius; muscles that cross the ankle joint and move the foot up and down, or side to side, including gastrocnemius, soleus, tibialis anterior, and peroneus longus; muscles that move the fingers, including flexor digitorum longus, interosseus, flexor digitorum profundus, and abductor digiti minimi; muscles that move the thumb, including opponens pollicis, flexor pollicis longus, extensor and abductor pollicis; muscles that bend and straighten toes, including flexor hallucis longus, flexor digitorum brevis, lumbrical, abductor hallucis, flexor digitorum longus, and abductor digiti minimi; muscles that move the eyes, eyelids and jaw, including ocular, levator palpebrae, masseter, and temporalis; muscles connected to the head, collarbone, breastbone, shoulder blades, including trapezius, sternocleidomastoid, semispinalis capitis, splenius capitis, mylohyoid and thyrohyoid, and sternohyoid; muscles in the torso that twist and turn the body, maintain posture, or bend and straighten the trunk, including rectus abdominis, external oblique, transversus abdominis, latissimus dorsi, and erector spinae.

The soft tissue may be a ligament, for example figments in the back region, including, anterior longitudinal ligament, interspinous ligament, intervertebral disc, ligamenta glava, nuchal ligament, posterior longitudinal ligament, and supraspinous ligament; ligaments in the upper limbs, including annular ligament, coracoacromial ligament, costoclavicular ligament, inferior, middle, and superior glenohumeral ligaments, dorsal and palmar intercarpal ligaments, interclavicular ligament, interosseous membrane, oblique cord, radial collaterall ligament, sternoclavicular ligament, transverse humeral ligament, seep and superior transverse metacarpal ligaments, and ulnar collateral ligament; ligaments in the head and neck, including corral suture, intermaxillar suture, lambdoidal suture, metopic suture, pterion, sagittal suture, sphenomadibular ligament, squamosal suture, and stylomandibular ligament; ligaments in the thorax, including costal cartilage, radiate sternocostal ligament, and sternal angle; ligament in the abodoment, including inguinal ligament, lacunar ligament, and pectineal ligament; figments in the pelvis and perineum, including iliolumbar ligament, public symphysis, sacrospinous ligament, and sacrotuberous ligament; and ligaments in the lower limbs, including acetabular labrum, anterior cruciate ligament, anterior talofibular ligament, anterior tibiofibular ligament, anterior tibiotalar ligament, calceneofibular ligament, deltoid ligament, fibular collateral ligament, iliofemoral ligament, deep and superficial infrapatellar bursa, interosseous membrane, ischiofemoral ligament, figment of the head of the femur, long plantar ligament, longitudinal arch of the foot, knee meniscus (medial, laterial and interior), patellar ligament, plantar calcaneocuboid ligament, plantar calcaneonavicular ligament, posterior cruciate ligament, posterior meniscofemoral ligament, posterior talofibular ligament, posterior tibiofibular ligament, posterior tibiotalar ligament, prepatellar bursa, pubofemoral ligament, suprapatellar bursa, tibial collateral ligament, tibiocalcaneal ligament, tibonavicular ligament, transverse acetabular ligament, transverse arch of the foot, and zona orbicularis. In particular, the soft tissue may be a knee meniscus. The soft tissue may be an intervertebral disc.

Menisci are lunate fibrocartilaginous tissues responsible for distributing tibial-femoral contact pressure in the knee and facilitating articulation. When menisci become damaged, such as through traumatic injury or age-related degeneration, the mostly avascular menisci have limited to no healing capacity and are unable to function in the knee. Thus, the underlying articular cartilage can rapidly degrade, leading to end-stage osteoarthritis (OA).

The knee meniscus replacement disclosed herein comprises a biphasic composite polymer network engineered to provide a mechanical response analogous to native meniscal tissue, while simultaneously being durable and biocompatible, and having surface friction characteristics amenable to long-term joint integration. The disclosed implants comprise an underlying polymer network produced using the melt-state self-assembly of block copolymers based on polystyrene ("PS", minority component 8-10%) and polyethylene oxide ("PEO", or "PEG", 90-92%). Without wishing to be bound by theory, the molecular system self-assembles into a homogeneous network of trillions of mechanically-tethered 20-nm PS spheres per milligram of composite, each coated by a dense coronal brush of PEG-based polymer chains. A secondary interpenetrating GAG (e.g. hyaluronan) network ("HA IPN") may then be spatially photopatterned within the primary PS-PEO-based system to spatially mimic the mechanical anisotropy. This unique nanoscale structure, tethering methodology, and HA IPN are incredibly efficient at distributing stress, and can reproduce the biphasic relaxation behavior with complete elastic recovery even after repetitive (cyclic) loading. Subsequent circumferential reinforcement of this network with non-absorbable sutures provides direct attachment mechanisms during surgical implantation.

The mechanical anisotropy has been correlated directly to the biased directional orientation of type I collagen fibers running through the meniscal tissue. In particular, the predominance of fibers running parallel to the circumferential direction produces a characteristically large tensile modulus that appears critical for rapid distribution of load. Additional radial "tie" fibers give rise to a smaller but still significant tensile modulus in the radial direction, while also bolstering the meniscus from longitudinal tearing. Meanwhile, the arrangement of both the circumferential and radial fibers in planes parallel to the tibial plateau allow the compressive moduli in the radial and axial directions to remain much more moderate. Compression in these directions is reliant less on the collagen fiber network and more on the viscoelasticity of non-fibrous matrix to dissipate load across the entire contact surface.

The soft tissue mimetic may have an instantaneous modulus ranging between about 0.5 MPa and about 3 MPa, such as between about 0.5 MPa and 1 MPa, between about 1 MPa and 1.5 MPa, between about 1.5 MPa and 2 MPa, between about 2 MPa and 2.5 MPa, or between about 2.5 MPa and 3 MPa. The instantaneous modulus may be greater than about 0.5 MPa. The instantaneous modulus may be less than about 3 MPa.

The soft tissue mimetic may have an equilibrium compressive modulus ranging between about 0.05 MPa and about 0.8 MPa, such as between about 0.05 MPa and about 0.1 MPa, between about 0.1 MPa and about 0.2 MPa, between about 0.2 MPa and about 0.3 MPa, between about 0.3 MPa and about 0.4 MPa, between about 0.4 MPa and about 0.5 MPa, between about 0.5 MPa and about 0.6 MPa, between about 0.6 MPa and about 0.7 MPa, or between about 0.7 MPa and about 0.8 MPa. The equilibrium compressive modulus may be greater than about 0.05 MPa. The equilibrium compressive modulus may be less than about 0.8 MPa.

The soft tissue mimetic may have a tensile modulus ranging between about 0.5 MPa and about 140 MPa, such as between about 0.5 MPa and about 1 MPa, between about 1 MPa and about 2 MPa, between about 2 MPa and about 3 MPa, between about 3 MPa and about 4 MPa, between about 4 MPa and about 5 MPa, between about 5 MPa and about 6 MPa, between about 6 MPa and about 7 MPa, between about 7 MPa and about 8 MPa, between about 8 MPa and about 9 MPa, between about 9 MPa and about 10 MPa, between about 10 MPa and about 20 MPa, between about 20 MPa and about 30 MPa, between about 30 MPa and about 40 MPa, between about 40 MPa and about 50 MPa, between about 50

MPa and about 60 MPa, between about 60 MPa and about 70 MPa, between about 70 MPa and about 80 MPa, between about 80 MPa and about 90 MPa, between about 90 MPa and about 100 MPa, between about 100 MPa and about 110 MPa, between about 110 MPa and about 120 MPa, between about 120 MPa and about 130 MPa, or between about 130 MPa and about 140 MPa. The tensile modulus may be greater than about 0.5 MPa. The tensile modulus may be less than about 140 MPa.

(b) Thermoplastic Elastomeric Hydrogels

The present disclosure provides soft tissue mimetics that comprise: a block copolymer hydrogel, comprising a glass formed from a dry blend of polystyrene-poly(ethylene oxide) diblock copolymer (SO) and polystyrene-poly(ethylene oxide)-polystyrene triblock copolymer (SOS) in a molar ratio from between 95:5 and 1:99 SO/SOS; and a liquid medium at a concentration between about 32:1 and about 2:1 liquid medium/SO-SOS by weight. The block copolymer hydrogel may have a fatigue resistance to at least 500,000 compression cycles.

The block copolymer-based hydrogels have a regular structure attained through self-assembly in the melt state, leading to a more homogeneous network formation. This non-solution based thermally processable gel formation allowed the hydrogel to be shaped before swelling, giving it many industrial advantages of plastics, such as die-casting and coating capabilities. Also, blending relative amounts of the two constituents tuned the mechanical properties of the gel through a large range.

The two-component polystyrene-poly(ethylene oxide) diblock (SO) and polystyrene-poly(ethylene oxide)-polystyrene triblock (SOS) copolymer-based hydrogel system does not form through chemical crosslinkers like conventional brittle hydrogels. Instead, self-assembly of block copolymers into micellar domains in the melt state physically crosslinked the polystyrene cores through the SOS tethers (FIG. 1). This formation produced far fewer fixed junction points than found in most crosslinked hydrogels.

For example, the molecular weight between fixed junction points in a typical crosslinked PVA hydrogel is about $10^3$-$10^4$, where the present hydrogel allows a molecular weight of more than $10^5$ between crosslinks, creating a high degree of mobility within the system and allowing energy absorption without straining the polymer chains. Energy absorption was typically facilitated through extensive chain stretching and the recoverable sliding of topologically constrained entanglements in the O block of the SOS triblock tethers. Additionally, the dynamic and transient entanglements of the O chains in the SO diblock copolymer with other chains in the swollen O matrix could reversibly absorb energy through chain reptation without breaking bonds.

(i) SO-SOS Glass

The block copolymer hydrogels described herein comprise a glass formed from a dry blend comprising diblock copolymer and a copolymer (SOS) in a molar ratio from between 95:5 and 1:99 diblock to triblock copolymer. In some embodiments, the block copolymer hydrogels described herein comprise a glass formed from a dry blend comprising polystyrene-poly(ethylene oxide) diblock copolymer (SO) and polystyrene-poly(ethylene oxide)-polystyrene triblock copolymer (SOS) in a molar ratio from between 80:20 and 1:99 SO/SOS. The polystyrene blocks may be hydrogenated, for example to polycyclohexylethlene (PCHE).

As used herein, "glass" refers to completely vitrified solids as well as to partially crystalline or glassy solids. Generally, a "glass" is a material below its glass transition temperature ($T_g$), as defined by for example differential scanning calorimetry (DSC) or dynamic mechanical analysis (DMA). Use temperatures defined as a range include all temperatures in which the swelling medium remains in the liquid phase. For aqueous media this may have a range including 0-100° C. Typically, the glassy domains may have a glass transition temperature of at least 60° C.

Thermoplastic elastomer (TPE) hydrogels described herein possessed fatigue resistance (toughness) and elasticity not typically found in processable, physically crosslinked hydrogels. These TPE hydrogels were fabricated by melt blending sphere-forming AB diblock and ABA triblock copolymers followed by vitrifying or chemical cross-linking of the isolated spherical domains of block A which form during the self-assembly process (FIG. 1). Each sphere comprised several hundred minority component (A) blocks, which were necessarily (by block connectivity) enveloped by a dense brush of equal number majority component (B) blocks, giving rise to the micelle-like appearance. Without solvent present, a highly regular and periodic lattice of densely packed micelles was produced. Vitrifying or crosslinking the interior spherical domain (A blocks) allowed one to completely preserve the melt state self-assembled structure both on the micro- and macroscale. Upon selectively hydrating the majority component (B blocks), the lattice of micelles expanded as liquid medium penetrated the dense coronal brush layer of each micelle.

The ABA triblock copolymer, even at small quantities, tethers individual micelles together into an infinite network. Each sphere was a junction point in physically cross-linked system. Equilibrium swelling dimensions were determined by the balance of osmotic swelling forces, entropic restoring forces contributed by the ABA tethering midblocks, and the quantity of topological ABA entanglements produced within the network (FIG. 1) during self-assembly. Generally, the A blocks are a polystyrenic block, such as polystyrene or polycyclohexylethylene. The B blocks are a polyether, such as polyethylene oxide (PEO).

Unexpectedly, at low SOS concentrations the most elastic modulus was produced not by the tethering concentration itself, but through the overlap in the PEO coronal brush layers imposed by the topologically constrained entanglements in the tethers. Without wishing to be bound by theory, the dynamic (non-topologically constrained) entanglements among the dangling PEO chain ends appeared to be responsible for a considerable fraction of the mechanical response under small-strain dynamic shear.

The homogeneous structure provided by melt-state self-assembly of macromolecular block copolymers produced a primary or first network that was quite tough compared with most hydrogel systems. These networks could absorb strains elastically to a few hundred percent, with the exact modulus exhibited tunable through the triblock copolymer content in the original melt-state blend. However, installing a second network of tethers that, instead of altering the mechanical performance directly, remained largely passive under small strain conditions could increase fatigue resistance dramatically. Without wishing to be bound by theory, the secondary network of tethers was only actively engaged when the primary network approaches its strain limitations, thereby improving the high strain fatigue resistance of the hydrogel without impacting the smaller strain mechanical response of the primary network. Adding this second network of tethers could also be done without sacrificing the thermoprocessibility of the system.

The large number of hydroxyl-terminated diblock copolymers comprising each micellar domain could be exploited.

For example, the hydroxyl groups may be activated with leaving groups, such as mesyl or tosyl, or activated with a strong base, such as sodium hydride. The activated hydroxyl groups may then be converted to pairs of orthogonal groups, such as alkynes and azides. These orthogonal groups can react with each other within the polymer, such as in a 1,3-dipolar Huisgen cycloaddition between the azide and alkyne to form a 1,2,3-triazole. The Huisgen cycloaddition is also called the "click reaction." Using orthogonal chemistry, excess diblock copolymer could be coupled to form additional triblock copolymer in situ after the hydrogel has already reached equilibrium.

Not wishing to be bound by theory, the triblock copolymer added in the original melt blend and that which formed via Cu(I)-catalyzed Huisgen coupling between azide and alkyne terminal groups in the hydrated state were molecularly identical (effectively), but the stress state of these two triblock copolymer populations was significantly different. The triblock copolymer present during melt-state self-assembly of the spherical morphology became trapped in its current conformation during sample vitrification. Upon exposure to aqueous media, the entropic restoring force in the tethering midblocks of the triblock copolymer population, combined with topological entanglements present among nearby tethers, precluded infinite swelling and osmotically-driven micelle dispersal. The concentration of topological entanglements scaled with triblock copolymer composition, and dramatically influenced the equilibrium dimensions. Effectively, the osmotic driving force to swell was opposed by an equal and opposite force supplied by the entangled triblock copolymer adjoining the spherical PS domains.

In contrast, triblock copolymer formed through diblock copolymer coupling in the hydrated state at swelling equilibrium produces a population of tethers free of the mechanical stress osmotically imposed on the primary network. Importantly, with the exception of the Cu(I) catalyst specific to this particular choice of chemistry, formation of the DN through the coupling of dangling chain ends lacked leachable small molecule reagents or sol fractions intrinsic to traditional DN hydrogel systems.

The block copolymer may comprise at least one polyalkylene oxide block, especially polyethylene oxide (PEO). The PEO may have an average molecular weight of 3 kDa to 400 kDa. For example, the PEO may have an average molecular weight from about 3 kDa to about 5 kDa, from about 5 kDa to about 10 kDa, from about 10 kDa to about 15 kDa, from about 15 kDa to about 20 kDa, from about 20 kDa to about 25 kDa, from about 25 kDa to about 30 kDa, from about 30 kDa to about 35 kDa, from about 35 kDa to about 40 kDa from about 40 kDa to about 45 kDa, from about 45 kDa to about 50 kDa, from about 50 kDa to about 55 kDa, from about 55 kDa to about 60 kDa, from about 60 kDa to about 65 kDa, from about 65 kDa to about 70 kDa, from about 70 kDa to about 75 kDa, from about 75 kDa to about 80 kDa, from about 80 kDa to about 85 kDa, from about 85 kDa to about 90 kDa, from about 90 kDa to about 95 kDa, from about 95 kDa to about 100 kDa, from about 100 kDa to about 105 kDa, from about 105 kDa to about 110 kDa, from about 110 kDa to about 115 kDa, from about 115 kDa to about 120 kDa, from about 120 kDa to about 125 kDa, from about 125 kDa to about 130 kDa, from about 130 kDa to about 135 kDa, from about 135 kDa to about 140 kDa, from about 140 kDa to about 145 kDa, from about 145 kDa to about 150 kDa, from about 150 kDa to about 155 kDa, from about 155 kDa to about 160 kDa, from about 160 kDa to about 170 kDa, from about 170 kDa to about 180 kDa, from about 180 kDa to about 190 kDa, from about 190 kDa to about 200 kDa, from about 200 kDa to about 250 kDa, from about 250 kDa to about 300 kDa, from about 300 kDa to about 350 kDa, or from about 350 kDa to about 400 kDa. The PEO may have an average molecular weight of greater than about 100 kDa. The PEO may have an average molecular weight of less than 400 kDa.

The block copolymer may comprise at least one polystyrene block (PS). The PS may have an average molecular weight of 3 kDa to 160 kDa. For example, the PS may have an average molecular weight from about 3 kDa to about 5 kDa, from about 5 kDa to about 10 kDa, from about 10 kDa to about 15 kDa, from about 15 kDa to about 20 kDa, from about 20 kDa to about 25 kDa, from about 25 kDa to about 30 kDa, from about 30 kDa to about 35 kDa, from about 35 kDa to about 40 kDa from about 40 kDa to about 45 kDa, from about 45 kDa to about 50 kDa, from about 50 kDa to about 55 kDa, from about 55 kDa to about 60 kDa, from about 60 kDa to about 65 kDa, from about 65 kDa to about 70 kDa, from about 70 kDa to about 75 kDa, from about 75 kDa to about 80 kDa, from about 80 kDa to about 85 kDa, from about 85 kDa to about 90 kDa, from about 90 kDa to about 95 kDa, from about 95 kDa to about 100 kDa, from about 100 kDa to about 105 kDa, from about 105 kDa to about 110 kDa, from about 110 kDa to about 115 kDa, from about 115 kDa to about 120 kDa, from about 120 kDa to about 125 kDa, from about 125 kDa to about 130 kDa, from about 130 kDa to about 135 kDa, from about 135 kDa to about 140 kDa, from about 140 kDa to about 145 kDa, from about 145 kDa to about 150 kDa, from about 150 kDa to about 155 kDa, or from about 155 kDa to about 160 kDa. The PS may have an average molecular weight of greater than about 3 kDa. The PS may have an average molecular weight of less than 160 kDa. In particular, the PS may have an average molecular weight between about 5 kDa and about 20 kDa.

Upon heating, the copolymer may form domains of the at least one polystyrene block and of the at least one polyalkylene oxide block that are substantially co-continuous with domain sizes from about 5 nm to about 50 nm. For example, the domains may have sizes of about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, about 25 nm, about 26 nm, about 27 nm, about 28 nm, about 29 nm, about 30 nm, about 35 nm, about 40 nm, about 45 nm, or about 50 nm. The domain size may be greater than about 5 nm. The domain size may be less than 50 nm. In particular, the PEO domain is typically between about 22 nm and about 27 nm. The PS domain is typically between about 18 nm and about 20 nm. At higher molecular weights, the domain size of the PEO domain may be almost 50 nm.

The polystyrene may be partially hydrogenated, yielding cyclohexyl, cyclohexenyl, and cyclohexadienyl moieties. For example, PS domain of the block copolymer may be based on the hydrogenated forms of styrenic monomers, such as vinyl cylcohexylethylene. Hydrogenation may occur under increased partial pressure of hydrogen with or without a catalyst, such as palladium, platinum, rhodium, ruthenium, nickel, or other metal. The catalyst may have a support matrix, such as calcium carbonate ($CaCO_3$), carbon, or porous silica. Suitable examples of hydrogenation catalysts include palladium on carbon, palladium on calcium carbonate, and platinum on porous silica.

In some embodiments, the hydroxyl groups of the diblock copolymer may be activated with a leaving group, such as mesyl or tosyl. The activated hydroxyl group may be converted to an azide. The hydroxyl groups of the diblock copolymer may instead be activated with a strong base, such as sodium hydride. The activated hydroxyl group may be converted to any alkyne. When present together in the same hydrogel, the hydroxyl groups of diblock copolymers having alkynes and azides may react together in a Huisgen cycloaddition, resulting in new triblock copolymers formed between the reacted segments within the hydrogel.

(ii) Liquid Medium

The diblock copolymer hydrogel also comprises a liquid medium at a concentration of between about 32:1 and about 2:1 liquid medium/SO-SOS by weight. The liquid medium may be an aqueous medium.

The aqueous medium may be water, a buffer, such as phosphate-buffered saline (PBS) or Ringer's solution, or the like. In particular, the aqueous medium may be buffer. In other embodiments, the aqueous medium may be water.

Generally, the block copolymer hydrogel may have a water concentration between about 32:1 and 2:1 water/SO-SOS by weight, such as between about 32:1 to 30:1 water/SO-SOS by weight, between about 30:1 to 28:1 water/SO-SOS by weight, between about 28:1 to 26:1 water/SO-SOS by weight, between about 26:1 to 24:1 water/SO-SOS by weight, between about 24:1 to 22:1 water/SO-SOS by weight, between about 22:1 to 20:1 water/SO-SOS by weight, between about 20:1 to 18:1 water/SO-SOS by weight, between about 18:1 to 16:1 water/SO-SOS by weight, between about 16:1 to 14:1 water/SO-SOS by weight, between about 14:1 to 12:1 water/SO-SOS by weight, between about 12:1 to 10:1 water/SO-SOS by weight, between about 10:1 to 8:1 water/SO-SOS by weight, between about 8:1 to 6:1 water/SO-SOS by weight, between about 6:1 to 4:1 water/SO-SOS by weight, or between about 4:1 to 2:1 water/SO-SOS by weight. The water concentration of the hydrogel may be between about 16:1 and about 4:1 water/SO-SOS by weight.

Generally, the block copolymer hydrogel may have a liquid medium concentration between about 32:1 and 2:1 liquid medium/SO-SOS by weight, such as between about 32:1 to 30:1 liquid medium/SO-SOS by weight, between about 30:1 to 28:1 liquid medium/SO-SOS by weight, between about 28:1 to 26:1 liquid medium/SO-SOS by weight, between about 26:1 to 24:1 liquid medium/SO-SOS by weight, between about 24:1 to 22:1 liquid medium/SO-SOS by weight, between about 22:1 to 20:1 liquid medium/SO-SOS by weight, between about 20:1 to 18:1 liquid medium/SO-SOS by weight, between about 18:1 to 16:1 liquid medium/SO-SOS by weight, between about 16:1 to 14:1 liquid medium/SO-SOS by weight, between about 14:1 to 12:1 liquid medium/SO-SOS by weight, between about 12:1 to 10:1 liquid medium/SO-SOS by weight, between about 10:1 to 8:1 liquid medium/SO-SOS by weight, between about 8:1 to 6:1 liquid medium/SO-SOS by weight, between about 6:1 to 4:1 liquid medium/SO-SOS by weight, or between about 4:1 to 2:1 liquid medium/SO-SOS by weight. The liquid medium concentration of the hydrogel may be between about 16:1 and about 4:1 liquid medium/SO-SOS by weight.

(iii) Therapeutic Agents

The block copolymer hydrogels described herein may further comprise an active pharmaceutical ingredients, such as a drug, a biological factor, therapeutic agent, or pharmaceutic agent. These hydrogels may be formed into a soft tissue mimetic, as described herein, providing an implantable medical device, or they may coat the surface of a medical device.

As such, the block copolymer hydrogels may be used to deliver therapeutic and pharmaceutic agents including, but not limited to, anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) II b/HI a inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (Cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), everolimus, azathioprine, mycophenolate mofetil); angiogenic agents: vascular endothelial growth factor (VEGF), fibroblast growth factor (FGF); angiotensin receptor blockers; nitric oxide donors; antisense oligonucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors. Also, it should be recognized that many active agents have multiple pharmaceutical uses other than those specifically recited.

The therapeutic and pharmaceutic agent may be present in the hydrogel at an amount from about 10 µg/cm$^2$ (micrograms drug/area of stent) to about 2000 µg/cm$^2$, such as from about 100 µg/cm$^2$ to about 1000 µg/cm$^2$, or from about 200 µg/cm$^2$ to about 500 µg/cm$^2$. In exemplary embodiments, the drug per area can include 150 µg/cm$^2$ to about 500 µg/cm$^2$, such as from about 175 µg/cm$^2$ to about 400 µg/cm$^2$, or from about 200 µg/cm$^2$ to about 300 µg/cm$^2$. Within this narrower range, the drug per area can include 210 µg/cm$^2$ to about µg/cm$^2$, or from about 215 µg/cm$^2$, to about 250 µg/cm$^2$, or 225 µg/cm$^2$±µg/cm$^2$. Alternatively, the amount of therapeutic and pharmaceutic agents in the hydrogel may be described as the total amount of drug per device. Accordingly, the amount of drug may be from about 0.5 mg to about 12 mg, such as from about 0.75 mg to about 10 mg, or from about 1 mg to about 5 mg.

The hydrogel and therapeutic and pharmaceutic agent may be configured to cooperate so as to form a diffusion pathway (e.g., lipophilic, hydrophilic and/or amphipathic) with tissue when the soft tissue mimetic or medical device is disposed in a body, such that the drug diffuses into the tissue over a body fluid passing through the body such that a maximum systemic blood concentration of the therapeutic and pharmaceutic agent is less than or about 30 ng/ml, less than or about 20 ng/ml, or less than or about 10 ng/ml. In one embodiment, the hydrogel may control the systemic delivery of the therapeutic and pharmaceutic agent so as to retain a sufficiently low concentration and inhibit negative systemic side effects. As such, the systemic delivery of the therapeutic and pharmaceutic agent may provide a preselected blood maximum concentration.

In one embodiment, the systemic delivery of the therapeutic and pharmaceutic agents may be characterized as concentration of drug per amount of total amount of drug in the hydrogel. As such, the systemic delivery of the drug provide a blood maximum concentration can be from about 0.16 ng/ml per milligram (mg) of drug in the hydrogel to about 4 ng/ml per mg total drug, such as from about 0.2 ng/ml per mg total drug to about 3.3 ng/ml per mg total drug, about 0.5 ng/ml per mg total drug to about 2.5 ng/ml per mg total drug, or about 0.75 ng/ml per mg total drug to about 0.8 ng/ml per mg total drug.

(c) Method of Making the Soft Tissue Mimetic

Provided herein are methods for preparing a soft tissue mimetic. In the method, a pair of negative molds are created having an interior volume defined by a three-dimensional model of a native soft tissue. The interior volume of the pair of negative molds, a dry blend of polystyrene-poly(ethylene oxide) diblock copolymer (SO) and polystyrene-poly(ethylene oxide)-polystyrene triblock copolymer (SOS) in a molar ratio from between 95:5 and 1:99 SO/SOS is injected. The SO-SOS dry blend is heated to form an SO-SOS melt. The SO-SOS melt is allowed to attain ambient temperature to form an SO-SOS glass. The SO-SOS glass is contacted with a liquid medium to form a block copolymer hydrogel. Once completed, the method produces a soft tissue mimetic having a fatigue resistance to at least 500,000 compression cycles.

(i) Blending of SO-SOS Dry Blend

The SO-SOS dry blend may be formed by dissolving the SO and SOS in an organic solvent and removing the organic solvent. The organic solvent may be a polar protic solvent, a polar aprotic solvent, a non-polar solvent, or combinations thereof. Suitable examples of polar protic solvents include, but are not limited to alcohols such as methanol, ethanol, isopropanol, n-propanol, isobutanol, n-butanol, s-butanol, t-butanol, and the like; diols such as propylene glycol; organic acids such as formic acid, acetic acid, and so forth; amines such as trimethylamine, or triethylamine, and the like; amides such as formamide, acetamide, and so forth; and combinations of any of the above. Non-limiting examples of suitable polar aprotic solvents include acetonitrile, dichloromethane (DCM), diethoxymethane, N,N-dimethylacetamide (DMAC), N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, 1,4-dioxane, N-methyl-2-pyrrolidinone (NMP), ethyl formate, formamide, hexamethylphosphoramide, N-methyl acetamide, N-methylformamide, methylene chloride, nitrobenzene, nitromethane, propionitrile, sulfolane, tetramethylurea, tetrahydrofuran (THF), 2-methyltetrahydrofuran, trichloromethane, and combinations thereof. Suitable examples of non-polar solvents include, but are not limited to, alkane and substituted alkane solvents (including cycloalkanes), aromatic hydrocarbons, esters, ethers, combinations thereof, and the like. Specific non-polar solvents that may be employed include, for example, benzene, butyl acetate, t-butyl methylether, chlorobenzene, chloroform, chloromethane, cyclohexane, dichloromethane, dichloroethane, diethyl ether, ethyl acetate, diethylene glycol, fluorobenzene, heptane, hexane, isopropyl acetate, methyltetrahydrofuran, pentyl acetate, n-propyl acetate, tetrahydrofuran, toluene, and combinations thereof. In particular, the solvent may be benzene or toluene.

Before blending, the SOS may be formed by synthesis from SO starting material, and then isolated using iterative fractionation. The solvent used for iterative fractionation may be any organic solvent described herein, particular chloroform or n-hexane. The purity of SOS after iterative fractionation may be greater than 95 mol %, such as greater than 98 mol %, or about 99 mol %.

In the SO-SOS dry blend, the molar ratio may be between about 95:5 and about 1:99 SO/SOS, such as between about 95:5 and about 90:10 SO/SOS, such as between about 90:10 and about 85:15 SO/SOS, such as between about 85:15 and about 80:20 SO/SOS, such as between about 80:20 and about 75:25 SO/SOS, such as between about 75:25 and about 70:30 SO/SOS, between about 70:30 and about 65:35 SO/SOS, between about 65:35 and about 60:40 SO/SOS, between about 60:40 and about 55:45 SO/SOS, between about 55:45 and about 50:50 SO/SOS, between about 50:50 and about 55:45 SO/SOS, between about 55:45 and about 45:65 SO/SOS, between about 45:65 and about 40:60 SO/SOS, between about 40:60 and about 35:65 SO/SOS, between about 35:65 and about 30:70 SO/SOS, between about 30:70 and about 25:75 SO/SOS between about 25:75 and about 20:80 SO/SOS, between about 20:80 and about 15:85 SO/SOS, between about 15:85 and about 10:90 SO/SOS, between about 10:90 and about 5:95 SO/SOS, or between about 5:95 and about 1:99 SO/SOS. In particular, the molar ratio may between about 70:30 and about 20:80 SO/SOS, between about 60:40 and about 30:70 SO/SOS, or at about 40:60 SO/SOS. The molar ratio may also be about 4:96 SO/SOS, about 3:97 SO/SOS, about 2:98 SO/SOS, or about 1:99 SO/SOS.

(ii) Heating of SO-SOS Dry Blend

The SO-SOS dry blend is processed under a combination of pressure and heat for a period of time to form an SO-SOS glass. As used herein, "glass" refers to completely vitrified solids as well as to partially crystalline or glassy solids. The SO-SOS dry blend may be heated to a temperature between about 100° C. and about 180° C., such as between about 100° C. and about 110° C., between about 110° C. and about 120° C., between about 120° C. and about 130° C., between about 130° C. and about 140° C., between about 140° C. and about 150° C., between about 150° C. and about 160° C., between about 160° C. and about 170° C., or between about 170° C. and about 180° C. The temperature may be between about 140° C. and about 160° C., such as about 150° C.

The SO-SOS dry blend may be heated without or without pressure. If heated under pressure, the SO-SOS dry blend may be heated under a pressure between about 50 psig and about 800 psig, such as between about 50 psig and about 100 psig, between about 100 psig and about 150 psig, between about 150 psig and about 200 psig, between about 200 psig and about 250 psig, between about 250 psig and about 300 psig, between about 300 psig and about 350 psig, between about 350 psig and about 400 psig, between about 400 psig and about 450 psig, between about 450 psig and about 500 psig, between about 500 psig and about 550 psig, between about 550 psig and about 600 psig, between about 600 psig and about 650 psig, between about 650 psig and about 700 psig, between about 700 psig and about 750 psig, or between about 750 psig and about 800 psig. In particular, the pressure may be between about 200 psig and about 600 psig, or at about 500 psig.

Additionally, pressure may be applied to samples placed in a vacuum bag, such that a dynamic reduced pressure of less than 20 Torr inside the bag is achieved during heating. That is, the sample may be placed into a vacuum bag during operation of the press used to heat and squeeze the sample. Doing so has been discovered herein to reduce the number of microbubbles, as well as grain boundary and particle sintering defects in the melt.

The SO-SOS dry blend may be heated for between about 5 minutes and about 50 minutes, such as between about 5 minutes and about 10 minutes, between about 10 minutes and about 15 minutes, between about 15 minutes and about 20 minutes, between about 20 minutes and about 25 minutes, between about 25 minutes and about 30 minutes, between about 30 minutes and about 35 minutes, between about 35 minutes and about 40 minutes, between about 40 minutes and about 45 minutes, or between about 5 minutes and about 50 minutes. In particular, the SO-SOS dry blend may be heated for about 25 minutes, or for about 5 minutes.

The heating may occur in heating-cooling cycles, wherein the dry blend is heated for a period of time (e.g., 5 minutes) and then allowed to cool to ambient temperature before re-heating. Generally, the dry blend may pass through 1 to 10 cycles. Any combination of these features may be used for processing the dry blend. For example, the dry blend may be heated at 150° C. at 500 psig in a vacuum bag for 4 heating-cooling cycles.

As used herein "ambient temperature" is the temperature of the environment surrounding the process or experimental apparatus.

(iii) Crosslinking with a Guest Molecule

The method may further comprise incorporating a guest molecule, such as hyaluronic acid, and crosslinking the guest molecule to create an interpenetrating network (IPN) of HA within the SO/SOS hydrogel host. Within block copolymer hydrogels described herein, crosslinked hyaluronic acid (HA) may provide a secondary network. The HA may be a bonding intermediary between the hydrogel and directional fibers, such as nylon sutures, when present. Without wishing to be bound by theory, HA has many available functional groups through which both crosslinking and suture attachment can be achieved. For example, HA comprises primary alcohol and carboxylic acid groups which can be chemically modified for covalent attachment. In addition, hyaluronic acid possesses many desirable biological properties, including but not limited to, high lubricity, low immune response, hydrophilicity, and low protein absorption. The crosslinking provides chemical electrostatic attachment to directional fibers in the hydrogel, when present. The HA IPN may provide a direct mechanical correlation between the directional fiber and the SO/SOS hydrogel host.

An "interpenetrating polymer network" (IPN) refers to an intermingling of a guest molecule and a polymer host, wherein molecules of the guest have been crosslinked with each other. The polymer host is any block copolymer described herein.

The guest molecule may comprise a compound selected from the group consisting of polyions, polysaccharides including glycosaminoglycans (GAGs); salts of glycosaminoglycans, nucleic acids, polyvinylpyrrolidones, peptides, polypeptides, proteins, lipoproteins, polyamides, polyamines, polyhydroxy polymers, polycarboxy polymers, phosphorylated derivatives of carbohydrates, sulfonated derivatives of carbohydrates, interleukin-2, interferon, and phosphorothioate oligomers, with or without amino acids, as well as other hydrophilic polymers. Polyhydroxy polymers include, for example, polyvinyl alcohol and polyethylene glycol. Polycarboxy polymers include, for example, carboxymethylcellulose, alginic acid, sodium alginate, and calcium alginate.

The guest molecule may be any glycosaminoglycan (GAG). GAGs include any of a group of linear polysaccharides with various disaccharide repeating units and usually occurring in proteoglycans, including chondroitin sulfate, dermatan sulfate, heparan sulfate, and heparin, keratan sulfates, and hyaluronic acid. GAGs may be high molecular weight, low molecular weight, or oligomeric. GAGs or mucopolysaccharides are long unbranched polysaccharides consisting of a repeating disaccharide unit. The repeating unit consists of a hexose (six-carbon sugar) or a hexuronic acid, linked to a hexosamine (six-carbon sugar containing nitrogen). In a particular embodiment, the GAG is a chondroitin sulfate or a hyaluronan, such as hyaluronic acid.

Hyaluronan ("hyaluronic acid" or "HA") is a naturally occurring polysaccharide found in tissues and body fluids of vertebrates and in some bacteria. It is a linear polymer with high molecular weight linear polysaccharide containing alternating N-acetyl-D-glucosamine and D-glucuronic acid residues, with relatively high concentrations in the vitreous humor of eye, the umbilical cord, synovial joint fluid, rooster combs, and in native heart valve leaflets, particularly those regions of the valve subject to compression. A carboxyl group (—COOH) is attached to each disaccharide unit of hyaluronic acid. When in solution at physiological pH, hyaluronic acid is ionized, resulting in negatively charged —COO. The negatively charged flexible chains take on an expanded conformation and entangle with each other at very low concentrations, acting as a stiff random coil. In solutions with higher concentration of hyaluronic acid, stiff random coils entangle, forming viscoelastic solutions retaining flow without gelling.

Hyaluronan solutions are viscous at low shear rates, but elastic at high shear rates. Hyaluronic acid's molecular structure leads to its viscoelastic property, hydrophilicity, and lubricity. Use of HA in a composite is more durable than heparin surface treatments and coatings. HA is easily produced commercially via fermentation and its availability in high molecular weights results in composites with large, relatively mobile HA molecules at the surface which should enhance antithrombogenicity and permit efficient, cost-effective commercial scale-up. HA is also available in oligomeric forms, which permits tuning to different biological effects than the higher molecular weight species.

HA is known to bind to three different receptors on ECs: CD44, hyaluronan-mediated motility receptor (RHAMM), and toll-like receptor 4 (TLR4). CD44 is a cell-surface glycoprotein involved in cell-cell interactions, cell adhesion and migration. RHAMM normally is localized inside the cell and may be involved in transport channels or proteins, flippase activity, and exocytosis. Intracellularly, RHAMM is associated with microtubules and plays a role in the regulation of mitosis. Extracellularly, RHAMM is associated with CD44, and, upon binding to HA, activates intracellular signaling pathways. TLR4 plays a fundamental role in pathogen recognition and activation of innate immunity, recognizing pathogen-associated molecular patterns expressed on infectious agents, and mediating the production of cytokines necessary to develop effective immunity. ECs show enhanced expression of CD44 and TLR4 under inflamed conditions. The interaction of CD44 receptor with HA has been shown to enhance the production of VEGF and thus promotes cell proliferation. The chain length of HA molecules may significantly affect its interaction with these receptors on ECs. Longer chain HA molecules will most likely have ligands for these receptors which are not as accessible as those on shorter chain HA molecules. HA may also regulate embryonic development, tissue organization, wound healing and angiogenesis.

Salt complexes of hyaluronic acid may be used in forming the composite. Examples of suitable cations include, but are not limited to, alkyltrimethylammonium chloride, alkylamine hydrochloride, alkylpyridinium chloride, alkyldimethylbenzyl ammonium chloride, alkyltrimethylammonium bromide, alkylamine hydrobromide, alkylpyridinium bromide, and alkyldimethylbenzyl ammonium bromide. Optionally, the HA is temporarily protected with a protecting group.

HA may be present in the composite from about 0.001% to about 15% by weight, or 0.2% to about 1.5% by weight. In some embodiments, the HA concentration is from about 0.2% to about 10% by weight, such as about 5% to about 10% by weight, about 0.5% to about 3.5% by weight, about 0.5% to about 1.0% by weight, about 1.0% to about 1.5% by weight, about 1.5% to about 2.0% by weight, about 2.0% to about 2.5% by weight, about 2.5% to about 3.0% by weight, about 3.0% to about 3.5% by weight, about 3.5% to about 4.0% by weight, about 4.0% to about 4.5% by weight, about 4.5% to about 5.0% by weight, about 5.5% to about 6.0% by weight, about 7.0% to about 7.5% by weight, about 7.5% to about 8.0% by weight, about 8.0% to about 8.5% by weight, about 8.5% to about 9.0% by weight, about 9.0% to about 9.5% by weight, or about 9.5% to about 10.0% by weight. In other embodiments, the HA concentration in the composite may be about 0.2%, about 0.3%, about 0.4%, about 0.5%, about 0.6%, about 0.7%, about 0.8%, about 0.9%, about 1.1%, about 1.2%, about 1.3%, about 1.4%, about 1.5%, about 1.6%, about 1.7%, about 1.8%, about 1.9%, or about 2.0%.

The guest molecules are crosslinked to each other within the polymer host. To achieve crosslinkage, crosslinking agents are used, such as carbodimides. In a particular embodiment, the GAG may be crosslinked at the carboxylic acid groups and/or hydroxyl groups using a water-soluble carbodiimide. such as 1-ethyl-3-(3-dimethylaminopropyl) carbodiimide (EDC).

Different sized GAGs, such as cross-linked HA molecules, may induce different signaling mechanisms within an organism. The molecular weight ranges for the cross-linked guest molecules may be varied based on cross-linking conditions and the desired biological effect. In some embodiments, the crosslinked guest molecule may have a large molecular weight, for example from about 10 kDa to about 1 MDa, such as from about 10 kDa to about 50 kDa, from about 50 kDa to about 100 kDa, from about 100 kDa to about 200 kDa, from about 100 kDa to about 200 kDa, from about 100 kDa to about 200 kDa, from about 200 kDa to about 300 kDa, from about 300 kDa to about 400 kDa, from about 400 kDa to about 500 kDa, from about 600 kDa to about 700 kDa, from about 800 kDa to about 900 kDa, or from about 900 kDa to about 1,000 kDa (1 MDa). In other embodiments, the crosslinked guest molecule may have a molecular weight from about 1 kDa to about 15 kDa, for example from about 1 kDa to about 10 kDa, such as from about 1 kDa to about 2 kDa, from about 2 kDa to about 3 kDa, from about 3 kDa to about 4 kDa, from about 4 kDa to about 5 kDa, from about 5 kDa to about 6 kDa, from about 6 kDa to about 7 kDa, from about 7 kDa to about 8 kDa, from about 8 kDa to about 9 kDa, or from about 9 kDa to about 10 kDa. In yet other embodiments, the crosslinked guest molecule may be oligomeric, comprising from about 2 to about 15 monomeric units of guest molecules, for example, 6 units or 12 units. In this embodiment, the molecular weight of the oligomeric crosslinked guest molecule is about 0.75 kDa to about 10 kDa, such as for example about 0.75 Da to 1 kDa, from about 1 kDa to about 2 kDa, from about 2 kDa to about 3 kDa, from about 3 kDa to about 4 kDa, from about 4 kDa to about 5 kDa, from about 5 kDa to about 6 kDa, from about 6 kDa to about 7 kDa, from about 7 kDa to about 8 kDa, from about 8 kDa to about 9 kDa, or from about 9 kDa to about 10 kDa.

(iv) Molding and Printing

The diblock copolymer hydrogel may be shaped via molding or printing. The mold may be cerated by 3D printing a model and then a pair of negative molds cast from the 3D-printed mold. Alternatively, a pair of negative models may be 3D-printed, thereby providing an interior volume defining the size and shape of a medical device.

Alternatively, the diblock copolymer hydrogel may be formed by directly 3D printing in the size and shape of a medical device. A medical device may be customized for a patient and printed using the thermoplastic elastomeric hydrogel materials described herein using a three-dimensional (3D) printer. In one aspect, the cardiovascular medical device may customized for the patient using a patient-specific 3D model generated using patient cardiovascular data and/or a printing profile. The patient-specific 3D model may be sliced into several cross-sections from which print instructions are generated. The print instructions may define the actions of the 3D printer as the customized medical device is manufactured. The customized medical device may include one or more micro-geometries, profiles, shapes, sizes, and/or other features customized for the patient, the physician performing the procedure, and/or the procedure.

(v) Swelling and the Liquid Medium

The SO-SOS glass is contacted with a liquid medium to form a block copolymer hydrogel. If the SO-SOS glass was formed by printing or molding, as described herein, the glass is shaped such that it will be the target size after swelling. That is, the glass may be printed or molded at a volume that is as small as about 10% of the target volume, such as about 20%, about 30%, about 40%, or about 50% of the target volume.

The liquid medium may be an aqueous medium. For example, any liquid medium described herein may be used.

The SO-SOS glass may be contacted with the liquid medium at a temperature above 0° C. and below about 60° C., such as above 0° C. and below about 20° C., or at about 10° C. The temperature may be between about 0° C. and about 5° C., between about 5° C. and about 10° C., between about 10° C. and about 15° C., between about 15° C. and about 20° C., between about 20° C. and about 25° C., between about 25° C. and about 30° C., between about 30° C. and about 35° C., between about 35° C. and about 40° C., between about 40° C. and about 45° C., between about 45°

C. and about 50° C., between about 50° C. and about 55° C., or between about 55° C. and about 60° C.

The SO-SOS glass may be contacted with the aqueous medium at a temperature above 0° C. and below about 60° C., such as above 0° C. and below about 20° C., at about 10° C. The temperature may be between about 0° C. and about 5° C., between about 5° C. and about 10° C., between about 10° C. and about 15° C., between about 15° C. and about 20° C., between about 20° C. and about 25° C., between about 25° C. and about 30° C., between about 30° C. and about 35° C., between about 35° C. and about 40° C., between about 40° C. and about 45° C., between about 45° C. and about 50° C., between about 50° C. and about 55° C., or between about 55° C. and about 60° C.

After swelling, the block copolymer hydrogel may have a liquid concentration between about 32:1 and 2:1 liquid medium/SO-SOS by weight, such as between about 32:1 to 30:1 liquid medium/SO-SOS by weight, between about 30:1 to 28:1 water/SO-SOS by weight, between about 28:1 to 26:1 liquid medium/SO-SOS by weight, between about 26:1 to 24:1 liquid medium/SO-SOS by weight, between about 24:1 to 22:1 liquid medium/SO-SOS by weight, between about 22:1 to 20:1 liquid medium/SO-SOS by weight, between about 20:1 to 18:1 liquid medium/SO-SOS by weight, between about 18:1 to 16:1 liquid medium/SO-SOS by weight, between about 16:1 to 14:1 liquid medium/SO-SOS by weight, between about 14:1 to 12:1 liquid medium/SO-SOS by weight, between about 12:1 to 10:1 liquid medium/SO-SOS by weight, between about 10:1 to 8:1 liquid medium/SO-SOS by weight, between about 8:1 to 6:1 liquid medium/SO-SOS by weight, between about 6:1 to 4:1 liquid medium/SO-SOS by weight, or between about 4:1 to 2:1 liquid medium/SO-SOS by weight. The liquid concentration of the hydrogel may be between about 16:1 and about 4:1 liquid medium/SO-SOS by weight.

After swelling, the block copolymer hydrogel may have a water concentration between about 32:1 and 2:1 water/SO-SOS by weight, such as between about 32:1 to 30:1 water/SO-SOS by weight, between about 30:1 to 28:1 water/SO-SOS by weight, between about 28:1 to 26:1 water/SO-SOS by weight, between about 26:1 to 24:1 water/SO-SOS by weight, between about 24:1 to 22:1 water/SO-SOS by weight, between about 22:1 to 20:1 water/SO-SOS by weight, between about 20:1 to 18:1 water/SO-SOS by weight, between about 18:1 to 16:1 water/SO-SOS by weight, between about 16:1 to 14:1 water/SO-SOS by weight, between about 14:1 to 12:1 water/SO-SOS by weight, between about 12:1 to 10:1 water/SO-SOS by weight, between about 10:1 to 8:1 water/SO-SOS by weight, between about 8:1 to 6:1 water/SO-SOS by weight, between about 6:1 to 4:1 water/SO-SOS by weight, or between about 4:1 to 2:1 water/SO-SOS by weight. The water concentration of the hydrogel may be between about 16:1 and about 4:1 water/SO-SOS by weight.

The block copolymer hydrogel having a fatigue resistance to at least 500,000 compression cycles, such as at least 600,000 compression cycles, such as at least 700,000 compression cycles, such as at least 800,000 compression cycles, such as at least 900,000 compression cycles, such as at least 1,000,000 compression cycles, such as at least 1,500,000 compression cycles, such as at least 2,000,000 compression cycles, such as at least 2,500,000 compression cycles, such as at least 3,000,000 compression cycles, such as at least 3,500,000 compression cycles, such as at least 4,000,000 compression cycles, such as at least 4,500,000 compression cycles, such as at least 5,000,000 compression cycles, or such as at least 10,000,000 compression cycles. In counting the number of compression cycles, the cycles are preferably continuous, but need not be so, having a resting period between shorter runs of cycles.

The compression cycles may operate with at least 12% compression at a frequency of about 1 Hz, particularly wherein the compression cycles operate with 50% compression at least every eleventh cycle. The fatigue resistance is characterized by a modulus recoverable to at least 80% of its value before the compression cycles were run, such as to at least 90%, to at least 92%, to at least 95% or to at least 98% of its value before the compression cycles were run.

(vi) Sutures, Directional Fibers, and Photopatterning

The soft tissue mimetics described herein may implanted into the body of patient in need thereof using one or more fasteners for tissue fixation known in the art. Suitable fasteners include, but are not limited to, an anchor, screw, bolt, corkscrew, suture, tissue retainer, suture lock, knotless suture lock, suture chain, knotless interface, stress isolator, and combinations thereof. Suitable anchors include, but are not limited to, a bone anchor, suture anchor, corkscrew suture anchor, perforated suture anchor, push-in suture anchor, fenestrated suture anchor, threaded anchor, and combinations thereof. A variety of soft tissue bone fixation devices may be employed, especially when the soft tissue mimetic replaces a connective tissue, such as a tendon or ligament which needs to be securely affixed to a bone. In some embodiments, the soft tissue mimetic may be implanted using a configuration similar to one depicted at FIGS. 71-74, described herein.

The soft tissue mimetics may include directional fibers disposed within the hydrogel. When present, these fibers modify the moduli of the material in the direction in which the fiber lies. For example, a directional fiber in the lateral direction modifies a modulus in the lateral direction, and a direction fiber radially disposed within the hydrogel modifies a modulus in the radial dimension. In particular embodiments, the directional fibers may by polyamide sutures, with or without surface modifications, such as a methylmethacrylate (MMA) or methyl acrylate or hyaluronic acid coating. The directional fibers may extend beyond the hydrogel, thereby providing sutures for implantation into the body of a patient in need thereof. In particular, the directional fibers may be connected to a suture anchor.

Alternatively or in addition to other modifications described herein, a combination of masks and temperature changes may be used to controllably photopattern hyaluronic acid onto the surface of the block copolymer hydrogel (Example 26 below). Such surface treatment, however, is not required.

Definitions

As used herein, the terms "about" and "approximately" designate that a value is within a statistically meaningful range. Such a range can be typically within 20%, more typically still within 10%, and even more typically within 5% of a given value or range. The allowable variation encompassed by the terms "about" and "approximately" depends on the particular system under study and can be readily appreciated by one of ordinary skill in the art.

As used herein, the term "w/w" designates the phrase "by weight" and describes the concentration of a particular substance in a mixture or solution.

As used herein, the term "ml/kg" designates milliliters of composition per kilogram of formula weight.

As used herein, the term "monomer" refers to any chemical compound capable of forming a covalent bond with itself or a chemically different compound in a repetitive manner. The repetitive bond formation between monomers may lead to a linear, branched, super-branched, or three-dimensional product. Furthermore, monomers may themselves comprise repetitive building blocks, and when polymerized the polymers formed from such monomers are then termed "block polymers." Monomers may belong to various chemical classes of molecules including organic, organometallic or inorganic molecules. The molecular weight of monomers may vary greatly between about 40 Daltons and 20000 Daltons. However, especially when monomers comprise repetitive building blocks, monomers may have even higher molecular weights. Monomers may also include additional reactive groups.

Contemplated polymers may also comprise a wide range of functional or structural moieties, including aromatic systems, and halogenated groups. Furthermore, appropriate polymers may have many configurations, including a homopolymer, and a heteropolymer. Moreover, alternative polymers may have various forms, such as linear, branched, super-branched, or three-dimensional. The molecular weight of contemplated polymers spans a wide range, typically between 400 Daltons and 400,000 Daltons, and may be greater than 1,000,000 Daltons or more, in some embodiments.

"Wettability" refers to the ability of a liquid, such as water, to spread on a solid surface. "Hydrophilic" and "hygrophilic" refer to an intrinsic or average chemical property of a surface or bulk solid to allow a polar liquid, such as water, to spread on the surface, with typical water contact angles from about 0° to about 90°. "Hydrophobic" refers to an intrinsic or average chemical property of a surface or bulk solid that prevents a polar liquid, such as water, from spreading on the surface, with typical water contact angles from about 90° to about 180°, such as from about 100° to about 150°. When the surface roughness enhances or reduces the hydrophilic or hydrophobic properties of a surface or bulk solid, the effect is "parahydrophilic" or "parahydrophobic," respectively. For very rough surfaces, the enhancement or reduction in hydrophilic or hydrophobic properties of the surface or bulk solid may be very great; the effect is referred to as "superhydrophilic" or "superhydrophobic," respectively. Surface roughness is usually defined on the microscopic or molecular scales. For further definition of wettability and surface classifications, please refer to Marmur, "Hydro-hygro-oleo-omni-phobic? Terminology of wettability classification," *Soft Matter*, 8:6867 (2012), which is incorporated herein by reference in its entirety.

The compounds described herein have asymmetric centers. Compounds of the present disclosure containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

When introducing elements of the present disclosure or the preferred embodiments(s) thereof, the articles "a", "an", "the" and "said" are intended to mean that there are one or more of the elements. The terms "comprising," "including," and "having" are intended to be inclusive and mean that there may be additional elements other than the listed elements.

Having described several embodiments, it will be recognized by those skilled in the art that various modifications, alternative constructions, and equivalents may be used without departing from the spirit of the disclosure. Additionally, a number of well-known processes and elements have not been described in order to avoid unnecessarily obscuring the embodiments disclosed herein. Accordingly, the above description should not be taken as limiting the scope of the document.

EXAMPLES

The following examples are included to demonstrate certain embodiments of the disclosure. It should be appreciated by those of skill in the art that the techniques disclosed in the examples represent techniques discovered by the inventors to function well in the practice of the disclosure. Those of skill in the art should, however, in light of the present disclosure, appreciate that many changes can be made in the specific embodiments that are disclosed and still obtain a like or similar result without departing from the spirit and scope of the disclosure, therefore all matter set forth is to be interpreted as illustrative and not in a limiting sense.

Example 1—Synthesis of Hydroxy-polystyrene ("S—OH")

Purified styrene monomer (120 g, 1.14 mol, 20° C.) was added to a stirring solution of sec-butyl lithium (10.23 mL, 1.3 M in cyclohexane) and dry, air-free cyclohexane (1 L, 20° C.) in a 2-L reaction vessel. The temperature was then raised to 40° C. and stirred continuously for 8 hours. At a reduced pressure of 1 psig, purified ethylene oxide (6.6 g, 0.15 mol, 0° C., liquid) was added to the reaction vessel. The reaction was held at 40° C. for an additional 24 hours, after which excess ethylene oxide was removed from the reactor under constant argon flow. The reaction was terminated by adding methanol (50 mL). The polymer was precipitated in methanol (5 L total), producing a fluffy white solid, and dried under vacuum at room temperature for 48 h (yield 116 g, 97%, $M_n$=8064 g/mol, PDI=1.03).

Example 2—Synthesis of Polycyclohexylethylene ("PCHE")

Hydroxy-polystyrene (S—OH, 5.0 g) from Example 1 was dissolved in 180 mL of purified cyclohexane in a high-pressure vessel and degassed by bubbling argon through the solution for about 20 minutes. The catalyst was palladium on calcium carbonate ($CaCO_3$, Aldrich, 12.5 g, 2.5:1 catalyst to S—OH-by weight). The reaction mixture was sealed in a high-pressure reactor. The catalyst was placed under vacuum at 100° C. overnight, then activated with 100 psig hydrogen gas ($H_2$) for at least 1 hour at 100° C. The reactor was vented and backfilled three times with argon and left under a positive pressure of argon at 100° C. The S—OH solution was transferred to the sealed reactor, the pressure reduced, and the temperature increased to 120° C. while stirring at about 1500 rpm. The reactor was initially charged with 500 psig $H_2$, and recharged to 500 psig $H_2$ several times while the reaction proceeded overnight. The catalyst was removed by filtration. The polymer product was precipitated into 1 liter methanol, collected by vacuum filtration, and dried at elevated temperature at about 150° C. under a vacuum for 24 hours. The reaction produced polycyclohexylethylene (PCHE). Instead of Pd/$CaCO_3$, another hydrogenation catalyst may be selected, for example Dow Hydrogenation Catalyst (DHC, 5 wt % Pt supported on wide-pore silica).

Example 3—Synthesis of hydroxy-polystyrene-b-poly(ethylene Oxide) ("SO")

Figure 2:
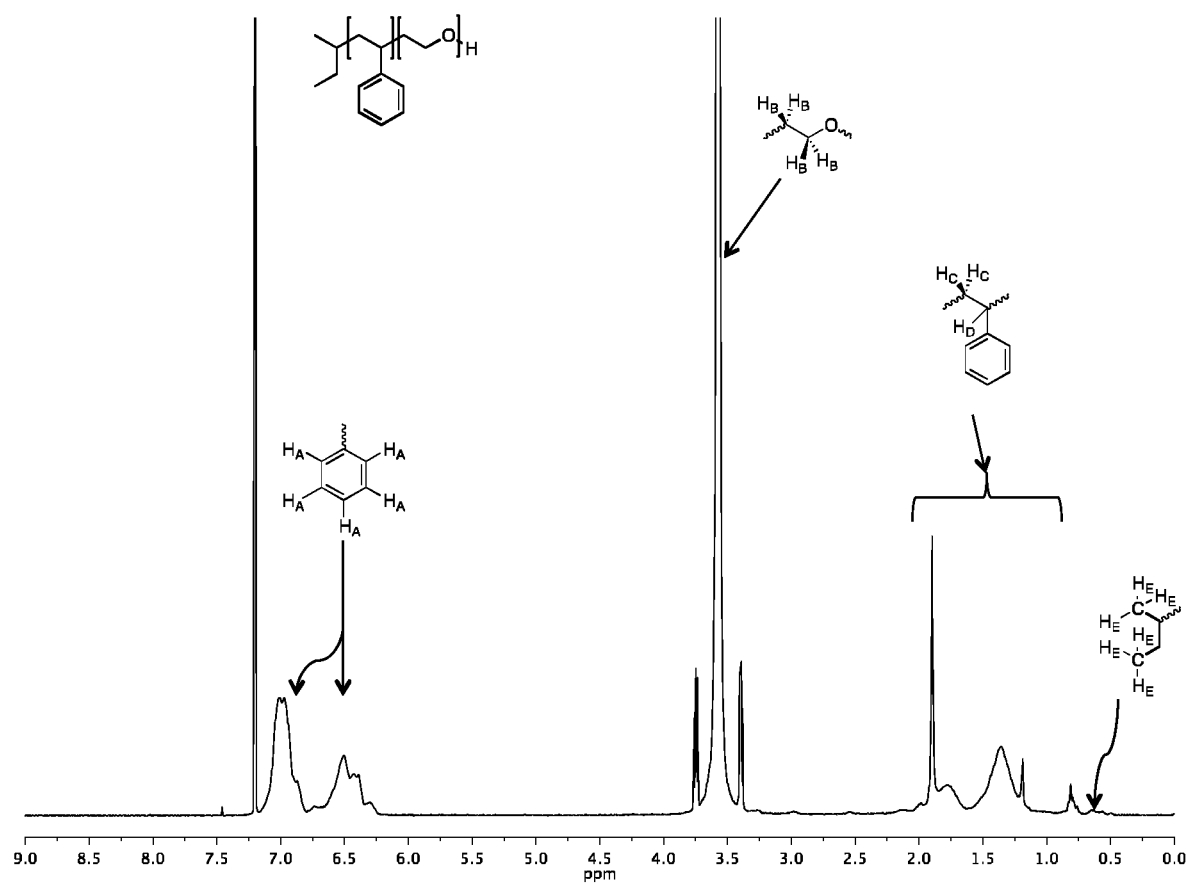
FIG. 2. $^1$H-NMR spectrum of PS-PEO-H diblock copolymer. The PS-PEO-PS triblock copolymer, PS-PEO-azide diblock copolymer, and PS-PEO-alkyne diblock copolymer were all generated from a SO diblock copolymer molecule.

Hydroxy-polystyrene (S—OH, 7 g, 1.14 mol) form Example 1 was added to a 2-L reaction vessel containing a glass-coated magnetic stir bar. The reactor was evacuated and backfilled with purified argon (5×) before adding 1 L dry, air-free tetrahydrofuran (THF). Concentrated potassium naphthalenide in THF was added to the polymer solution via cannula until a light green color persisted for 30 minutes. The temperature of the reaction mixture was raised to 40° C. and purified ethylene oxide monomer (78.7 g, 1.78 mol, 0° C.) was added under argon (1 psi) to the stirring solution for 48 hours. The reaction was terminated by methanol (50 mL) and the polymer was precipitated in pentane (4 L), producing a fluffy white solid. The polymer was dried under vacuum at room temperature for 48 hours. The $^1$H-NMR spectrum of hydroxy-polystyrene-b-poly(ethylene oxide) ("PS-PEO diblock copolymer," "PS-PEO-H," or "SO") is shown at FIG. 2. ($M_n$=70,000 g/mol, PDI=1.04). This reaction may also be performed with polycyclohexylethylene (PCHE) from Example 2.

Example 4—Synthesis of polystyrene-b-poly(ethylene oxide)-b-polystyrene ("PS-PEO-PS," "SOS") Triblock Copolymer Hydroxyl-terminated PS-PEO diblock copolymer (SO) is the parent molecule from which the remaining three block copolymers were derived. SO was prepared via the two-step anionic polymerization of styrene and ethylene oxide described about at Example 2. From this parent diblock copolymer the first of the three derivative molecules, an PS-PEO-PS (SOS) triblock copolymer was synthesized by re-activating the terminal alcohol on SO with potassium naphthalenide and adding α,α'-dibromo-p-xylene over several hours.

Specifically, SO diblock (29 g) from Example 3 was placed into a 2-L round-bottomed reactor. Atmospheric water and oxygen were removed through five successive argon-vacuum backfills with argon pressures reaching 5 psig and vacuum pressures reaching 8-10 mTorr. The SO diblock was allowed to dry under vacuum in the 2-L reactor overnight at 8-10 mTorr. The SO diblock was then dissolved in dry THF. A concentrated potassium naphthalenide solution in dry THF was titrated into the reactor until the solution maintained a green color for 30 minutes.

α,α'-Dibromo-p-xylene in THF (1.5 mL) at a 0.5 molar equivalent to the SO—OH was then injected into the reactor over 12 hours at 0.125 mL/hour using a syringe pump and a 2.5-mL glass syringe. Coupled polymer was precipitated in 5 L pentane followed by vacuum filtration. The precipitated polymer was dried overnight under vacuum to produce a fluffy white solid.

The coupled triblock copolymer product was found to be a 60:40 (mass %) mixture of SOS:SO via SEC peak integration. The SOS triblock copolymer was isolated from this mixture (98+%) via iterative fractionation with chloroform and n-hexane. The temperature was maintained above 40° C. to avoid (non)solvent-induced PEO crystallization. The SOS triblock copolymer ad a molecular weight and contour length essentially double that of the SO diblock copolymers, thereby ensuring domain size compatibility (lattice matching) between the SO and SOS block copolymers during self-assembly.

$^1$H-NMR confirmed the targeted volume fraction of polystyrene ($f_S$=0.13), and SEC confirmed the narrow polydispersity of 1.04. A molecular weight ($M_{n,SO}$) of 70,000 kDa was determined using the SEC determined S—OH $M_n$ value of 8390 kDa (PS stds), in combination with the relative block compositions determined using the S—OH $^1$H-NMR peak integrations. SEC: (THF, PS stds): S—OH: $M_{n,S—OH}$=8390 g mol$^{-1}$, $M_w/M_n$=1.03; S—OH: $M_{n,SO}$=70, 000 g mol$^{-1}$ (calculated using $M_{n,S-OH}$ (SEC) and S—OH $^1$H NMR), $M_w/M_n$=1.04; SOS: $M_{n,SOS}$=140,000 g mol$^{-1}$ (determined from $2M_{n,SO}$), $M_w/M_n$=1.06; $^1$H NMR (S—OH, SOS): $\delta_H$ (300 MHz; CDCl$_3$): 6.20-7.26 (b, —C$_6$H$_5$, —OCH$_2$(C$_6$H$_4$)CH$_2$O—), 4.55 (s, —OCH$_2$(C$_6$H$_4$) CH$_2$O—), 3.1-4.0 (b, —CH$_2$CH$_2$O—, —CH(C$_6$H$_5$) CH$_2$CH$_2$O—), 1.0-2.30 (b, —CH$_2$CH(C$_6$H$_5$)—, CH$_3$CH (CH$_2$CH$_3$)—, —CH(C$_6$H$_5$)CH$_2$CH$_2$O—), 0.5-0.78 (m, CH$_3$CH(CH$_2$CH$_3$)—).

This reaction may also be performed with SO diblock copolymer from Example 3 using polycyclohexylethylene (PCHE).

Example 5—Fractionation of the SO/SOS Crude Product

SO/SOS polymer recovered from the coupling reaction described at Example 3 produced a coupling efficiency of 52 mol %. Fractionation achieved higher SOS triblock copolymer content (52-87 mol %).

Dry SO/SOS polymer (4 g) was dissolved in chloroform (400 ml) and heated to 45° C. n-hexane (920 ml) was added slowly, keeping the temperature above 40° C. The SOS triblock copolymer precipitated and the solution turned cloudy. Upon cooling to room temperature, the solution turned transparent. The solution contained the majority of the SO diblock copolymer while the SOS triblock copolymer existed as a precipitate which was vacuum filtered. The SOS triblock precipitate was recovered and allowed to dry under vacuum overnight, while the SO diblock in solution was recovered through rotary evaporation. Different SOS mol % triblock copolymers were achieved through successive fractionations of precipitated SOS copolymers to achieve increasing mol % SOS triblock copolymers.

Example 6—SOS Triblock Copolymer mol % Calculations from GPC Plots

Figure 3:
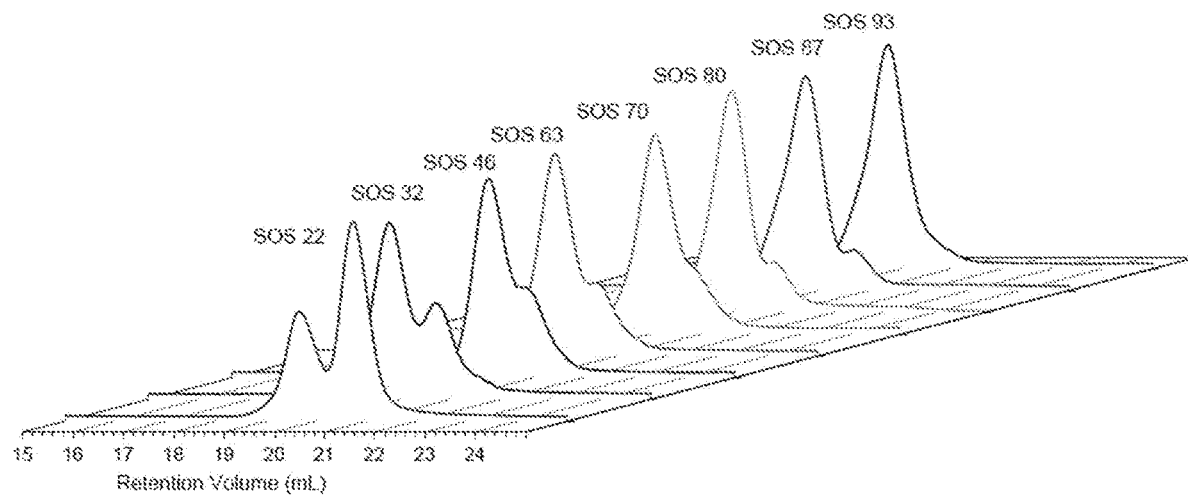
FIG. 3. Size Exclusion Chromatography (SEC) of dry polymer blends of polystyrene-poly(ethylene oxide) diblock copolymer ("SO") and polystyrene-poly(ethylene oxide)-polystyrene ("SOS") triblock copolymer. SEC confirmed the ability to produce various mol % blends of SOS and SO block copolymers from 22 mol % SOS to 93 mol % SOS. All runs were normalized by total area to compare relative mass % of SOS and SO. The peak positions of the retention volume corresponded to SOS (left) and SO (right).

The fractionated SOS triblock copolymer product of Example 5 was separated using gel permeation chromatography (GPC) was performed with three columns in series with THF as a solvent. The SO and SOS peaks were merged (FIG. 3); therefore, the mol % values were calculated using the multiple peak fit function on Origin 9.1. The integrations for each peak showed the relative mass percent of each component. Using the known molecular weights of the SO diblock and SOS triblock copolymers, from $^1$H-NMR, the mol % were calculated (Equation 1).

$$\text{Mol\% SOS} = \frac{\frac{\int \text{Peak}_1}{2}}{\frac{\int \text{Peak}_1}{2} + \int \text{Peak}_2} \qquad \text{(Equation 1)}$$

Example 7—Polymer Disk Formation and Characterization (a) Preparation of Dry SOS Triblock/SO Diblock Copolymer Disks Dry polymer for the five different SOS triblock copolymer content blends (22-87 mol %) were placed into a steel circular washer (8 mm×0.83 mm thick) and sandwiched between two sheets of Teflon™. Or uniform disks (8 mm diameter, 0.24-0.28 mm thickness, 0.015-0.016 g) at each SOS composition were prepared via melt pressing at 150° C. for five minutes using a washer between Teflon™ covered Kapton™ sheets on a Carver press. Melt pressing molded the powders into a homogeneous solid and provides the chain mobility needed for self-assembly into the sphere-based morphology. Samples were removed and allowed to cool to room temperature for swelling.

Adding "lattice matched" SOS triblock copolymer produced a primary scattering peak at a nearly identical principal wave vector, although the regularity of the body-centered cubic (BCC) lattice devolved into a liquid-like packing (LLP) of spheres. Retaining the BCC lattice was not needed for hydrogel formation.

(b) SAXS Data

SAXS data were collected on a Rigaku S-Max 3000 High Brilliance 3 Pinhole SAXS system outfitted with a Micro-Max-007HFM Rotating Anode (CuKα), Confocal Max-Flux™ Optic, Gabriel Multiwire Area Detector and a Linkham thermal stage. Polymer disks were mounted on the thermal stage and heated to 120° C., then cooled down to 100° C. and kept in vacuum for 120 minutes before exposure.

SAXS data for systems adopting a LLP of spheres can be fit to a Percus-Yevick hard sphere model adapted for polydisperse systems. From those fits, PS core diameters and aggregation numbers for an average spherical domain can be determined. Scattering data was consistent with PS core diameters of about 19 nm with about 230 block copolymer chains per sphere. These extracted values approximate those in the BBC lattice of the neat S—OH. That is, adding triblock copolymer, while disruptive to the BCC lattice, does not significantly influence the structure of spherical PS aggregates themselves. SEC analysis of samples before and after melt pressing showed no observable sample degradation or change in SOS content.

(c) Swelling Analysis of High SOS Triblock Copolymer Content Hydrogels

Dry polymer disks were all massed prior to swelling and were then allowed to equilibrate in DI water for 24 hours. Once swollen, the gels were removed from the water and gently patted dry with a Kimwipe™ to remove excess water. Water content within gels was determined gravimetrically (g water/g polymer) at three temperatures (10, 22, and 37° C.). The solutions for swelling were brought to the appropriate temperature using a temperature controlled water bath or oil bath for cooling and heating respectively. Water absorption was calculated by the difference of the mass of the swollen gel and dry polymer disk divided by the mass of the dry polymer.

Figure 4:
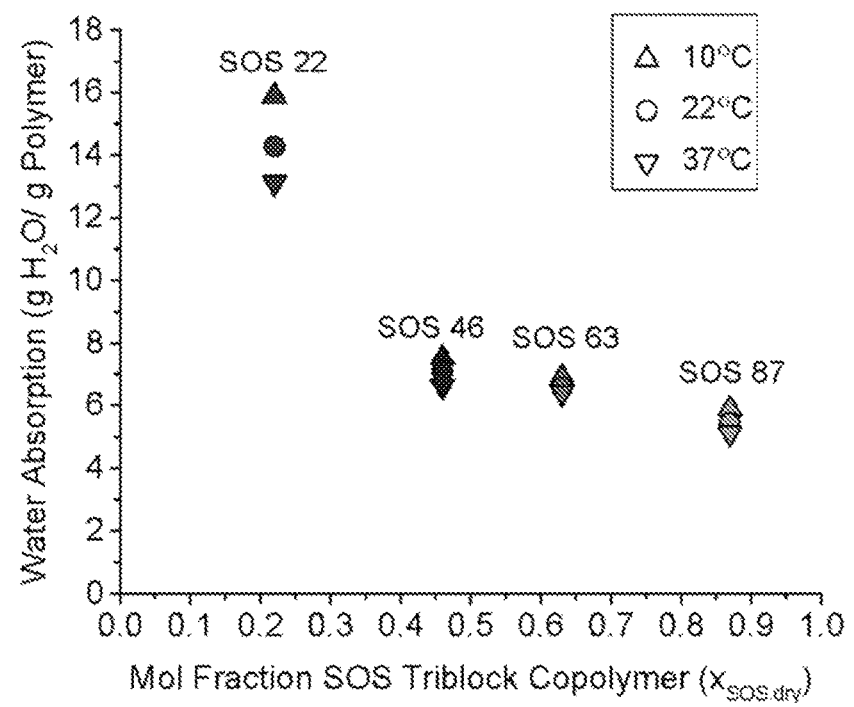
FIG. 4. Water absorption versus mol fraction SOS.

Cooler temperatures (10° C.) resulted in higher swelling ratios, whereas warmer temperatures (37° C.) resulted in a lower swelling ratio. As triblock copolymer content increased, the swelling ratio decreased, with little effect after 46 mol % as seen in FIG. 4.

Two competing forces determined the swelling dimensions of the hydrogel: the osmotic driving force of the water, and the entropic restoring force of the tethering PEO midblock. As temperature increased, the osmotic driving force diminished, resulting in lower water absorption. Higher temperatures also reduced the solubility of the PEO matrix in water. Triblock copolymer content affected swelling by increasing tethers between spheres, resulting in the hydrogel's restricted ability to imbibe water. Overall, the hydrogels swelled isotropically.

Figure 66:
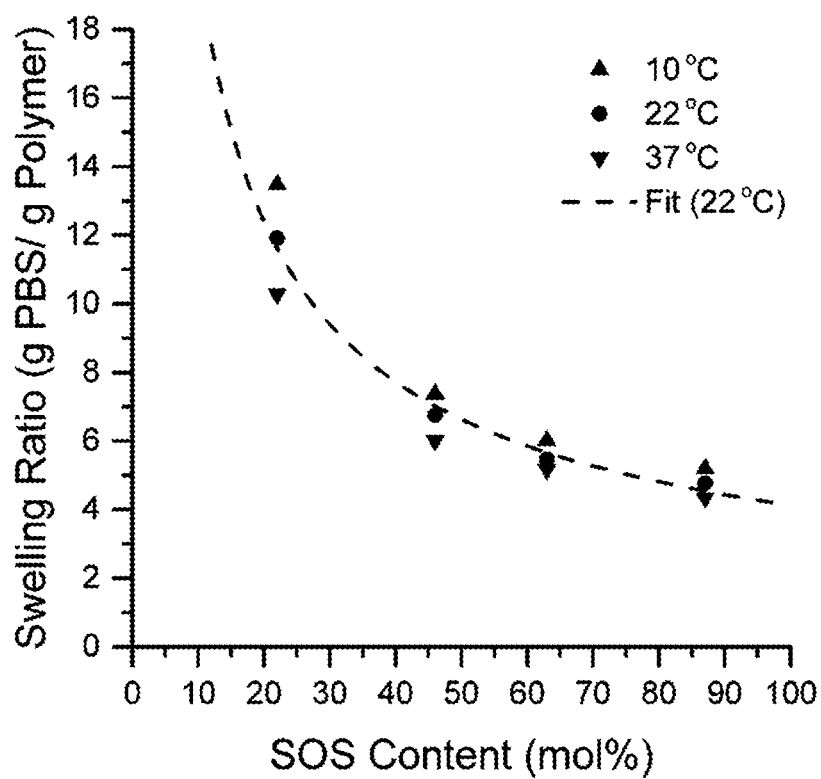
FIG. 66. Gravimetrically determined swelling ratio data in phosphate-buffered saline (PBS) for SOS22, SOS46, SOS63, and SOS87 at 10° C., 22° C., and 37° C. with an approximate power fit (95.6(SOS mol %)$^{-0.682}$, $R^2$=0.99).

The swelling measurements were repeated for hydrogels prepared in phosphate-buffered saline (PBS). FIG. 66 shows gravimetrically determined swelling ratio data in PBS for SOS22, SOS46, SOS63, and SOS87 at 10° C., 22° C., and 37° C. with an approximate power fit (95.6(SOS mol %))$^{-0.682}$, $R^2$=0.99). As SOS content increased, the swelling ratio decreased accordingly. This effect may be partially due to an increase in the number of connections between spherical domains as SOS content increased. The higher SOS content increased the number of trapped topological entanglements produced in the melt, resulting in a restricted ability of the hydrogel to imbibe PBS. The lower swelling ratio at higher temperatures may be due to the reduced solubility of the PEO matrix as temperature increased.

Example 8—Indentation Relaxation Testing of Swollen Hydrogels

Specimens were prepared according to Example 7 and were kept hydrated in DI water before and during indentation relaxation tests, which were run on a servo hydraulic test system (Bionic Model 370.02 MTS Corp, Eden Prairie, Minn.). The water bath containing the sample was attached to a multi-degree of freedom camera mount, and an x-y plate fixture allowing for the indentation surface to be oriented normal to the indenter and centered on the specimen, respectively. A spherical tip with a diameter of 1.59 mm was used as an indenter, and loads were recorded using a 908 g load cell (Futek™ LSB200, Irvine, Calif.). Because compressive properties are time dependent, both equilibrium and instantaneous moduli were computed.

All samples were preloaded to 2 g, and preliminary tests determined a relaxation time of 300 seconds resulted in equilibrium conditions. Specimens were indented to a strain of 12%/sec. Hertzian contact (Equation 2) was applied and used to determine both the instantaneous and equilibrium moduli. The contact equation assumed contact between an elastic half space and a sphere where F is the force, R is the radius of the indenter, d is the indentation depth, $E_1$ and $\upsilon_1$ are the elastic modulus and Poisson's ratio of the hydrogel respectively, and likewise $E_2$ and $\upsilon_2$ are the elastic modulus and Poisson's ratio of the indenter. The indenter tip had an elastic modulus and a Poisson's ratio of 210 GPa and 0.3, respectively. The elastic modulus of the hydrogel was calculated from unconfined compression testing while the Poisson's ratio of the hydrogel was approximated to be 0.5 in this small strain regime.

$$E_1 = \frac{(1-\upsilon_1)^2}{\left(\frac{3F}{4R^{\frac{1}{2}}d^{\frac{3}{2}}}\right) - \left(\frac{(1-\upsilon_2)^2}{E_2}\right)}$$ (Equation 2)

Figure 5:
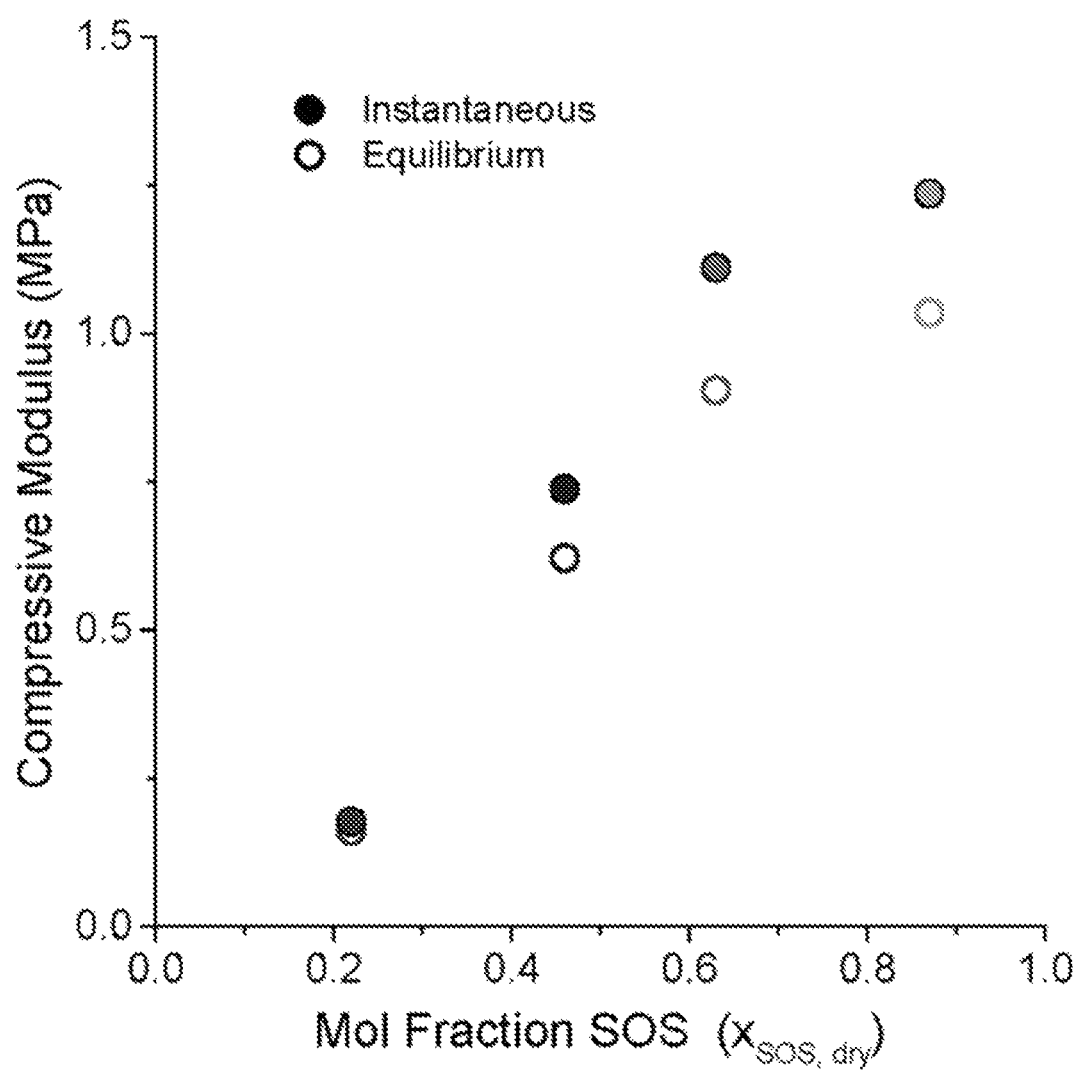
FIG. 5. Indentation relaxation testing of hydrogels swollen in deionized (DI) water showing the dependence of both instantaneous and equilibrium compressive modulus on SOS content of four distinct SOS blends. (Filled circles: instantaneous compressive modulus, unfilled circles: equilibrium compressive modulus).

Indentation testing was performed on four hydrogel blends to develop a complete picture of osmotic movement during compression and its effect on mechanical properties, as seen at FIG. 5. In indentation testing of hydrated materials, this was an effect of instantaneous modulus—attributed to trapped water generating a reactionary force—followed by an equilibrium modulus after the material "relaxes," or water has sufficient time to move from the indentation site.

The equilibrium moduli were 14.9±5.3% lower than the instantaneous moduli, implying a significant effect of water movement on modulus. Testing showed increasing SOS content increased both the instantaneous and equilibrium modulus in indentation. This increase in compressive modulus in higher triblock systems was largely due to more coronal overlap of the micelles. As the triblock copolymer content increased, the physical crosslinks between micelles increased, which increased topological entanglements, limited micellar separation, increased coronal overlap, and stiffened the material. The increased topological entanglements in higher SOS content hydrogels yielded a greater relaxation in modulus due to an increased restriction to fluid flow producing a higher relative instantaneous force, as seen at FIG. 6.

Figure 67:
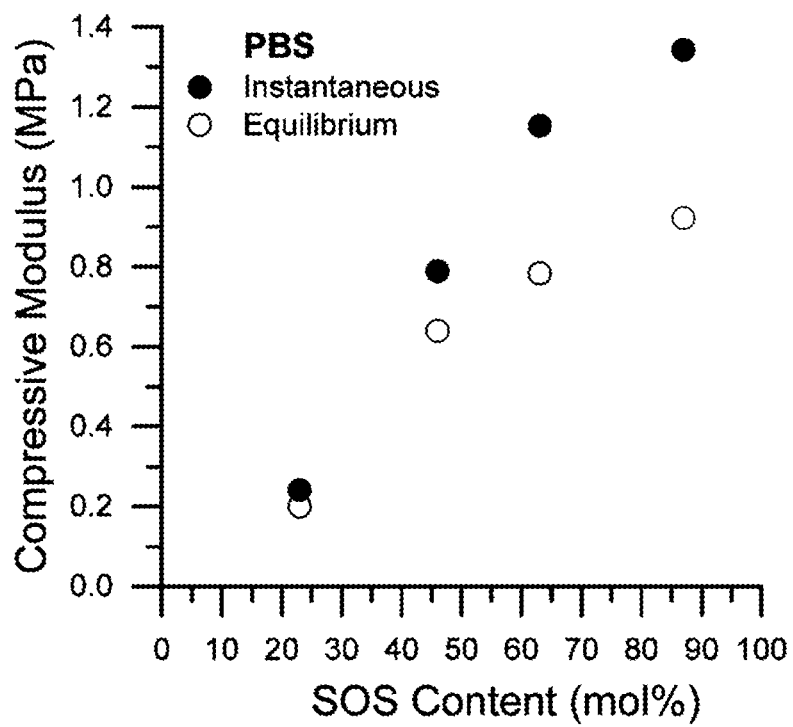
FIG. 67. Indentation relaxation data for SOS22, SOS46, SOS63, and SOS87 in phosphate-buffered saline (PBS) at room temperature.

Indentation measurements were also taken for hydrogels prepared in phosphate-buffered saline (PBS). FIG. 67 shows indentation relaxation data for SOS22, SOS46, SOS63, and SOS87 in PBS at room temperature. All samples were strained to 12% in 1 second and allowed to relax for 300 seconds. Hertzian contact was applied to determine the instantaneous and equilibrium moduli. As SOS content increased, the instantaneous and equilibrium moduli increased, largely due to increased coronal overlap between adjacent micelles. As the SOS content increased, the chain density also increased, leading to a higher resistance to poroelastic flow. Thus, the initial modulus temporarily increased under a constant load but eventually relaxed once mechanically induced flow was initiated.

Example 9—Tensile Testing of Swollen Hydrogels

Tensile testing was performed on specimens from Example 7 on an ARES-rheometer (TA instruments, DE) at room temperature. Gels were swollen as disks and cut into strips for tensile testing. The strips were 3 mm wide, 8 mm long, and 0.8 mm thick. The strips were placed into torsion rectangular grips (TA Instruments, DE) with a layer of sandpaper between the grip and the gel to reduce slippage. The gels were clamped and pulled at a force of 5 g to ensure the gel was taut. The gel was then extended to a mid-substance failure at a strain rate of 2%/sec. Once the mean strain at break ($\lambda_f$) was determined, new samples of the same size were strained in intervals of 20% to $\lambda_f$. Samples were strained then returned to unstrained conditions (i.e. 0-20-0-40-0-60 . . . % $\lambda_f$, etc.) at a strain rate of 2%/sec.

Figure 7:
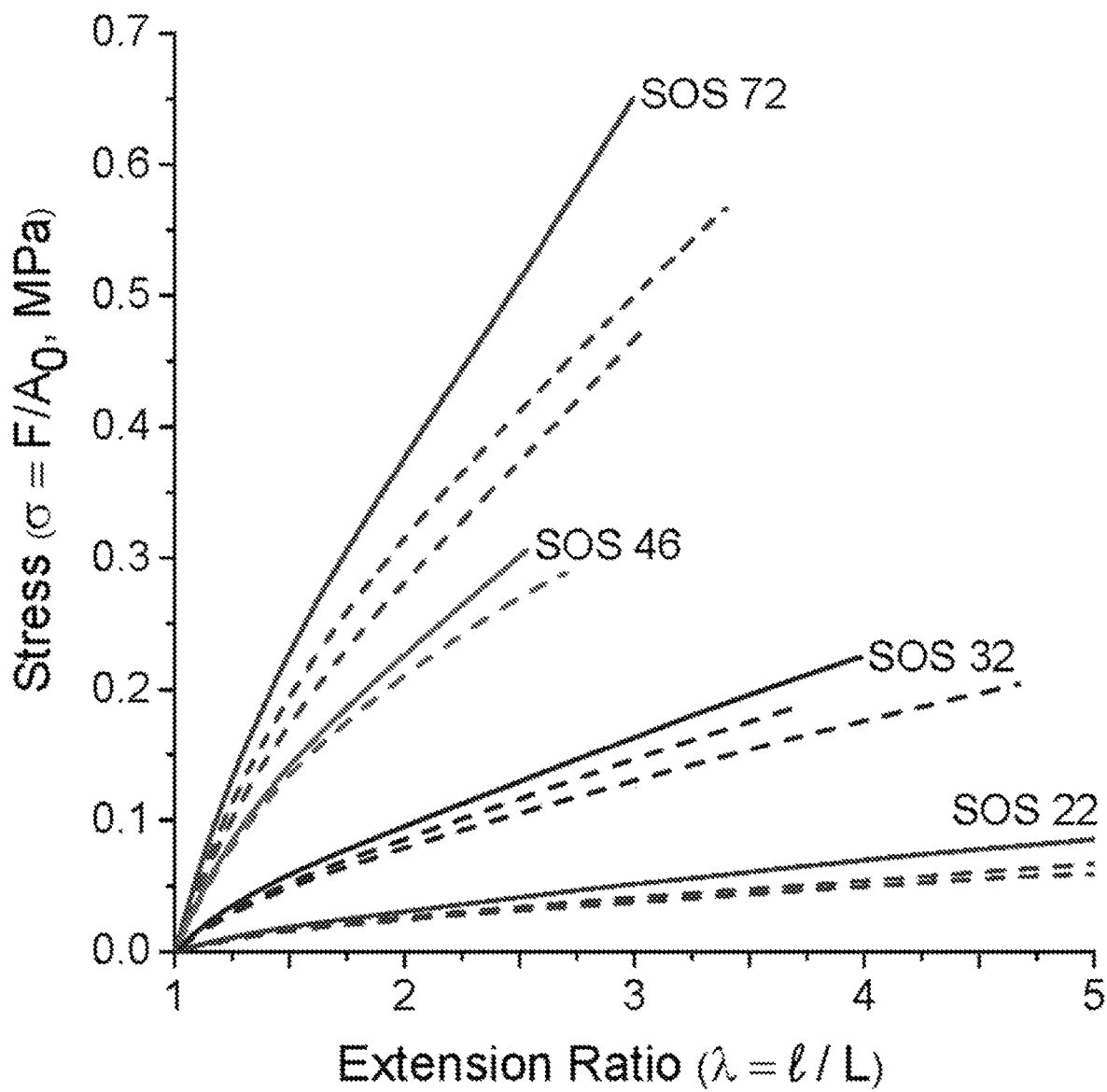
FIG. 7. Ultimate tensile testing showing the relationship of tensile stress (kPa) and Extension ratio of various SOS blends. All samples were pulled to failure at a strain rate of 2%/sec. (Solid line indicates highest modulus run for clarity of the effect of SOS on modulus).

As the SOS content increased, the hydrogels demonstrated a higher tensile modulus and a lower strain at break (FIG. 7). The fixed junction points increased, shifting from dynamic entanglements to greater topological entanglements and increased coronal overlap. The extension ratio no longer decreases after 46 mol % SOS as SOS content increases, but the modulus continues to increase with increased triblock. The very slight increase in extension ratio between 46 and 72 mol % suggested that the distance between styrene spheres have reached a set distance between one another while topological entanglements increase. Further proof of this shift from dynamic to topological entanglements is supported by the swelling ratios being very similar in hydrogels higher than 46 mol %.

Figure 8:
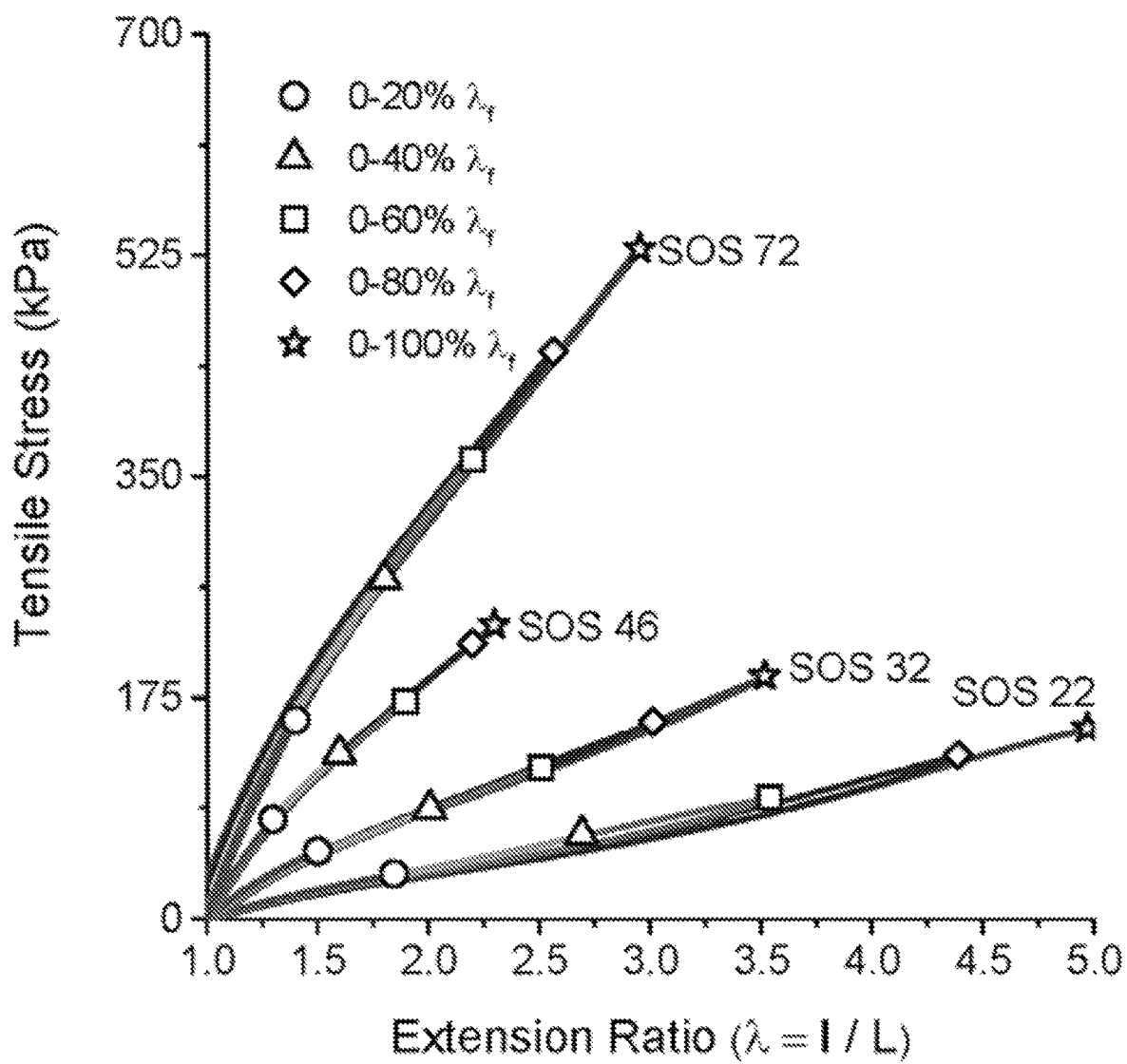
FIG. 8. Loading in interval of mean extension at break in tension showing the relationship of tensile stress (kPa) and extension ratio and hysteresis of swollen hydrogels of different SOS mol %. All samples were pulled in intervals of 20% of the mean extension at failure ($\lambda_f$) at a strain rate of 2%/sec to the full mean extension at failure (i.e. 0-20-0-40-0-60- . . . % of mean extension at failure).

The stress-strain profile of these same samples loaded in successive intervals of 20% up to the mean break at failure ($\lambda_f$) revealed virtually no observable hysteresis or fatigue from one loading interval to the next (FIG. 8). This result suggested recoverable modulus and fatigue resistance, unlike the permanent fractures to the primary network in DN hydrogels and the permanent hysteresis in DN hydrogels seen even at low strain rates.

Without wishing to be bound by theory, the hydrogels disclosed herein performed as they do because of how they absorb energy. The topological and dynamic entanglements—as opposed to the highly concentrated fixed entanglements in DN primary networks—allowed for recoverable energy absorption through repeated SO free chain ends and sliding topological entanglements of SOS chains. This testing revealed a high degree of tunability and elasticity. Generally, failure under tensile loading strongly correlated to fracture initiated at local defects, just like in many elastic polymers, including biological tissues.

Example 10—Shear Testing of Swollen Hydrogels

Hydrogels were prepared according to Example 7 and were shear tested on an ARES-rheometer (TA Instruments, DE) using an 8-mm diameter compression tip at room temperature (~22° C.). Swollen hydrogels were removed from water and excess water was blotted away. Hydrogels were centered on a 50-mm stainless steel flat plate and compressed until 2 g of normal force was measured on the instrument to ensure contact of the force transducer with the gels. Dynamic frequency sweeps (oscillatory shear) were performed for each sample using 0.5% shear strain over a frequency range of 0.1-10 radians/sec. Slip was minimized by placing each sample under a fixed 10% compressive strain throughout the experiment.

Figure 9:
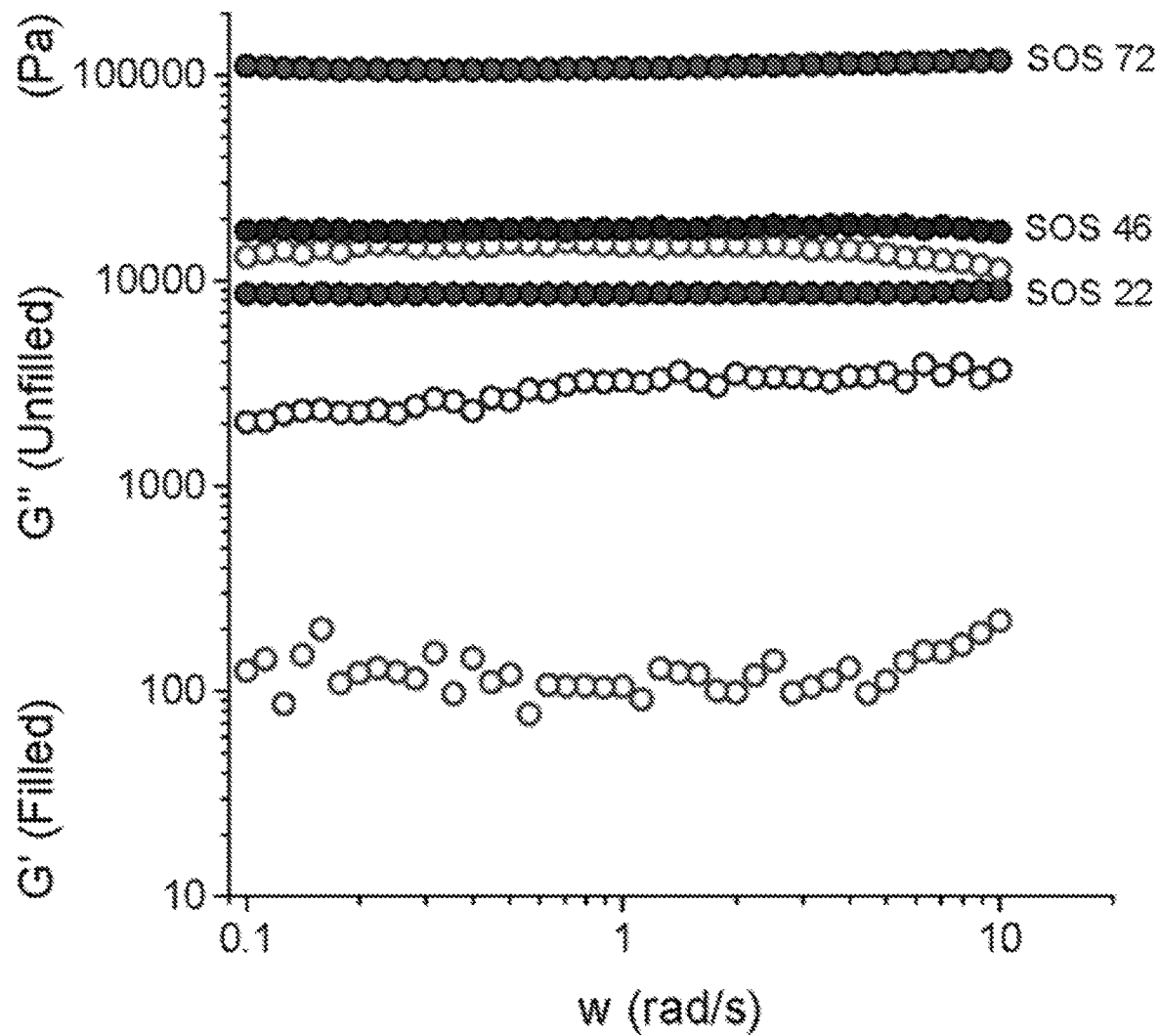
FIG. 9. Frequency sweep of 22, 46, and 72 mol % SOS hydrogels under oscillatory shear at 0.7% strain. All samples were measured at a strain rate in the linear viscoelastic regime and produced behavior typical of an elastic solid.

The dynamic mechanical response of each hydrogel blend at 20° C. under oscillatory shear is given in FIG. 9. The data portray both the elastic (G') and loss (G") moduli of each hydrogel as a function of angular frequency under 0.4-0.5% strain. The observed plateau behaviors in G' and G", combined with consistent ratios of G'/G" of 20-100 for the entire frequency range, are characteristics typical of elastic materials.

The mechanical properties were a function of the SOS content of the hydrogels as demonstrated in the indentation (Example 9) and tension (Example 10) studies. The near order of magnitude difference between the storage and loss modulus demonstrates the high elasticity of these materials even with their high water content.

Example 11—Unconfined Compression Testing

Hydrogels prepared according to Example 7 were also subjected to unconfined compression testing on an ARES-rheometer (TA Instruments, DE) using an 8-mm diameter compression tip (TA Instruments, DE) at room temperature (~22° C.). Swollen hydrogels were removed from water and excess water was blotted away. Hydrogels were centered on a 50-mm stainless steel flat plate and compressed until 2 g of normal force was measured on the instrument to ensure contact of the transducer with the gels. The hydrogels were then compressed to 40% strain at a strain rate of 2%/s while the force transducer measured the normal force response. This was performed for two cycles on each gel to check for mechanical permanent hysteresis.

For compressive cyclical testing, previously swollen samples were cut into 8 mm cylindrical disks with a biopsy punch and tested in DI water at room temperature to maintain hydration. Samples were mounted to a polished aluminum flat plate and compressed with a secondary aluminum plate attached to a 908 g load cell (Futek LSB200, Irvine, Calif.). A preload of 20 g was applied to the sample to ensure contact and the samples were compressed for 1,000 cycles using a servo hydraulic testing system (Bionic Model 370.02 MTS Corp, Eden Prairie, Minn.). Samples were compressed 12%/sec at a frequency of 1 Hz. Following the first 1,000 cycles the sample was unloaded and allowed to rest for 1 hour before being retested under the same conditions for four additional sets of 1,000 cycles.

MATLAB (Mathworks, Natick, Mass.) was used to analyze the resulting data. Peak compressive force and displacement for each cycle were used to ascertain the compressive modulus. Initial modulus was determined from the first cycle, while the modulus at 500 cycles and 1,000 cycles averaged from the ten cycles nearest those numbers. The initial and final modulus values and the percent decay were assessed over the first 500 and final 500 cycles.

Figure 10A:
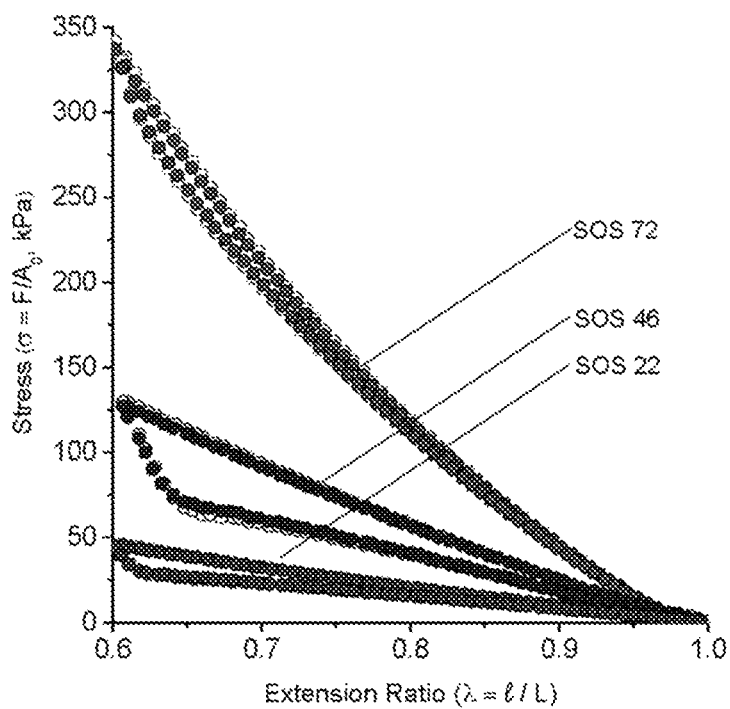
FIG. 10A All samples were compressed for 2 cycles to 40% strain at a strain rate of 2%/sec (filled circle: cycle 1, unfilled circle: cycle 2).

Two-cycle compression testing showed very little damage to the underlying polymer network of the gel, as each run traced the last. Each hydrogel recovered with little hysteresis (FIG. 10). Without wishing to be bound by theory, the varying hysteresis may be rooted in the degree to which the entanglements slowed recovery, which directly related to osmotic forces which redistributed water molecules throughout the sample.

Figure 10B:
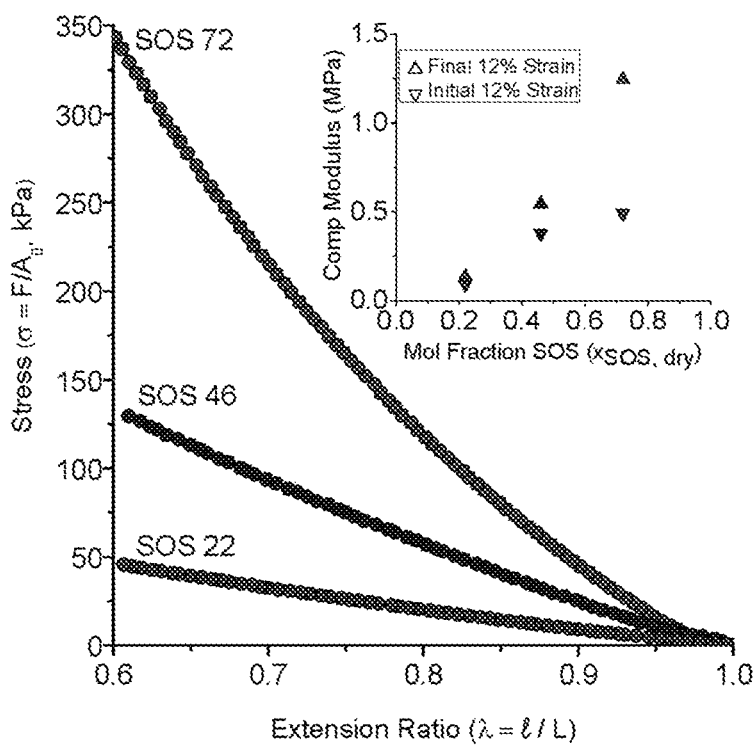
FIG. 10B Stress (kPa) vs. extension ratio of the initial compression of each of the three blends to 40% strain. (Upper right) Compressive modulus versus molar fraction SOS for the initial 12% strain and the final 12% strain (0-12% and 28-40%).

FIG. 10 showed the same dependence of SOS content increasing the modulus of the samples in compression. The trend carried not only at low strains of 12% as seen in indentation (Example 9), but also at higher strains of 40%. In the subset of FIG. 10B, the SOS content displayed an exponential relationship with the compressive modulus in these higher strains compared to decaying role in the lower strains. At higher strains, more topological entanglements and physical crosslinks from higher SOS content are engaged, producing a greater effective modulus.

Figure 11A:
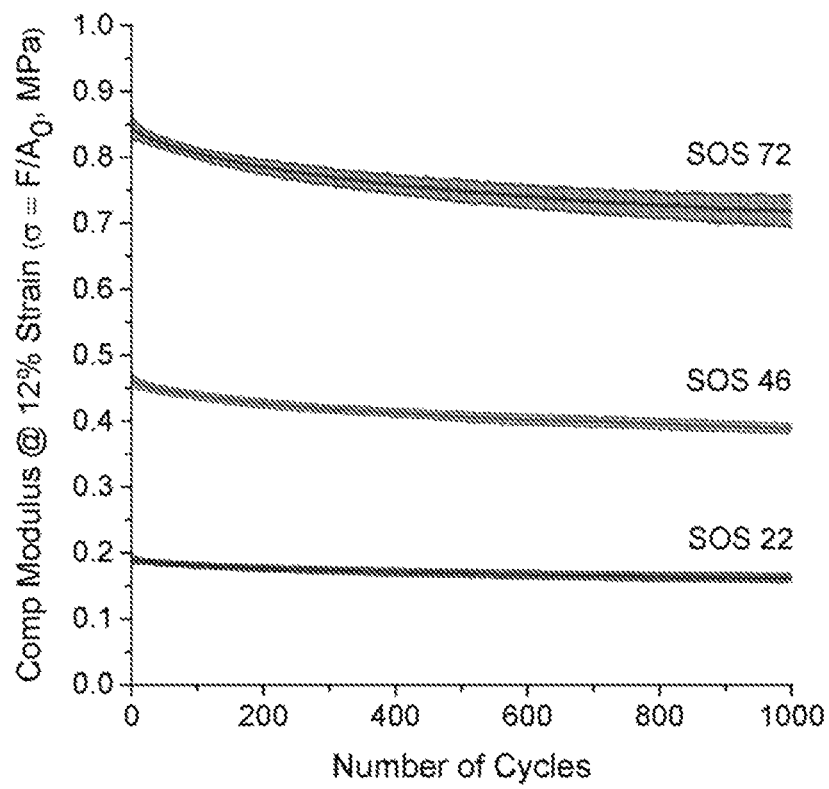
FIG. 11A Compressive fatigue testing of swollen hydrogels showing the recoverable loss in modulus for 5000 cycles on 22, 46, and 72 mol % SOS and the increasing modulus with increasing SOS content. All samples were compressed at a 12%/sec strain rate and a frequency of 1 Hz for 1000 cycles while fully submerged in a phosphate-buffered saline (PBS) bath, allowed to rest unloaded for 1 hour, and reloaded for four additional 1000 cycle runs.
Figure 11B:
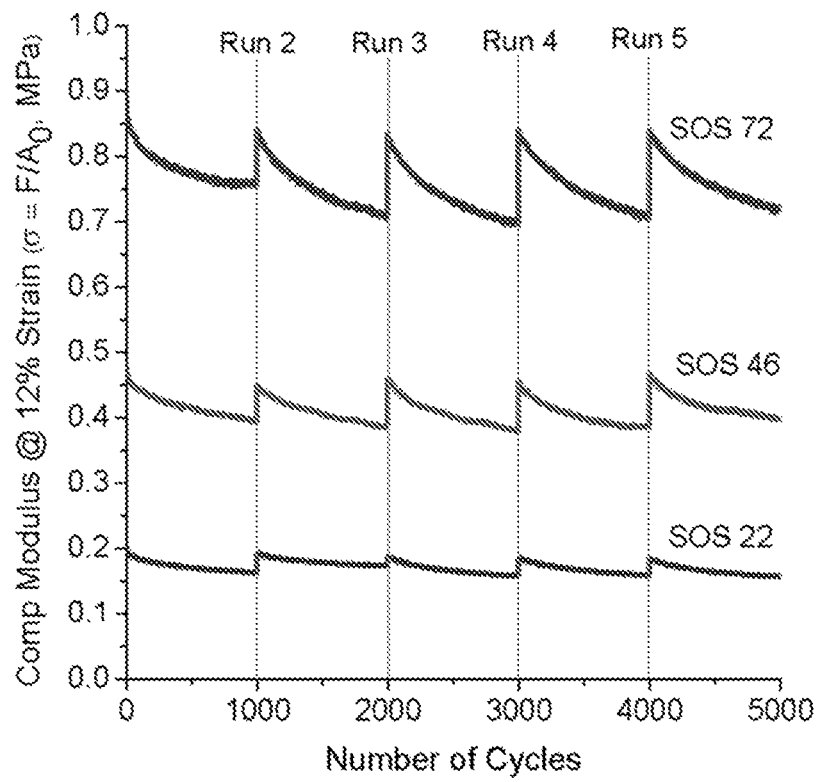
FIG. 11B The average of these 5 runs with standard deviation.

To better understand the materials' fatigue resistance, the three SOS content hydrogels were strained to 12% at a strain rate of 12%/sec for 5 consecutive 1000 cycle runs (FIGS. 11A & 11B). The average steady relaxation was 14.7±0.5% in the modulus throughout each 1000 cycles. Nonetheless, the original modulus of the prior run was recovered (98±4.5%), following one hour of no loading for the SOS-containing hydrogels. This result implied very little to no damage to the underlying polymer network upon these loading cycles. As evinced through video analysis, the shape fully recovers. This recoverable decay was likely from water moving within the hydrogel.

Table 2 shows the average modulus results and decay results across the 5 runs. The decay across the various SOS content was nearly identical for the full 1,000 cycles as well as the final 500 cycles, suggesting a similar mechanism. Traditionally, in high cycle fatigue testing, damage from cycle to cycle is due to stress concentrations leading to microcrack formations and mechanical failure of the material. Due to the minimal amount of fixed juncture points in the hydrogel system, there was a large amount of chain mobility. Recoverable energy absorption allowed the system to minimize stress concentrations and microcrack formations and to increase the mechanical longevity of the material. After each run, the hydrogel regained its original configuration, producing a narrowly-distributed pooled mean modulus over the first ten cycles (0.614±0.012 MPa).

TABLE 2

Average initial modulus (MPa), Average modulus over full 100 cycle run (MPa), Average decay in modulus throughout full run (%), and average decay over the second half of the 1000 cycle run (%) for three SOS content hydrogels (22, 46, and 72).

| Sample | Initial Modulus (MPa) | Mean Run Modulus (Mpa) | Full Run Decay (%) | Second Half Run Decay (%) |
|---|---|---|---|---|
| Average SOS 22 | 0.19 ± 0.008 | 0.17 ± 0.009 | 14.4 ± 4.3 | 4.2 ± 1.2 |
| Average SOS 46 | 0.46 ± 0.01 | 0.41 ± 0.007 | 15.2 ± 1.9 | 4.4 ± 1.1 |
| Average SOS 72 | 0.85 ± 0.015 | 0.76 ± 0.024 | 14.6 ± 2.0 | 4.2 ± 2.0 |

Figure 12:
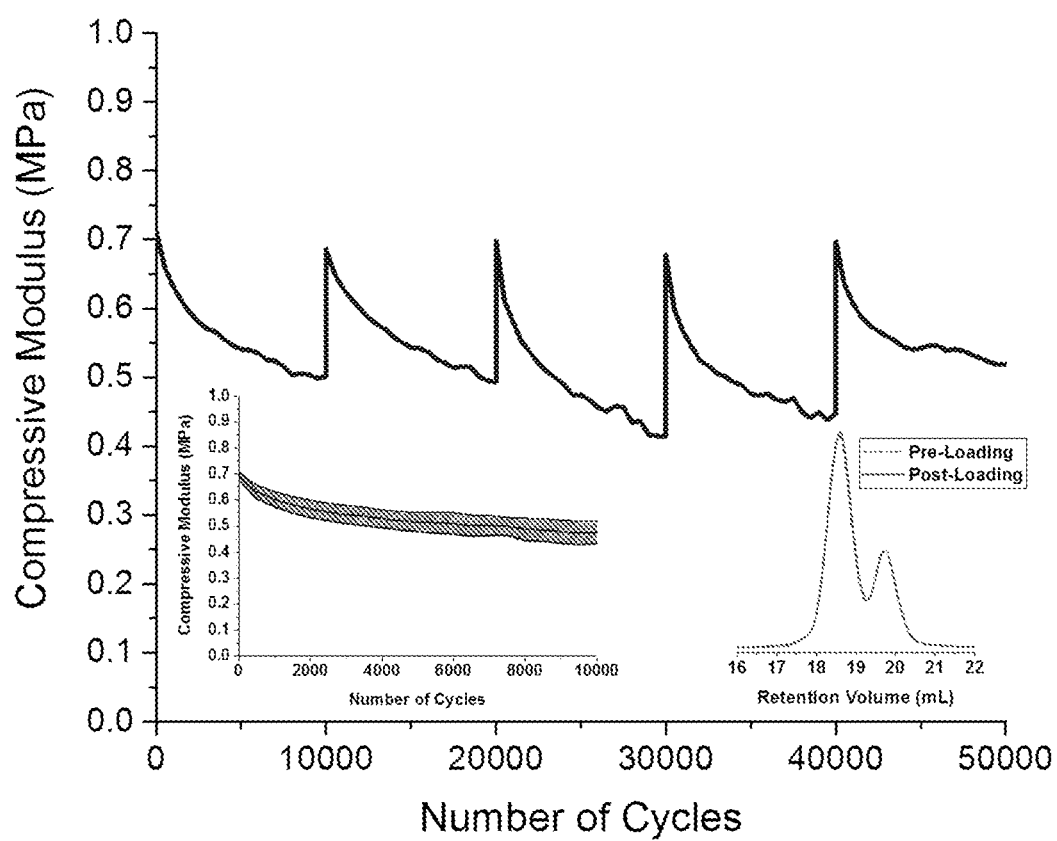
FIG. 12. Example of an SO/SOS hydrogel composed of 61 mol % SOS subjected to five successive runs of 10,000 cycles each, in which 12% compression was applied at a frequency of 1 Hz.

FIG. 12 exemplifies an SO/SOS hydrogel composed of 61 mol % SOS subjected to five successive runs of 10,000 cycles each, in which 12% compression was applied at a frequency of 1 Hz. The hydrogel was allowed to rest under no applied strain for the balance of 24 hours before the next run. The modulus represented the mean value over the entire 12% compression, calculated as maximum stress over strain. The left inset shows the average mean modulus for all five 10,000 cycle runs. The right inset shows the SEC data for the two-component blend before and after the full 50,000 cycle experiment.

Figure 13:
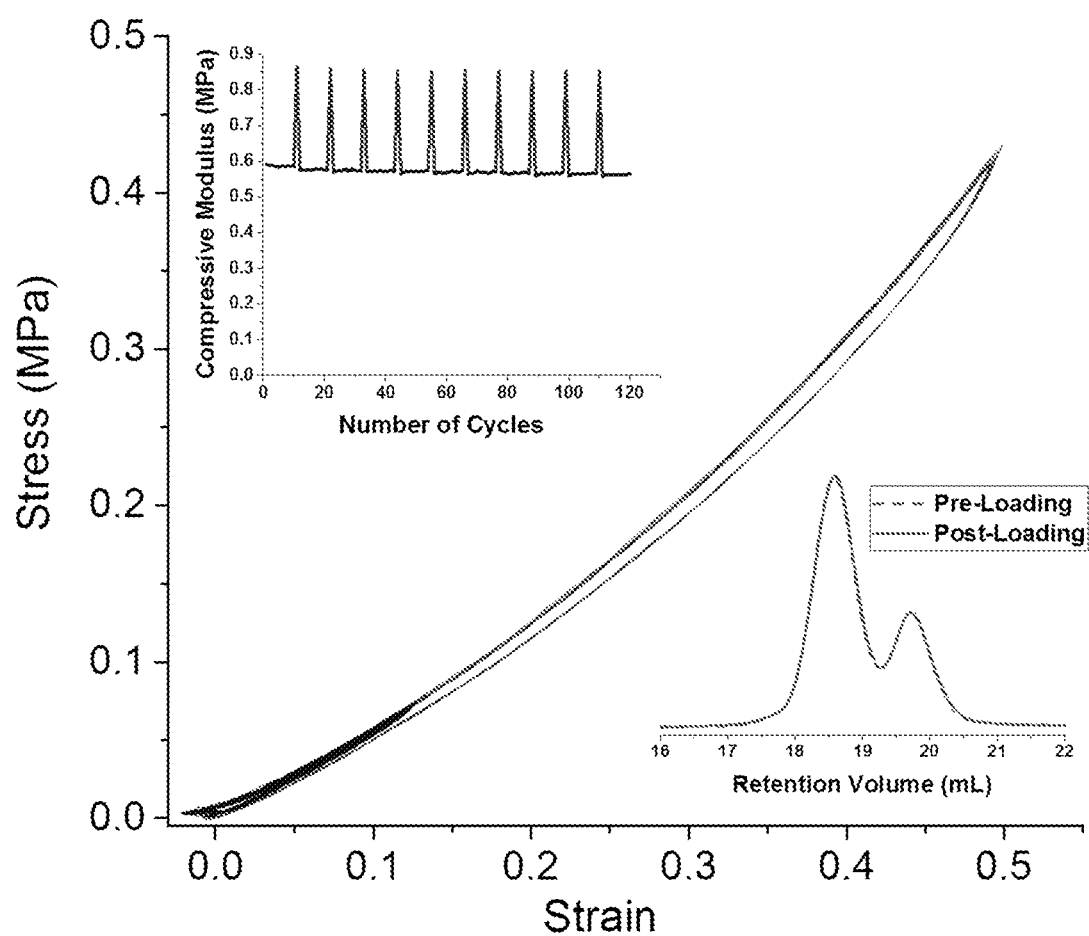
FIG. 13. Example of an SO/SOS hydrogel composed of 61 mol % SOS subjected to a compression overloading experiment, in which 12% compression was applied at a frequency of 1 Hz, with 50% compression applied every 11$^{th}$ cycle.

FIG. 13 exemplifies an SO/SOS hydrogel composed of 61 mol % SOS subjected to a compression overloading experiment, in which 12% compression was applied at a frequency of 1 Hz, with 50% compression applied every 11$^{th}$ cycle. The stress strain behavior for all 120 cycles is shown. The upper inset shows the mean modulus calculated over the entire 12 or 50% compression, calculated as maximum stress over strain. The lower inset shows the SEC data for the two component blend before and after the full 120 cycle experiment. Each cycle showed very little hysteresis between the loading and unloading legs, indicating that minimal energy dissipated. Without wishing to be bound by theory, the reduced hysteresis and relaxation in the modulus may result from deformation in the fluid structure and poroelastic flow.

Figures 14A, 14B:
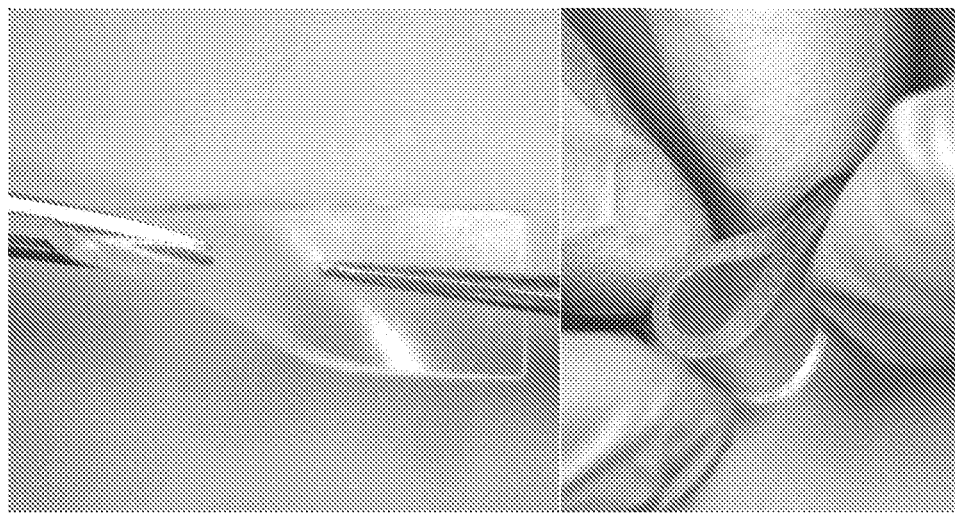
FIGS. 14A and 14B. Examples showing the handling ability of the TPE hydrogels.
Figures 14C, 14D, 14E, 14F:
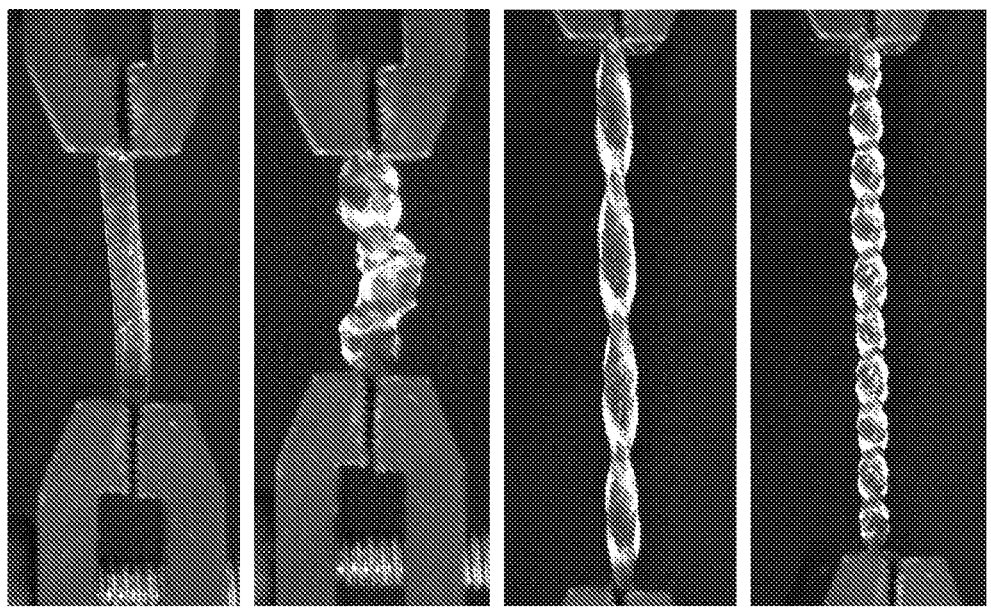
FIG. 14C $\lambda=1$, $\phi=0$.
FIG. 14D $\lambda=1$, $\phi=4\pi$.
FIG. 14E $\lambda=2.5$, $\phi=4\pi$.
FIG. 14F $\lambda=2.5$, $\phi=10\pi$.

FIGS. 14A and 14B show the handling ability of the TPE hydrogels. (C-F) SOS61 held with tweezers. Elastomer-like bending (SOS61). Twisting ability (SOS30) from left to right: (C) λ=1, ϕ=0; (D) λ=1, ϕ=4π; (E) λ=2.5, ϕ=4π; and (F) λ=2.5, ϕ=10π.

Figure 15:
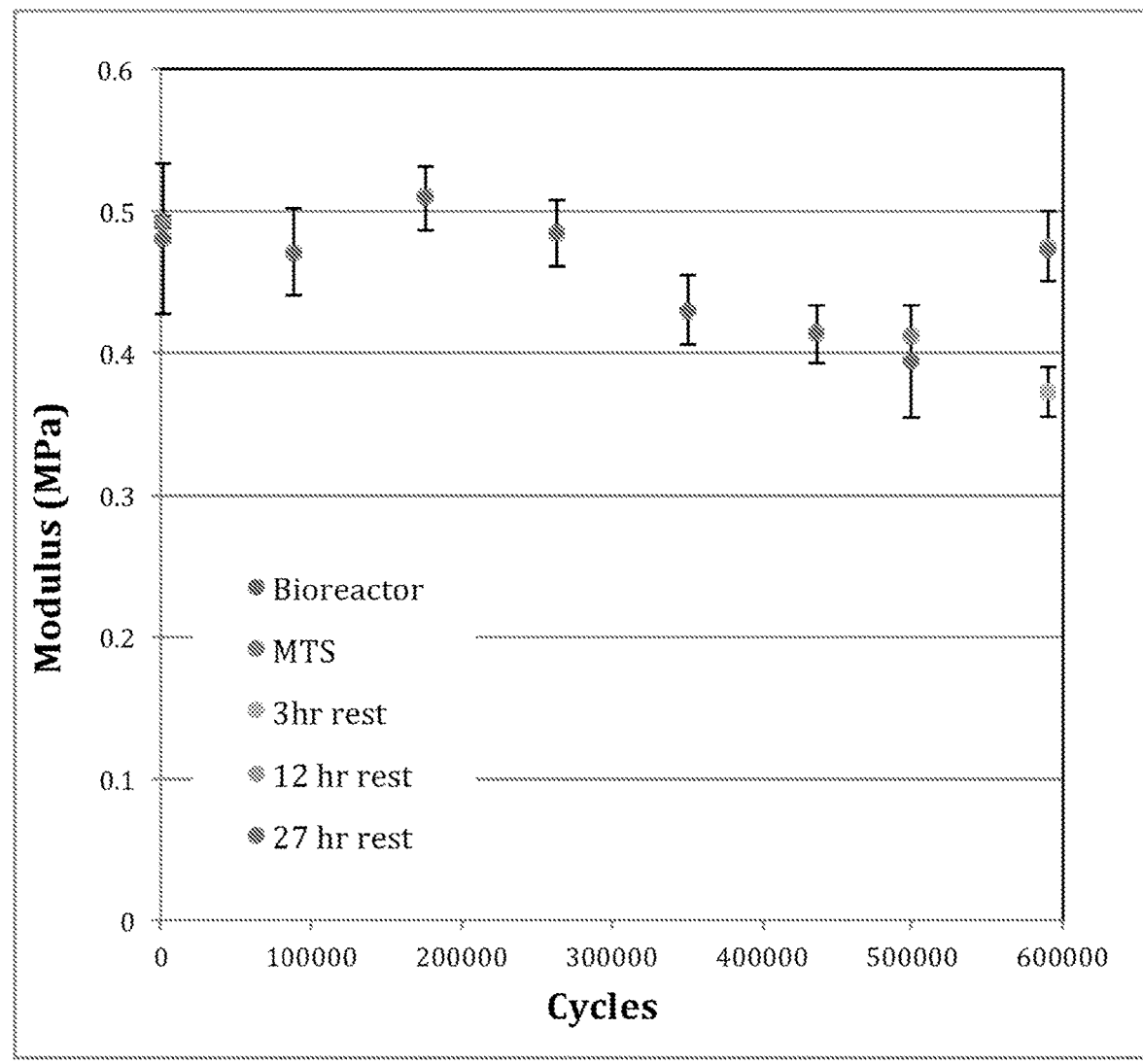
FIG. 15. Example of an SO/SOS hydrogel composed of 61 mol % SOS subjected to 500,000 continuous compression cycles, in which 12% compression was applied at a frequency of 1 Hz.

FIG. 15 exemplifies an SO/SOS hydrogel composed of 61 mol % SOS subjected to 500,000 continuous compression cycles, in which 12% compression was applied at a frequency of 1 Hz. Each data point plotted was derived from the 1000 cycle average of the mean modulus for a given cycle, calculated as maximum stress over strain. The data at 600,000 cycles showed the recovery of the average mean modulus (taken over 1000 cycles) as a function of rest time following the 500,000-cycle test. Comparing moduli as a function of cycle number suggests that the cycled samples may have a faster rate of relaxation once extensively cycled with no observed changes in molecular weight distribution.

Example 12—Synthesis of azido-polystyrene-b-polyethylene(oxide) ("SO-azide")

Various fractions of the parent hydroxyl-functional SO diblock copolymer from Example 5 were substituted with click functionality (SO-azide in this example and SO-alkyne below at Example 13). The SOS triblock copolymer continued to serve as the component forming the primary network in the hydrogel. The azide and alkyne functional SO diblock copolymers provided a latent ability to generate more triblock copolymer at a future time; that is, once the SOS-SO glass had been hydrated and the primary network of triblock copolymer tethers had been established and mechanically engaged as a hydrogel.

SO-azide was prepared via substitution after converting the terminal alcohol groups on the parent SO diblock copolymer to their corresponding sodium or potassium alkoxides. To generate SO-azide, the terminal alkoxide was first converted to a mesyl leaving group before displacement in the presence of sodium azide.

Figure 16:
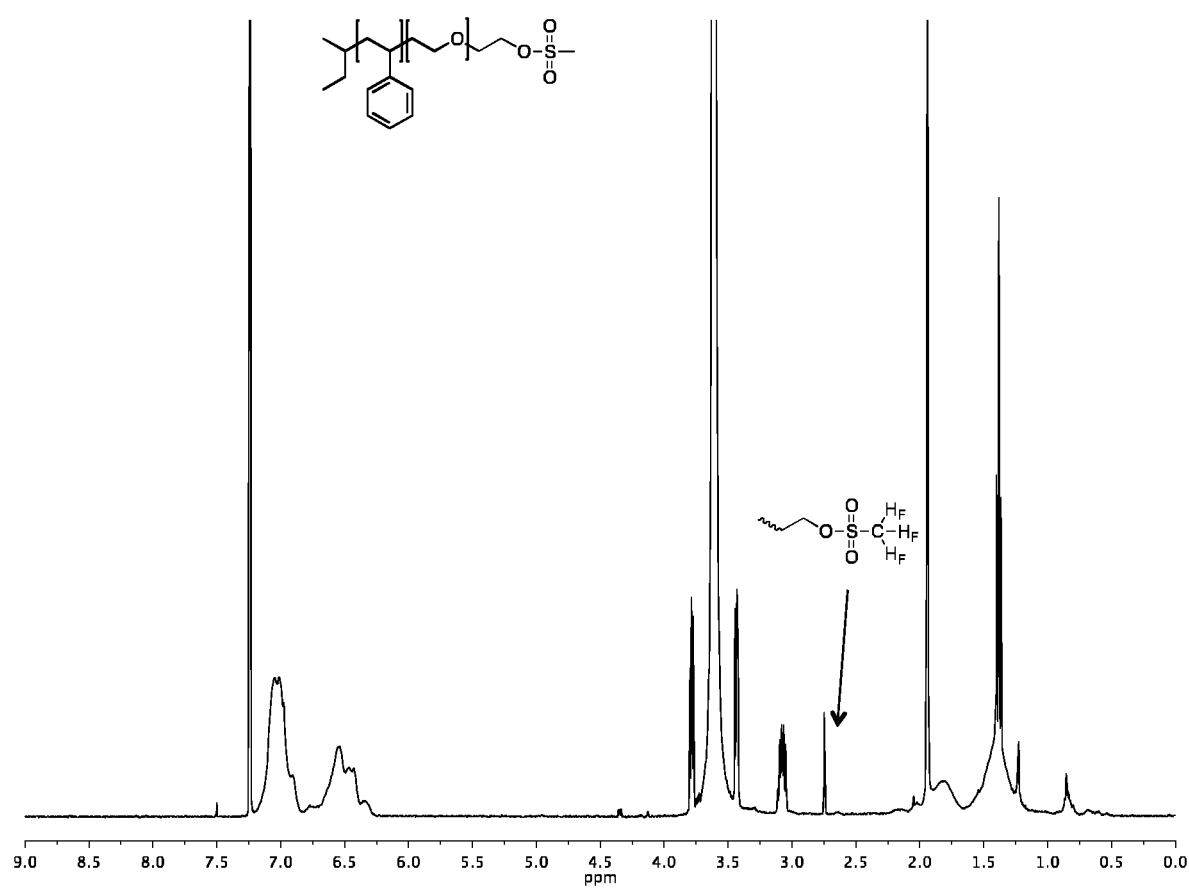
FIG. 16. $^1$H-NMR spectrum of methanesulfonyl-polystyrene-poly(ethylene oxide) ("PS-PEO-Ms," "SO-Ms")). This compound was the precursor of PS-PEO-azide.

To do this, S—OH (5.42 g, 7.8×10$^{-5}$ mol) from Example 1 was added to a 300-mL flask, which was thrice evacuated and backfilled with Ar. Distilled methylene chloride (100 mL) was added to dissolve the polymer. The flask was placed to a 45° C. oil bath at before adding methanesulfonyl chloride (MsCl, 0.12 mL, 20 equiv.) and triethylamine (0.2 mL, 20 equiv.). The reaction stirred overnight and the crude product was filtered then precipitated into pentane (1 L). The solid was collected via vacuum filtration and dried under vacuum overnight to produce a white solid. Yield 5.25 g, 95+%. SEC: (THF, PS stds): $M_{n,SO\text{-}azide}$=70,000 g mol$^{-1}$ (Calculated using $M_{n,S-OH}$ (SEC) and SO-azide $^1$H NMR. Changes in molecular weights due to end group conversions fall below the accuracy of the calculated values and were therefore neglected), $M_w/M_n$=1.05; $^1$H-NMR: $\delta_H$ (400 MHz; CDCl$_3$): 6.20-7.26 (b, —C$_6$H$_5$, —OCH$_2$(C$_6$H$_4$)CH$_2$O—), 4.55 (s, —OCH$_2$(C$_6$H$_4$)CH$_2$O—), 4.2-4.4 (t, —CH$_2$—SO$_3$—CH$_3$), 3.1-4.0 (b, —CH$_2$CH$_2$O—, —CH(C$_6$H$_5$)CH$_2$CH$_2$O—), 2.7 (s, —CH$_2$—SO$_3$—CH$_3$), 1.0-2.30 (b, —CH$_2$CH(C$_6$H$_5$)—, CH$_3$CH(CH$_2$CH$_3$)—, —CH(C$_6$H$_5$)CH$_2$CH$_2$O—), 0.5-0.78 (m, CH$_3$CH(CH$_2$CH$_3$)—). See FIG. 16.

Figure 17:
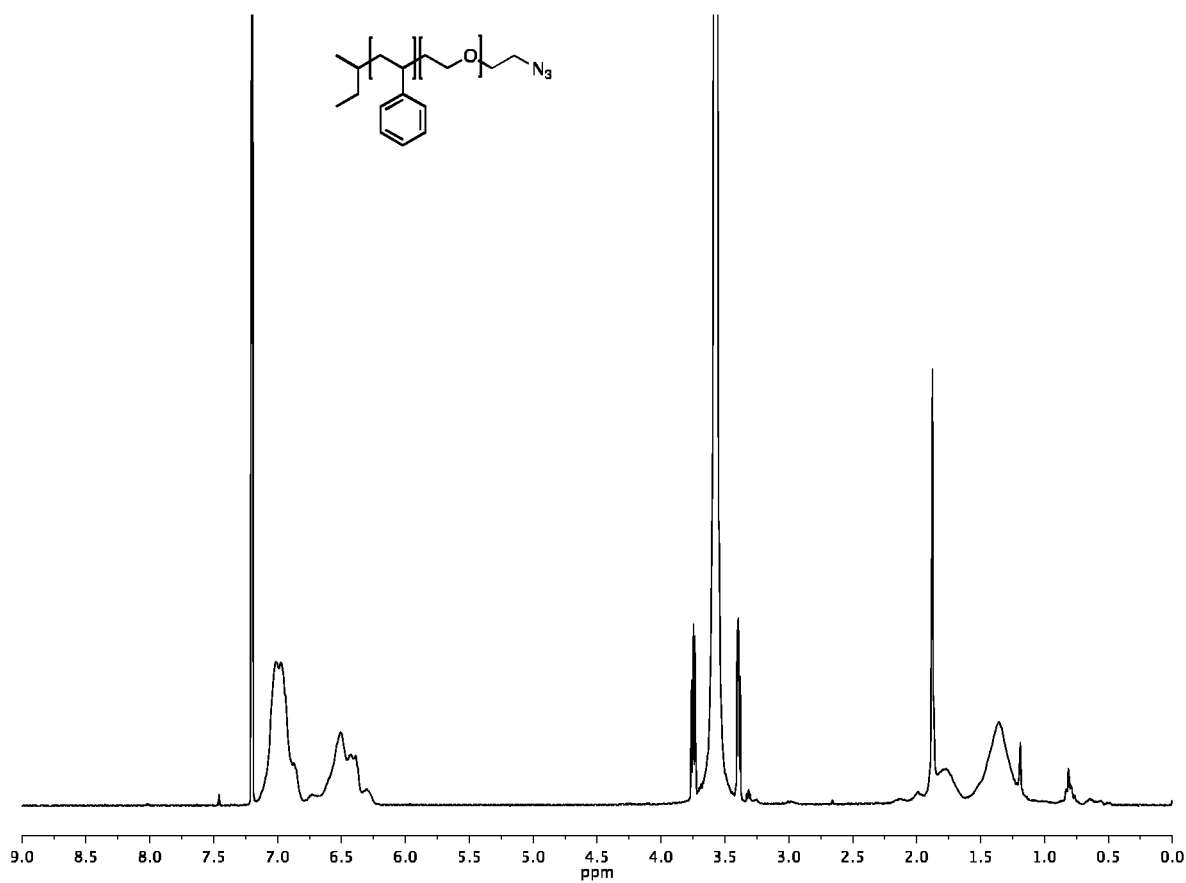
FIG. 17. $^1$H-NMR spectrum of azido-polystyrene-poly(ethylene oxide) ("PS-PEO-azide," "SO-azide"). The terminal methylene protons adjacent to the azide end group overlap with the methylene protons of the PEO backbone (4.0-3.2 ppm). Confirmation of azide group functionality is shown in the FTIR spectrum in FIG. 18.

Methansulfonyl polystyrene-b-polyethylene(oxide) ("SO-Ms," 4.75 g, 6.9×10$^{-5}$ mol) was placed in a 300-mL round bottom flask containing purified DMF under argon in an bath at 60° C. After the polymer was completely dissolved, sodium azide (NaN$_3$, 0.089 g, 20 equiv.) was added to the reaction mixture with vigorous stirring. The crude reaction mixture was filtered after an overnight reaction and then precipitated into ethyl ether. The collected powder was then dissolved in chloroform and washed with DI water. The polymer solution in chloroform was dried over magnesium sulfate and filtered. White powder was collected though filtration under vacuum after the precipitation into pentane. The polymer was then dried under vacuum at room temperature overnight. Yield 4.2 g, 88%. SEC: (THF, PS stds): $M_{n,SO\text{-}Ms}$=70,000 g mol$^{-1}$ (Calculated using $M_{n,S-OH}$ (SEC) and SO-Ms $^1$H NMR. Changes in molecular weights due to end group conversions fall below the accuracy of the calculated values and were therefore neglected), $M_w/M_n$=1.05; $^1$H-NMR: $\delta_H$ (400 MHz; CDCl$_3$): 6.20-7.26 (b, —C$_6$H$_5$, —OCH$_2$(C$_6$H$_4$)CH$_2$O—), 4.55 (s, —OCH$_2$(C$_6$H$_4$)CH$_2$O—), 3.1-4.0 (b, —CH$_2$CH$_2$O—, —CH(C$_6$H$_5$)CH$_2$CH$_2$O—), 1.0-2.30 (b, —CH$_2$CH(C$_6$H$_5$)—, CH$_3$CH(CH$_2$CH$_3$)—, —CH(C$_6$H$_5$)CH$_2$CH$_2$O—), 0.5-0.78 (m, CH$_3$CH(CH$_2$CH$_3$)—). See FIG. 17.

Figure 18:
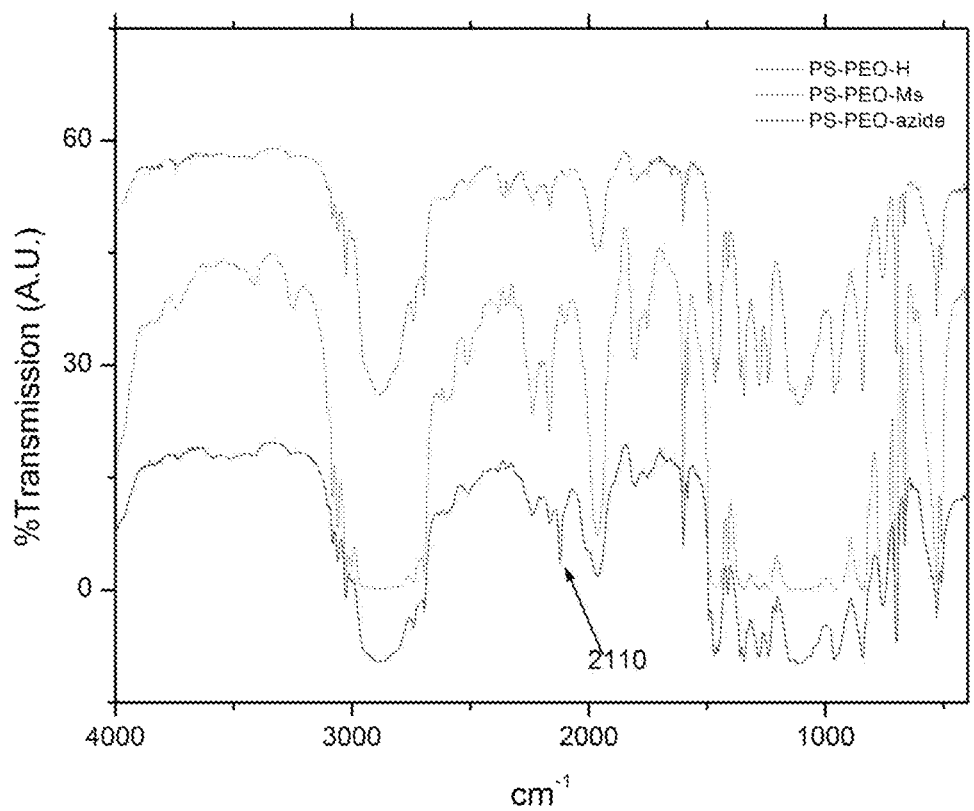
FIG. 18. FTIR spectra of PS-PEO-H ("SO"), PS-PEO-Ms and PS-PEO-azide. The characteristic vibration for the azide group was shown at 2110 cm$^-$.

The methylene protons adjacent to the azide group overlapped with the ethylene oxide backbone and could not be resolved. Complete disappearance of the methyl protons of the mesyl group indicated a successful substitution. FTIR confirmed the presence of an azide vibration (2110 cm$^{-1}$) (FIG. 18). While complete functionalization of the SO-azide could not be confirmed, blends involving SO-azide and SO-alkyne were assembled assuming functionalization of both block copolymers was quantitative.

Example 13—Synthesis of polystyrene-b-polyethylene(oxide)-alkyne ("SO-alkyne")

The polystyrene-b-polyethylene(oxide)-alkyne ("SO-alkyne") was achieved by treating the SO alkoxide with propargyl bromide. S—OH (Example 1, 6.31 g, 9.1×10-5 mol) was placed into a 500-mL two-neck round bottom flask. Dry THF (250 mL) was added to the flask. The solution was heated in a 50° C. oil bath under argon. Once the S—OH was completely dissolved, sodium hydride (0.23 g, 100 equiv.) was added to the solution and stirred for 20 minutes. Propargyl bromide solution in toluene (80 wt %, 0.31 mL, 20 equiv.) was injected to the reaction mixture via an air-free syringe. The temperature was increased to 65° C. to reflux overnight. The reaction mixture was filtered and precipitated three times into pentane (1 L). The suspension was filtered and dried under vacuum overnight to give pale yellow powder.

Figure 19:
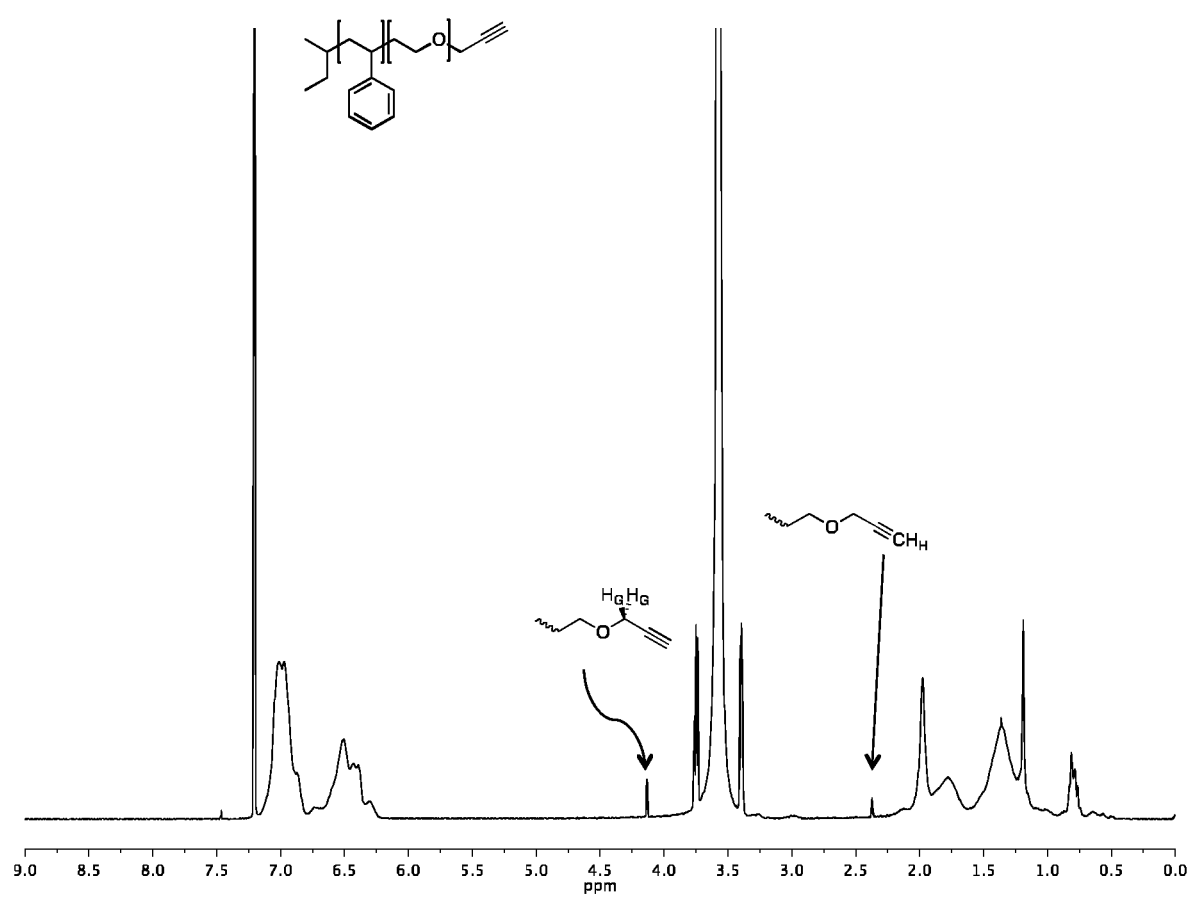
FIG. 19. $^1$H-NMR spectrum of PS-PEO-alkyne.

$^1$H-NMR confirmed transformation of the hydroxyl groups to alkyne groups to be essentially quantitative, given the uncertainty associated with end-group analysis of large polymer molecules by $^1$H-NMR. Yield 5.65 g, 89%. SEC (THF, PS stds): $M_{n,SO-alkyne}$=70,000 g mol$^{-1}$ (Calculated using $M_{n,S-OH}$ (SEC) and SO-alkyne $^1$H-NMR. Changes in molecular weights due to end group conversions fall below the accuracy of the calculated values and were therefore neglected), $M_w/M_n$=1.05; $^1$H-NMR: $\delta_H$ (400 MHz; CDCl$_3$): 6.20-7.26 (b, —C$_6$H$_5$, —OCH$_2$(C$_6$H$_4$)CH$_2$O—), 4.55 (s, —OCH$_2$(C$_6$H$_4$)CH$_2$O—), 4.2 (d, —OCH$_2$C≡C), 3.1-4.0 (b, —CH$_2$CH$_2$O—, —CH(C$_6$H$_5$)CH$_2$CH$_2$O—), 2.46 (t, —C≡CH), 1.0-2.30 (b, —CH$_2$CH(C$_6$H$_5$)—, CH$_3$CH (CH$_2$CH$_3$)—, —CH(C$_6$H$_5$)CH$_2$CH$_2$O—), 0.5-0.78 (m, CH$_3$CH(CH$_2$CH$_3$)—). The $^1$H-NMR spectrum of PS-PEO-alkyne is shown at FIG. 19.

Example 14—Preparation of SO/SO-alkyne/SO-azide/SOS Blends

Polymer blends containing between about 8.5 mol % and about 10 mol % SOS and varying, equimolar amounts of SO-azide (Example 12) and SO-alkyne (Example 12) were prepared via solution blending (with freeze-drying) from benzene. The SO-azide:SO-alkyne ratio was held constant at 1:1 and the blend was diluted with reactively inert SO, producing four distinct blends (A$_{pre}$-D$_{pre}$) with varying SO-azide/SO-alkyne content as shown in Table 3.

Figure 20A:
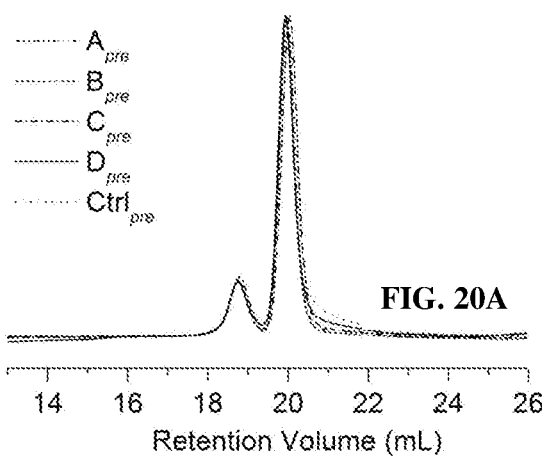
FIG. 20. Representative SEC data for hydrogels formed from blends A through D FIG. 20A before (pre) and FIG. 20B after (post) exposure to the Cu(I) catalyst. All SEC traces were normalized to a constant area under the SO-X diblock copolymer peak (right) to show the relative amounts of SOS triblock copolymer (left peak) more clearly. Control samples contained only SO and SOS.
Figure 20B:
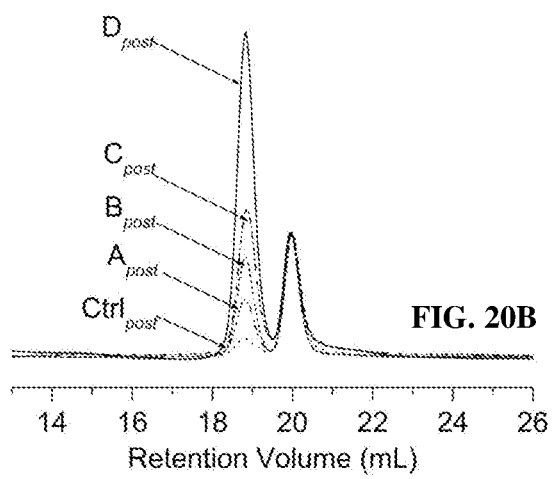

SOS triblock copolymer compositions are based on integration of SEC traces following solution blending (FIG. 20, left). The amount of pre-blended SOS triblock unintentionally varies somewhat (8.9-10.4 mol %) across the four blends, which is attributable to massing error, SEC peak integration, and local variations in blend composition.

Uniform disks (8 mm diameter, 0.24-0.28 mm thickness, 0.015-0.016 g) of samples A through D were prepared via melt pressing at 150° C. for five minutes. Azide-alkyne Huigsen cycloadditions (click reactions) can occur at high temperatures without metal catalyst. Several control experiments were run before and after melt pressing azide-alkyne functional SO and no thermally-induced coupling was indicated in the SEC traces. Molecular weight degradation was also not observed. Functional group integrity during melt pressing proved difficult to accurately assess (via $^1$H-NMR, e.g.) given the reduced concentration of end groups in the blends. However, independent melt processing of neat SO-alkyne showed no change in chain end functionality occurred during heating for such short times.

Each blend sample was prepared by solution blending (1 g total polymer in 20 mL benzene) the appropriate amounts of SO (Example 3), SO-alkyne (Example 12), SO-azide (Example 13), and SOS (Example 4, 10 mol % for all blends) to produce blends containing the specified amount of the "clickable" SO moieties. Solutions were frozen using an ethanol/liquid nitrogen slush bath and then dried under vacuum at room temperature overnight.

Example 15—Swelling and In-Situ Coupling Protocols (DN Formation)

Dry polymer disks of four blends prepared accordingly to Example 13 were placed into a 300-mL round-bottom flasks containing degassed DI water (100 mL) until the equilibrium swelling (~1 hr.) at room temperature. Equilibrated hydrogels were removed the degassed DI water and placed onto a Teflon™ surface. After excess water was blotted, the hydrogels were weighed and returned to the flasks with freshly degassed water (100 mL) and degassed for another 10 minutes. Copper sulfate solution (0.25 mL, 0.007 M, in degassed DI water) and sodium ascorbate solution (1 mL, 0.009 M, in degassed DI water) were injected into the flasks via air-free syringes. The reaction mixture was kept at room temperature overnight. Finally, the hydrogels were left in the degassed DI water for one hour to remove the catalyst before any characterization was performed.

The four blends prepared according Example 14 (A through D) each contained about (1) 8.9 mol % to 10.4 mol

TABLE 3

Hydrogel composition and post-swelling click chemistry reaction conversion

| Sample | SOS$_{pre}$ (mol %)[a] | SO—X$_{pre}$ (mol %)[a] | SO-azide:SO-alkyne:S—OH[a] | SOS$_{max}$ (mol %)[b] | SOS$_{post}$ (mol %)[a] | Coupling conversion (%)[c] |
|---|---|---|---|---|---|---|
| A1 | 9.3 | 90.7 | 1:1:4 | 28.8 | 20.2 | 60.0 |
| A2 | | | | | 18.4 | 50.8 |
| A3 | | | | | 21.2 | 65.0 |
| A4 | | | | | 20.3 | 60.0 |
| B1 | 9.8 | 90.2 | 1:1:8/5 | 46.5 | 29.0 | 59.4 |
| B2 | | | | | 30.7 | 63.8 |
| B3 | | | | | 29.8 | 61.4 |
| B4 | | | | | 22.7 | 41.9 |
| C1 | 10.4 | 89.6 | 1:1:4/7 | 69.4 | 39.7 | 60.2 |
| C2 | | | | | 42.9 | 65.3 |
| C3 | | | | | 37.5 | 56.6 |
| C4 | | | | | 32.4 | 47.7 |
| D1 | 8.9 | 91.1 | 1:1:0 | 100 | 48.0 | 58.0 |
| D2 | | | | | 48.4 | 58.4 |
| D3 | | | | | 52.0 | 62.3 |
| D4 | | | | | 52.1 | 62.3 |
| D5 | | | | | 45.1 | 54.8 |

[a]Molar percentages calculated based on GPC peak integrations.
[b]Sum of SOS$_{pre}$ and maximum theoretical increase in SOS possible assuming quantitative coupling between all added azide- and alkyne-functional SO diblock copolymer in the blend. This increase assumed azide and alkyne functionalization was quantitative following modification.
[c]Coupling conversions were calculated as the ratio of the measured SOS increase (SOS$_{post}$ − SOS$_{pre}$) to the maximum theoretical increase (SOS$_{max}$ − SOS$_{pre}$) with quantitative coupling.

% SOS triblock copolymer, (2) varying, equimolar amounts of SO-azide and SO alkyne diblock copolymer, and (3) a balance of reactively inert SO diblock copolymer. The concentration of SO-azide and SO-alkyne were chosen such that the baseline values of 8.9-10.4 mol % SOS in each sample before swelling could be theoretically increased to values ranging from 28.8 mol % (blend A) to 100 mol % (blend D) aggregate SOS triblock copolymer in the final hydrogel network (Table 2).

Figure 21:
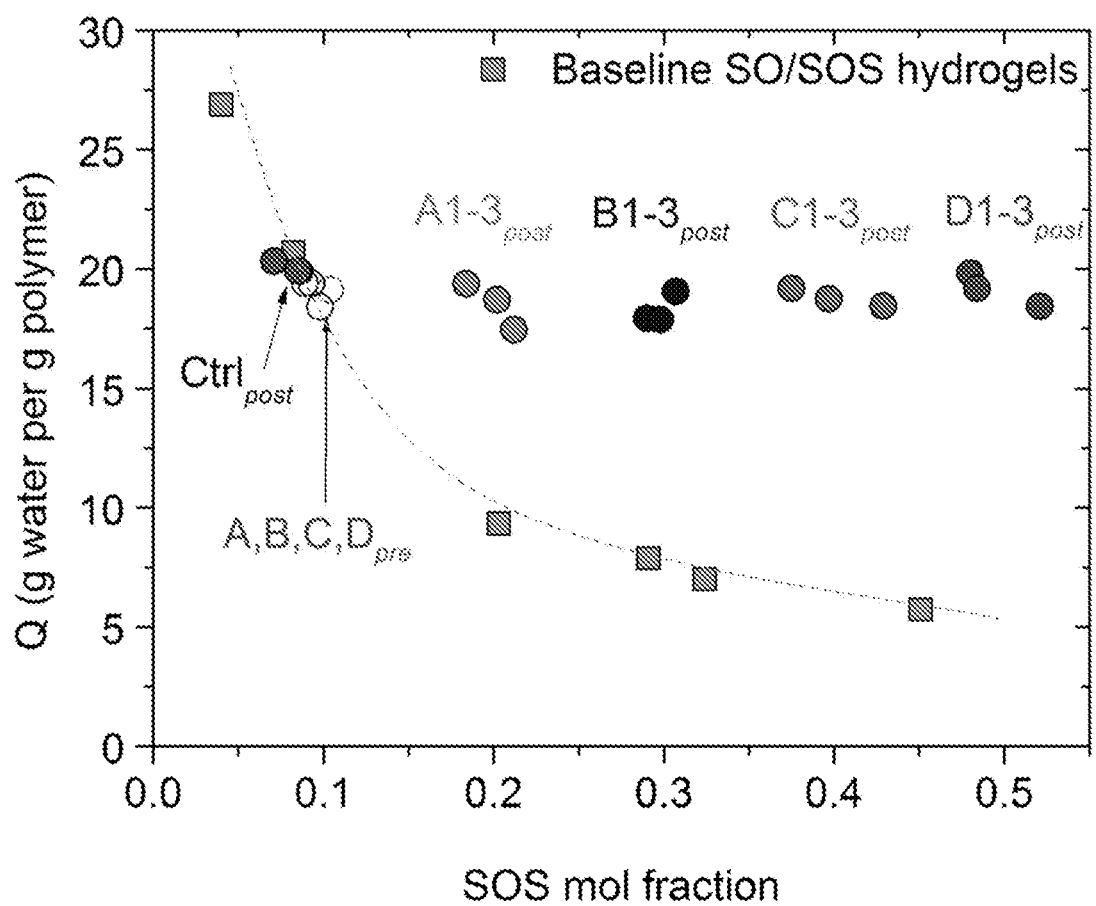
FIG. 21. Hydrogel swelling ratio (Q) as a function of SOS triblock copolymer composition.

Multiple polymer disks were melt-pressed from each of the blends A through D (Table 2). The disks were individually swollen in excess DI water until reaching equilibrium dimensions (about one hour evident by constant mass and size). The Q values for hydrogel disks formed from each blends A through D prior to exposure to Cu(I) catalyst are shown in FIG. 21. The inclusion of SO diblock copolymer that contained terminal azide or alkyne functionality had no particular influence on the equilibrium swelling dimensions compared to that expected from baseline SO/SOS type hydrogels with similar SOS triblock copolymer compositions. That is, all hydrogels from the blends exhibited pre-click Q values in the 18-20 g $H_2O$/g polymer range, consistent with an SOS tether content of 8.9-10.4 mol %. This behavior confirmed the hypothesis that the integration of chain end functionality other than the native hydroxyl at the PEO chain end could be done without disruption of the basic network swelling behavior.

Each hydrogel solution (hydrogel in excess DI water) was degassed with argon before adding sodium ascorbate and copper (II) sulfate. The combination of copper sulfate and sodium ascorbate produces the Cu(I) catalyst in-situ to facilitate the Huisgen cycloaddition reaction between terminal azide and alkyne functional groups of the hydrated PEO blocks. Absent oxygen removal from the hydrogel solutions before adding catalyst, PEO degraded significantly, as verified with SEC. Hydrogel samples were left in the catalyst solution for 24 hours before removal, followed by sequential self-dialysis (osmotic driving force provided by concentration gradient between the hydrogel interior and exterior) against fresh DI solutions to remove residual catalyst. Preliminary kinetic experiments were used to confirm the 24-hour reaction time was sufficient to reach maximum conversion. Coupling efficiencies were calculated based on the percent of azide (or alkyne) functional groups reacted as quantified through SEC, using the observed SOS triblock copolymer added to the system following exposure to the Cu(I) catalyst. Representative SEC data is shown in FIG. 20 for each of the blends with the results of all coupling reactions summarized in Table 3. Beyond the molecular weight distributions captured in these SEC traces, the data demonstrates the unique ability to deconstruct these TPE hydrogels back into their constituent block copolymer species through removal of water and dissolution in an organic solvent. Even after introducing the secondary network, the hydrogel remained a physically cross-linked mixture of diblock and triblock copolymer, which can be recovered and reprocessed.

A control sample composed of only SO diblock and SOS triblock copolymer, absent azide/alkyne functionality, was also run in parallel to determine the effect of sodium ascorbate and copper (II) sulfate solution on the constituent polymer species. The SEC traces of the control sample before and after exposure to the catalyst system for 24 hours showed no significant change, suggesting neither degradation nor significant side-reactions (FIG. 20). To ensure that coupling in the sample was macroscopically uniform across the bulk dimensions of the sample and not influenced by diffusion limitations in either copper sulfate or sodium ascorbate, SEC was also performed on sections taken from both inner and outer regions of a disk. No significant differences in regional coupling were detected in any samples tested.

SEC analysis of the total SOS triblock copolymer after the post-swelling click chemistry varied from 18.4-52.0 mol %, depending on blend. These values reflected a coupling efficiency that remained almost constant (58.1%±6.3%) across all samples despite variation in the amount of azide/alkyne functional polymer. This likely indicated some degree of non-quantitative functionality in the initial materials (e.g. PS-PEO-azide at <100% functionality). Post-reaction $^1$H NMR and FTIR indicated both azide and alkyne groups were still present in small amounts, although the size of the block copolymers have made quantification unreliable.

In addition to non-quantitative functionality in SO-azide (or SO-alkyne), performing the reaction within the context of a fixed morphology also determined coupling efficiency. The self-assembled sphere morphology placed PEO chains of the corona close to those belonging to adjacent spherical domains. This structure spatially directed or concentrated terminal azide and alkyne groups into defined regions, which should enhance coupling efficiencies when the number of functional chain ends in the region was high (as it was at low conversions). The reaction volume available to each functional group was constrained by the limited travel available to each PEO chain end, given the opposing end was anchored to a fixed junction point (spherical domain) in the network. As the conversion proceeds to higher values, and residual functional group concentrations diminished, the occurrence of orphaned chain ends was likely.

The post-click Q values for three hydrogels from each blend type are given in FIG. 21 as a function of their new total SOS triblock copolymer compositions. Installing additional SOS triblock copolymer through click coupling under equilibrium swelling conditions had no significant influence on the water content of the hydrogel. That is, the Q values still reflected the SOS triblock copolymer composition before swelling. Q values for the baseline SO/SOS hydrogels are included in FIG. 21 and provide a direct comparison between hydrogels of similar total SOS triblock copolymer compositions, differing only in how the triblock copolymer were introduced into the system.

To summarize, one can predetermine water content by selecting the percentage of SOS triblock copolymer used during melt-state self-assembly. The post-swelling click chemistry then provided an additional, secondary network of SOS tethers while preserving the original Q values.

Example 16—Dynamic Shear and Unconfined Compression Testing

The rheology and unconfined compression test results for the samples of Example 15 were collected on a TA Instruments ARES rheometer at room temperature using parallel plate geometry with an infinite lower plate and an 8-mm upper plate. The bottom plate was the bottom of an integrated glass cup outfitted with a humidified cover. The swollen hydrogels were placed onto the bottom plate with excess water blotted away. The hydrogel thicknesses were measured on the rheometer and determined by the gap value between the parallel plates when the normal force on the upper plate reached 2 grams force. Since all unstrained hydrogels exceeded 8-mm diameters, the stresses were calculated from the fixed upper plate dimensions. To eliminate slip between the upper plate and the hydrogel samples during the rheological property measurements, 10% compressive strain was applied on each hydrogel sample. Dynamic frequency sweeps were performed on each sample using a shear strain in the range of 0.15-3% (linear viscoelastic region) over a frequency of 0.1 to 100 rad/s. For unconfined compression tests, the gels were compressed to 40% using a rate of 20%/minutes Two compression-decompression cycles were performed to study the possible hysteresis also using the rate of 20%/min during decompression.

Figure 22:
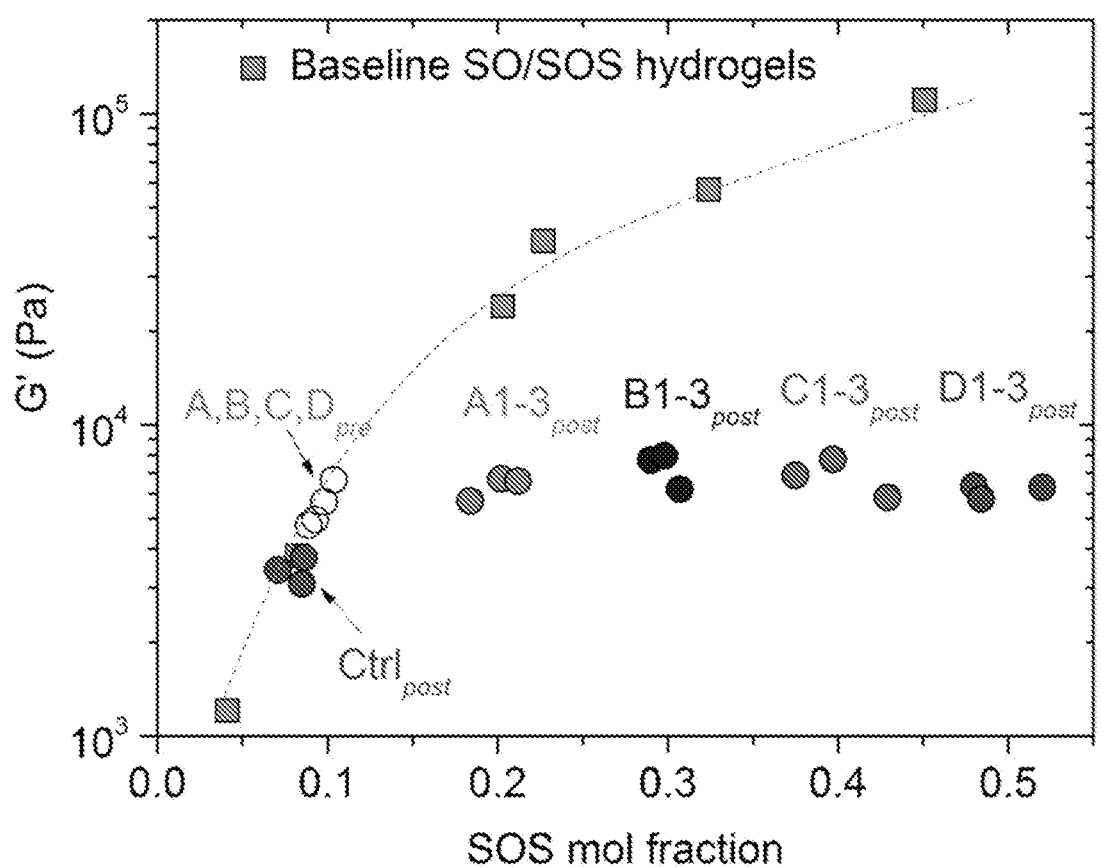
FIG. 22. Elastic moduli under dynamic shear ($\omega=1$ Hz) as a function of total SOS triblock copolymer composition.

FIG. 22 shows the pre-click and post-click elastic moduli of hydrogels formed from the four blends A through D. The elastic moduli of the six SO/SOS TPE hydrogels were also included for direct comparison of the post-click DN hydrogels with baseline hydrogels of similar SOS content. As a control experiment, baseline SO/SOS hydrogels (no azide or alkyne functionality present) with approximately 8.5 mol % SOS triblock copolymer were soaked in argon-degassed catalyst solutions for the standard 24-hour reaction time. Their elastic moduli were also included in FIG. 22. The control samples established the effect of the catalyst solution on the mechanical properties of the hydrogel independent from the SOS tethers. As shown in FIG. 22, the elastic moduli after catalyst solution exposure remained very similar to that of the unexposed 8.5 mol % baseline hydrogel (original frequency sweep data is provided in the supplementary information). Thus, the impact of the catalyst solution exposure on elastic modulus was regarded to be negligible.

The effect of adding azide and alkyne chain end functionality (unreacted) towards the elastic modulus of the hydrogel appears to be largely minimal. Examples of the elastic moduli of the four blends before adding catalyst solution fell along the trajectory for the baseline SO/SOS hydrogel systems. That is, the chain end functionality in its uncoupled state has not limited the elastic properties of the hydrogels under dynamic shear.

A comparison of the elastic moduli of hydrogels under dynamic shear, containing azide/alkyne functional groups both pre- and post-click reveals an apparent increase in elastic modulus (20 to 40%) upon installation of additional SOS triblock copolymer. Compared with baseline TPE hydrogels of similar total SOS triblock copolymer compositions, these increases in modulus (from introducing the second network of tethers) were modest. For example, adding tethers post-swelling to get from 8.9 mol % SOS to 48 mol % SOS triblock copolymer (sample D1) increased the elastic modulus from 4.7 to 6.3. By comparison, baseline SO/SOS hydrogels with 45.1 mol % SOS triblock copolymer in which the entire population of tethers were introduced during melt-state self-assembly exhibits an elastic modulus of just over 100 kPa. This comparison underscored the very limited impact the secondary network, installed post-swelling, had on the small strain shear response of these hydrogels. At small oscillatory strains (<3%), the secondary network, containing almost four times the number of tethers as the primary network, remained largely passive. This is a direct reflection of the stress free environment under which these tethers are installed. The elasticity of these hydrogel networks was governed predominately by PEO coronal overlap with adjacent spherical domains. The small improvement in elastic modulus was likely a product of the changes in how adjacent coronal layers are connected, without a pronounced difference in coronal layer overlap, the changes detected remain quite modest.

Figures 23A, 23B:
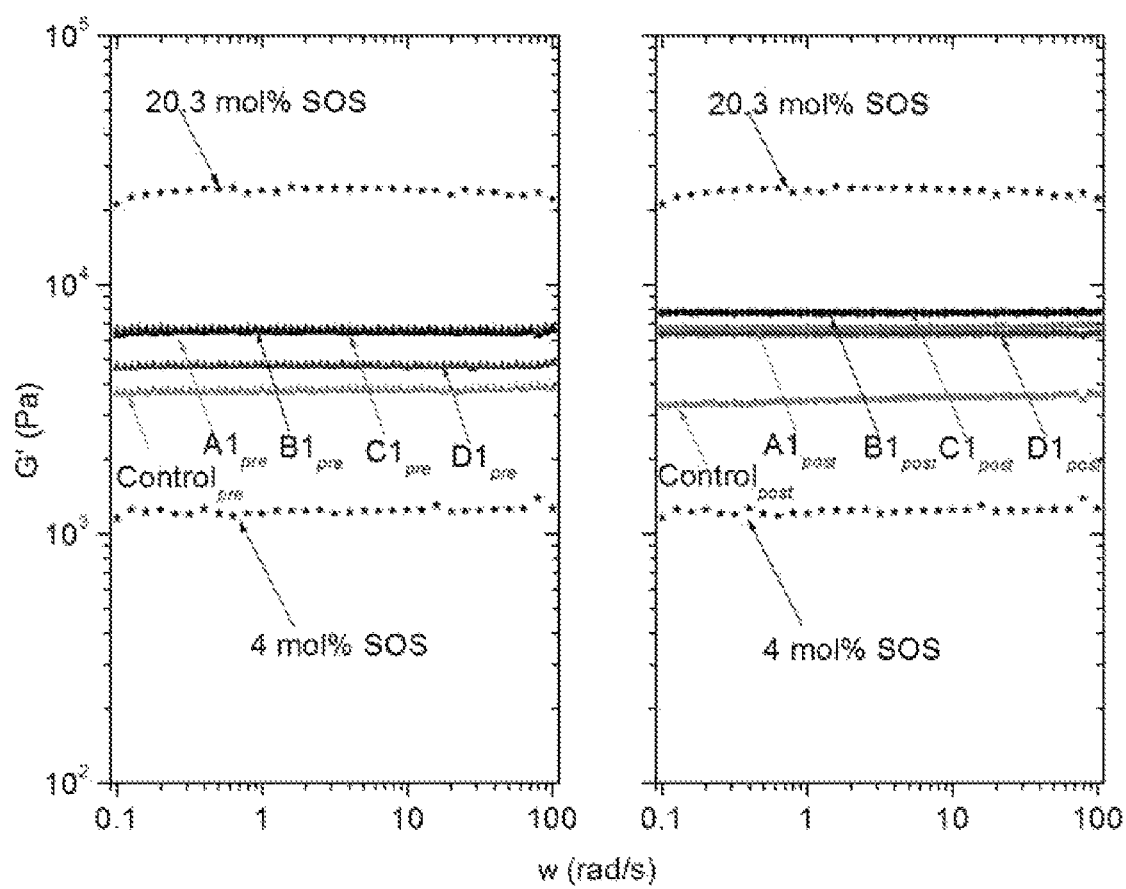
FIG. 23. Representative dynamic frequency sweep results showing the elastic moduli for samples A1-D1 before testing (FIG. 23A) and after testing (FIG. 23B), two baseline SO/SOS hydrogels of 4.1 and 20.3 mol % SOS, and a baseline SO/SOS hydrogel soaked in catalyst solution for 24 hours (control).
Figure 24:
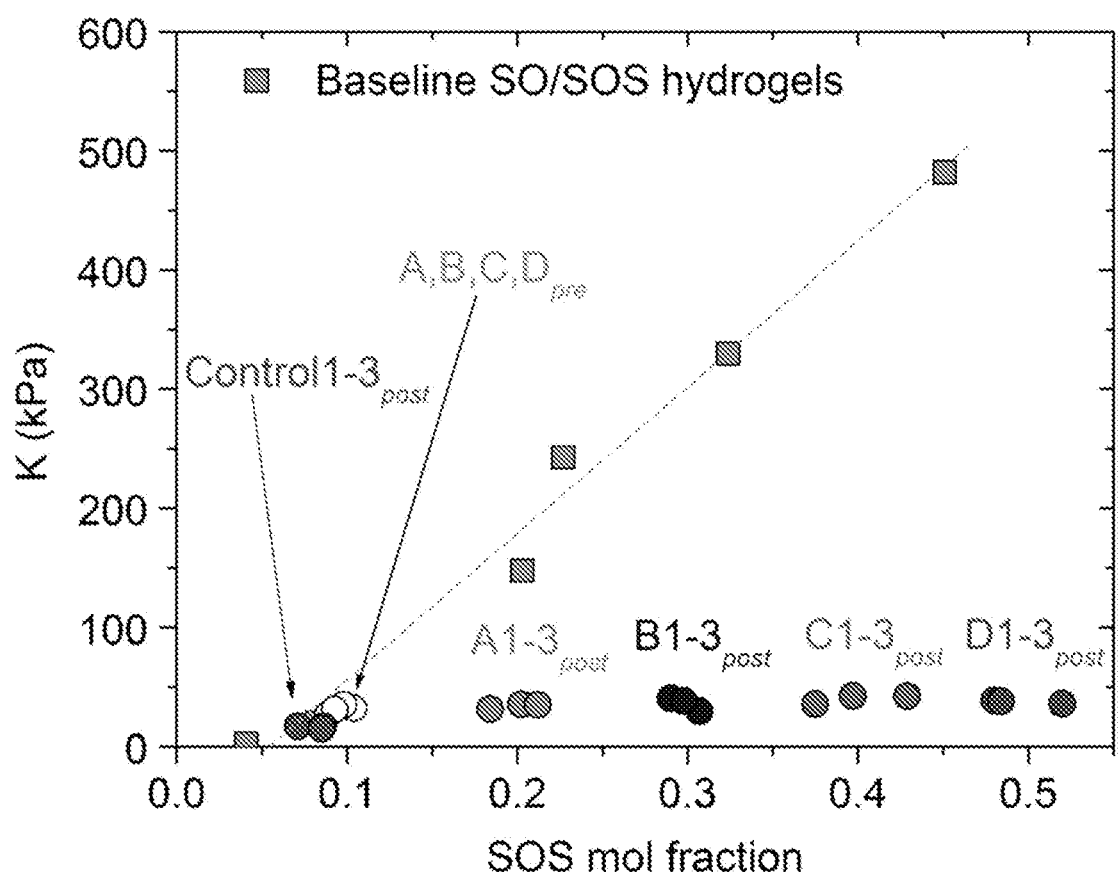
FIG. 24. Compressive moduli in unconfined compression (strain rate=20% min$^{-1}$) as a function of the total SOS triblock copolymer composition.

The behavior of the post-click DN hydrogels in unconfined compression (to 40% strain) produced similar conclusions (FIGS. 23 and 24). As with the baseline SO/SOS hydrogels, all samples, regardless of treatment, produced linear stress-strain relationships to 40% strain (strain rates at 20% $min^{-1}$) and exhibited some hysteresis during decompression, but ultimately showed complete elastic recovery with second compression/decompression cycles coinciding the first cycle. Baseline SO/SOS control samples exposed to catalyst solutions for the 24-hour reaction time performed similarly to unexposed baseline hydrogels. Pre-click samples gave compressive moduli consistent with those produced by baseline SO/SOS hydrogels of similar SOS triblock copolymer compositions. The installing additional SOS triblock copolymer post-swelling resulted in small increases in compressive modulus across samples compared with their pre-click counterparts, but as with elastic modulus, the increase was very modest when compared with baseline SO/SOS hydrogels of similar total SOS content.

Figure 25A:
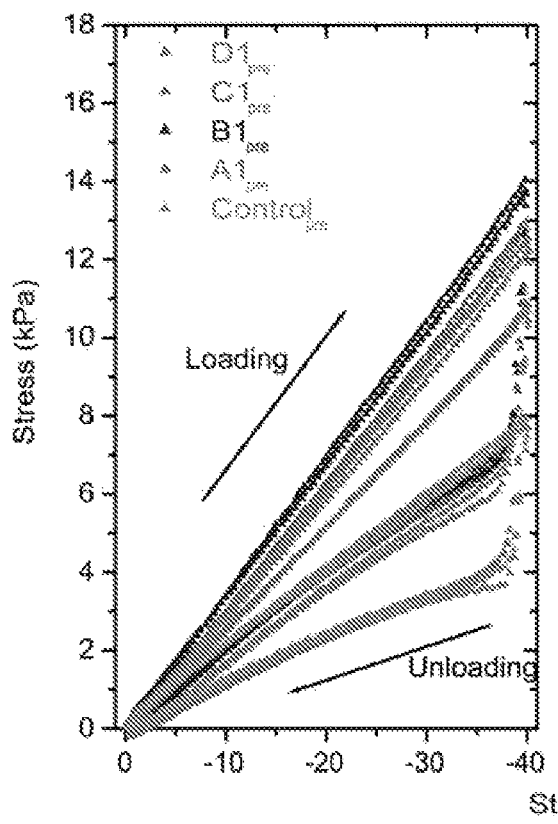
FIG. 25. Representative unconfined compression results showing the stress-strain relationships for samples A1-D1 before testing (FIG. 25A) and post-testing (FIG. 25B), and a baseline SO/SOS control hydrogel soaked in catalyst solution for 24 hours (control).
Figure 25B:
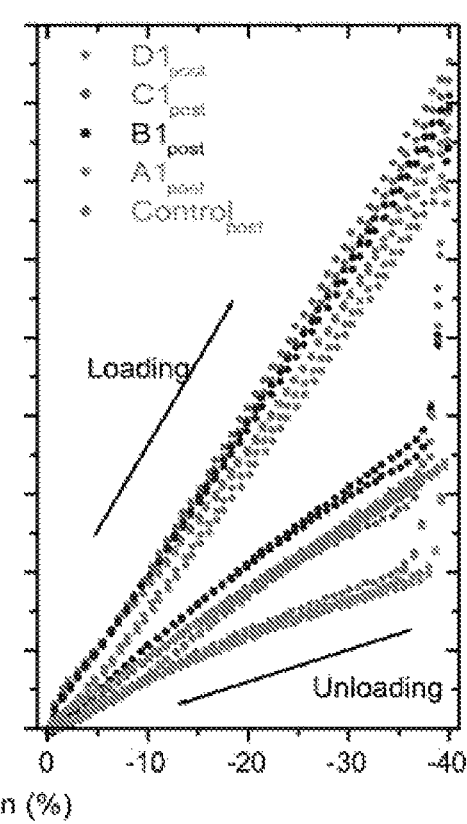

Using sample D1 as an example, the pre-click (8.9 mol % SOS) and post-click (48.0 mol % SOS) compressive moduli were 27 kPa and 38 kPa respectively, demonstrating the marginal effect of the secondary SOS network on compression response of the hydrogel. By comparison, the baseline SO/SOS hydrogel of 45.1 mol % SOS exhibited a compressive modulus of 482 kPa. The post-click DN data suggested that even at 40% compression, the secondary network of SOS tethers still failed to engage to an extent that allowed it to contribute significantly to the mechanical response of the hydrogel, even with four times as many tethers as the primary network. The SOS triblock copolymer of the primary network introduced during melt-state self-assembly was still the dominant factor determining compressive properties. Original compression data for the baseline SO/SOS control samples, as well as the pre- and post-click samples A1-D1 are included in FIG. 25.

Example 17—Tensile Testing of Swollen Hydrogels

Tensile tests were carried out on rectangular pieces of hydrogel samples prepared according to Example 15 cut to about 14-mm width with thickness that varied from 0.442 mm to 0.875 mm. Multiple test coupons were cut from each hydrogel disk to maximize sample size within a letter group (e.g., disks B1, B2 and B3 produced six viable test coupons). All tensile tests were run at room temperature using the normal force transducer of a TA ARES rheometer. TA rectangular torsion geometry test fixtures were used as tensile test grips with added 600 grit sand paper. A strain rate of 5 mm/s was applied until complete hydrogel fracture. The strain rate was chosen to minimize slip while ensuring the maximum travel distance could be covered in less than 0.5 minutes, such that surface evaporation during testing could be minimized. Stress was calculated as the force normalized by the initial cross sectional area of each sample (engineering stress).

Figure 26:
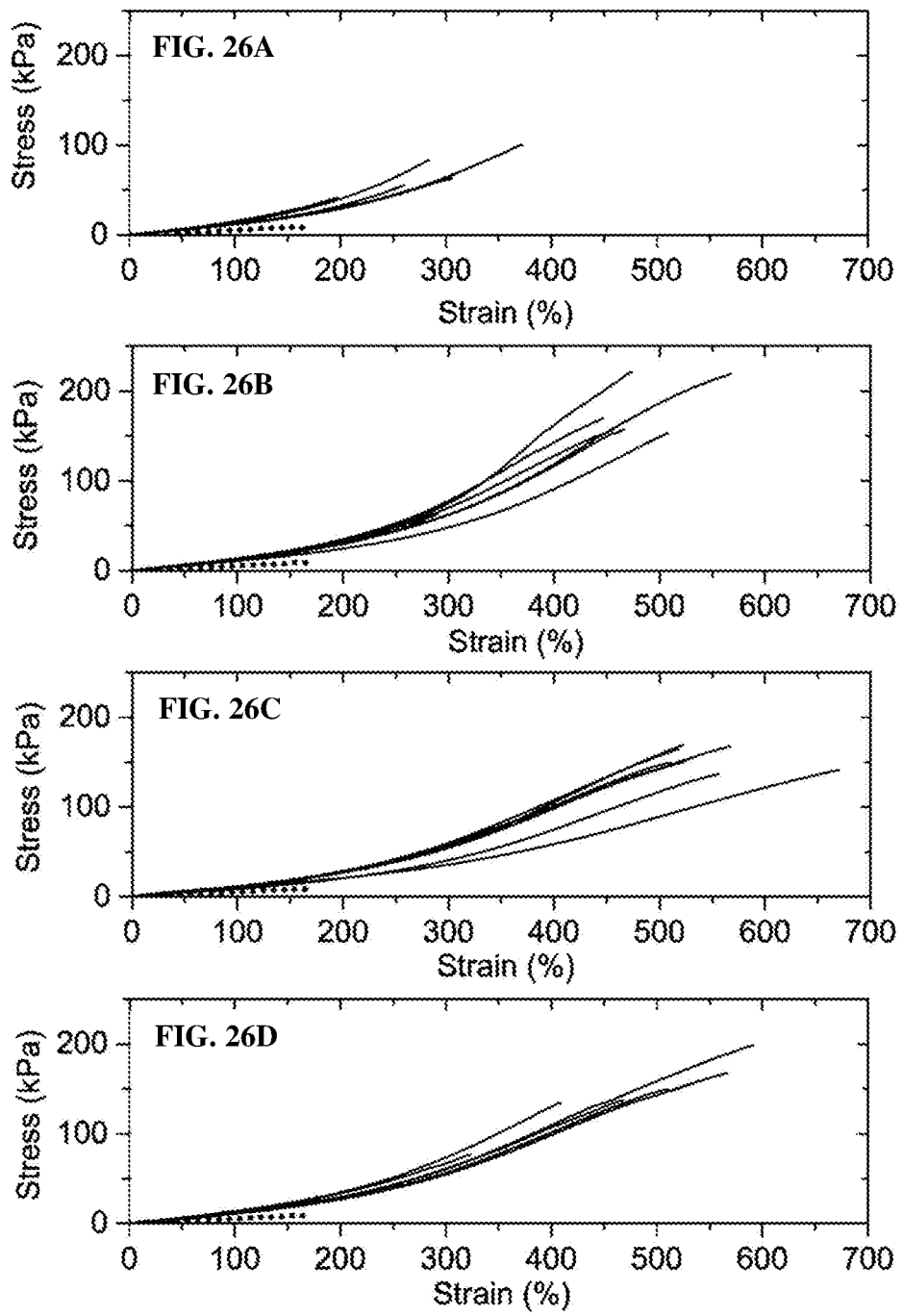
FIGS. 26A-D. Tensile test results for hydrogels formed from blend A (FIG. 26A), blend B (FIG. 26B), blend C (FIG. 26C), or blend D (FIG. 26D), evaluated after installation of the secondary network of SOS triblock copolymer. Total SOS triblock copolymer compositions can be found in Table 3.

The secondary network of SOS tethers provided a stunning enhancement in hydrogel fatigue resistance possible while maintaining very high Q values. FIG. 26 shows the tensile tests from a series of post-click DN samples A through D. Multiple test coupons could be tested from each sample disk (i.e. disks B1, B2 and B3 produced six viable test coupons) and combined to produce the four plots of FIG. 26. Similar control experiments on baseline SO/SOS hydrogels exposed to the catalyst solution for 24 hours, as well as pre-click blends A through D, showed tensile behavior similar to that expected for baseline SO/SOS hydrogels of similar SOS content. The post-click blends A through D showed dramatic improvements in virtually all tensile property categories. Tensile test results for the unmodified baseline 8.5 mol % SOS hydrogel of similar Q, but without the clicked functional groups underscore the dramatic improvements in fatigue resistance possible.

Table 4 summarizes the basic tensile properties for each of the hydrogel blends A through D, with analogous data for the performance of the baseline SO/SOS hydrogels. Each hydrogel formed from blends A through D has a swelling ratio in the range of 18-20 g $H_2O$/g polymer, and was therefore comparable with the 8.5 mol % SOS baseline hydrogel.

TABLE 4

Mechanical properties of baseline TPE hydrogels and post-click DN hydrogels.

| Sample | $SOS_{post}$ (mol %) | Q (g water/g polymer) | Strain to break (%) | Stress to break (kPa) | Young's modulus (kPa) | Fatigue resistance (kJ/m$^3$) |
|---|---|---|---|---|---|---|
| Baseline | 4.1 | 26.9 | — | — | — | — |
| SO/SOS | 8.5 | 20.7 | 154 | 8.7 | 5.3 | 6.2 |
| Hydrogels | 20.3 | 9.3 | 375 | 107 | 38 | 203 |
|  | 29.2 | 7.9 | 293 | 150 | 82 | 246 |
|  | 32.4 | 7.0 | 254 | 160 | 110 | 240 |
|  | 45.1 | 5.7 | 195 | 237 | 209 | 280 |
| A | 20.0 ± 1.2 | 18.5 ± 1.0 | 287 ± 58 | 68 ± 21 | 12.0 ± 1.5 | 74 ± 33 |
| B | 28.1 ± 3.6 | 18.3 ± 0.7 | 458 ± 85 | 163 ± 53 | 12.5 ± 1.2 | 269 ± 116 |
| C | 38.1 ± 4.4 | 18.8 ± 0.4 | 567 ± 56 | 169 ± 34 | 11.2 ± 1.5 | 361 ± 93 |
| D | 49.1 ± 3.0 | 19.2 ± 0.7 | 479 ± 103 | 135 ± 30 | 13.1 ± 1.2 | 276 ± 127 |

Figure 27:
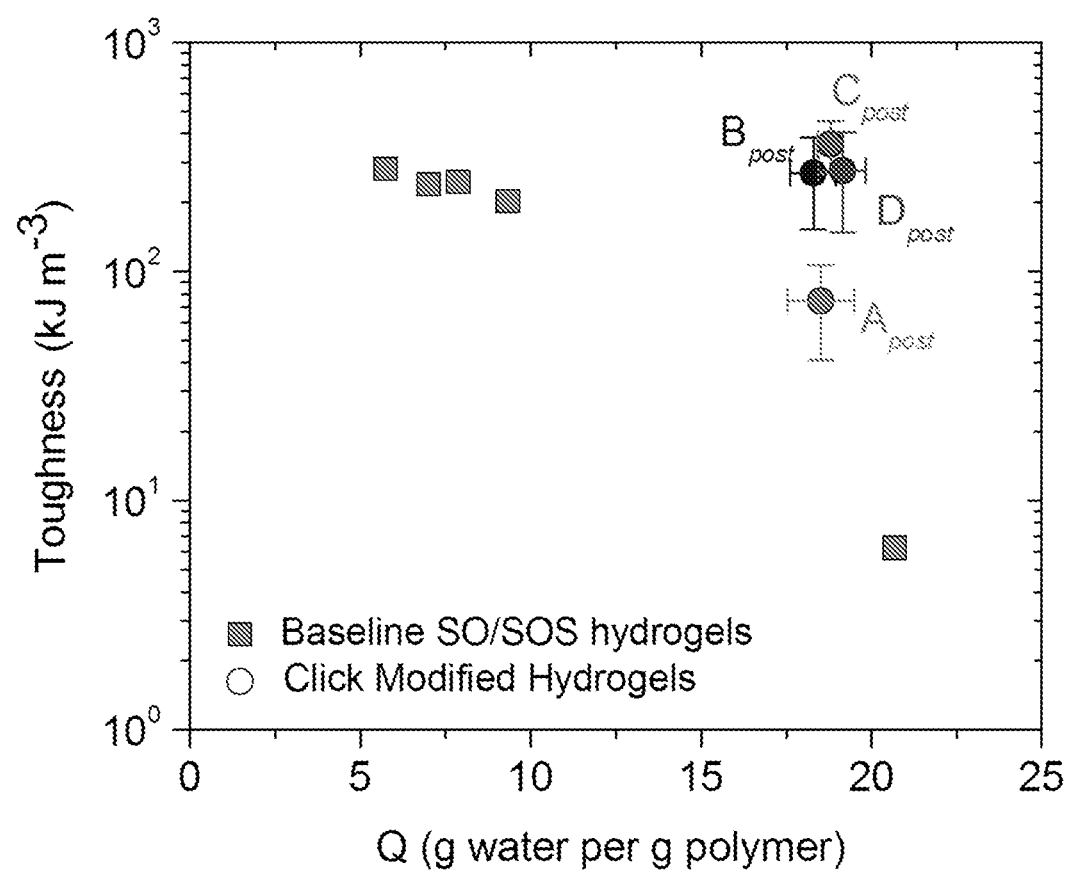
FIG. 27. Hydrogel fatigue resistance (toughness) as a function of Q. The fatigue resistance and Q data can be found in Table 4.
Figure 28:
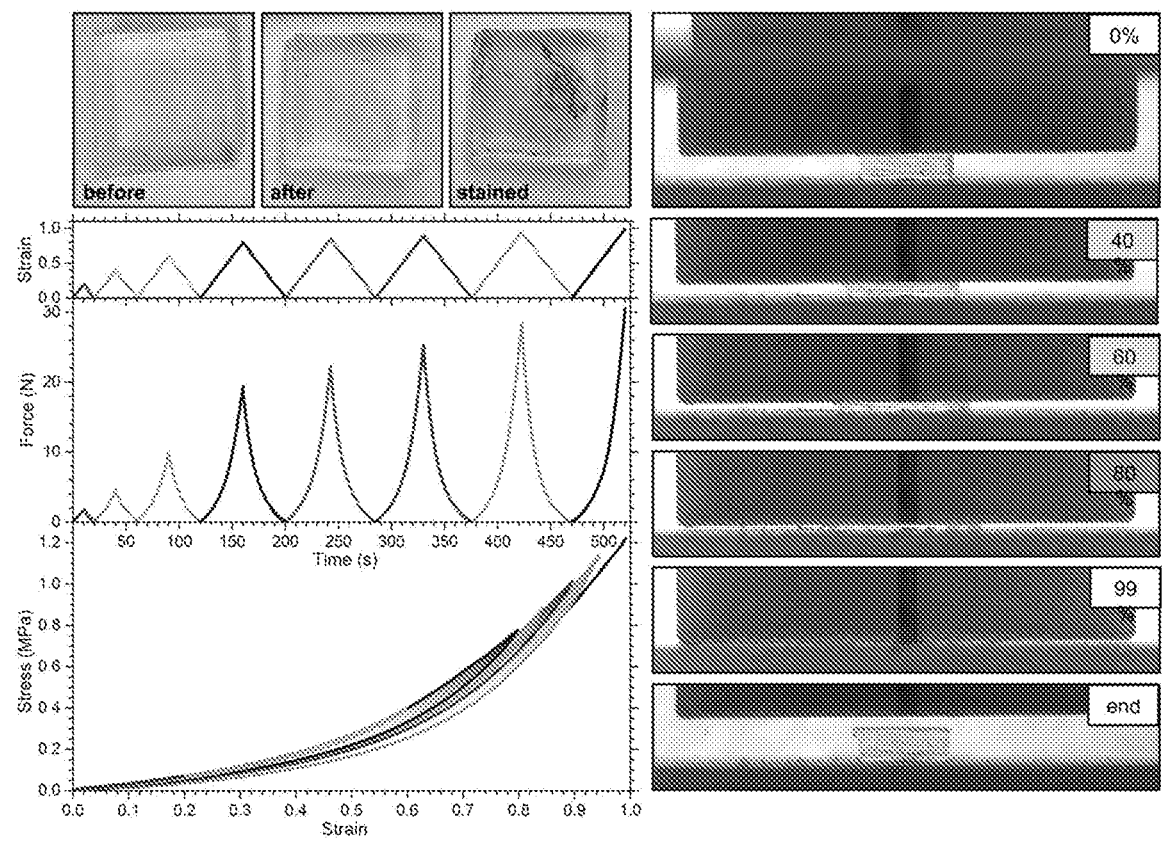
FIG. 28. Example of an SO/SOS hydrogel composed of 61 mol % SOS swollen with phosphate buffered saline (PBS) and subjected to unconfined compression at a rate of 2% strain/s to about 20% strain, and then a return to 0% strain at the same rate. Successive cycles increased the final strain to about 40%, about 60%, about 80%, about 90%, about 95%, and about 99% strain. The images above and to the right show that the square sample (5 mm×5 mm) remained intact, without catastrophic failure typical of most hydrogel systems.
Figure 29:
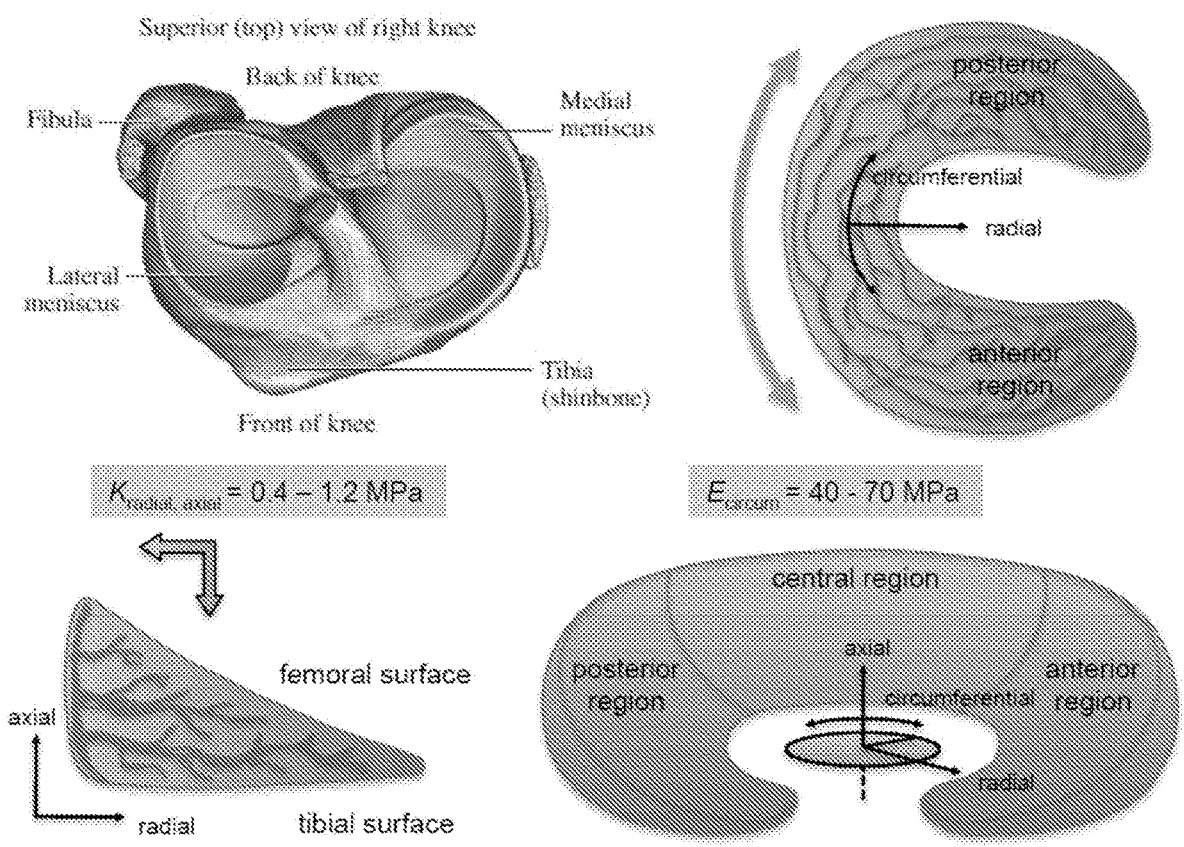
FIG. 29. The knee meniscus is characterized by dramatic spatial and directional differences in the tensile and compressive moduli. The tensile modulus in the circumferential direction ($E_{circum}$=40-70 MPa) is almost two orders of magnitude greater than the compressive modulus ($K_{rad, axial}$=0.4-1.2 MPa) in the axial or radial directions, due largely to type I collagen fibers that align predominantly in the circumferential direction and improve strength in tension.

Table 4 and FIG. 27 show that adding the secondary network vastly improved both fatigue resistance and stress to break. With only a single, primary network of SOS tethers, the 8.5 mol % SOS hydrogel (~95% $H_2O$ by mass) could absorb 6.2 kJ m$^{-3}$ before fracture at stresses as low at 8.7 kPa. With the secondary network of tethers, both the fatigue resistance and stress at break could be improved dramatically, with samples from blend C reaching mean values of 361 kJ m$^{-3}$ (a 58-fold increase) and 169 kPa (a 19-fold increase), respectively. Similarly, the secondary network of SOS tethers significantly improved strain to break (2- to 3-fold) and Young's modulus (2-fold) compared with the 8.5 mol % SOS baseline hydrogel of equivalent Q value. Incredibly, the secondary network, even at the moderate levels produced in the B blends, provides hydrogels with Q values of 18-20 g $H_2O$/g polymer the tensile properties typically available only to hydrogels of much lower water content.

Without wishing to be bound by theory, the dramatic impact of the secondary SOS network under tension (compared to small strain shear or unconfined compression) was a product of its ability to reinforce the primary network at higher strains. Because it is largely formed in an unperturbed state, the topological entanglements of the secondary network required much higher strains to become mechanically engaged. As such, they provided the hydrogel network an improved range over which strain energy can be absorbed. That is, as the primary network approached its mechanical limit, it gradually transferred load to the secondary network, extending the strain and stress to break. Consequently, the additional tethers improved the elongation capacity of the hydrogels. Overall, the post swelling click chemistry provided a means of adjusting the tensile properties of these tethered micelle based hydrogels largely independent of other mechanical properties.

The stress-strain plots in FIG. 27 gave a sense of the scatter in the tensile response typical given simple melt-pressing under atmospheric conditions. Thus, the measured tensile properties were likely influenced by bubble, grain boundary and edge defects present before and after swelling. As a consequence, the vast improvements in tensile properties were likely understated.

Unlike traditional DN hydrogels, the first and second networks in this diblock-triblock system derived from the same molecular constructs, with the elements of the second network intrinsically present, yet dormant until activated. The strategy preserves the chemical composition of the hydrogel while employing a stepwise installation process to form two chemically identical tethering populations, each under a different degree of mechanical (osmotic) stress. With the exception of the Cu(I) catalyst here, forming secondary network by this route could potentially eliminate concerns associated with leaching in traditional DN hydrogel systems.

Example 18—General Procedure for Forming Hydrogel Membranes

The press was set to 150° C. A mixture of PS-PEO (SO, Example 3) and PS-PEO-PS (SOS, Example 4) was placed into a mold between two Kapton™ sheets and pressed at 500 psig for 5 minutes, at which point the SO-SOS melt was removed.

To reduce bubbling and cracking, the assembly was placed it into a vacuum bag and repressed at the same pressure, temperature, and time while applying vacuum using a membrane pump. This process was repeated until no bubbles were visible, typically requiring 2 to 4 cycles of removing the sample, letting the sample cool to room temperature, and placing it back into the press for another run under vacuum. Once the process was completed, the sample was removed from the mold, excess material was trimmed, and the sample was swelled in water or aqueous buffer for at least 24 hours.

Using a processing temperature 100° C. or cooler took longer, but the same effect was obtained. The higher pressure (500 psig) seemed to speed up the process on the removal of bubbles. Without wishing to be bound by theory, the repeated cycling process may concentrate the polymer into a smaller volume.

Example 19—Hydrogel Recovery After Extreme Compression

Figure 30:
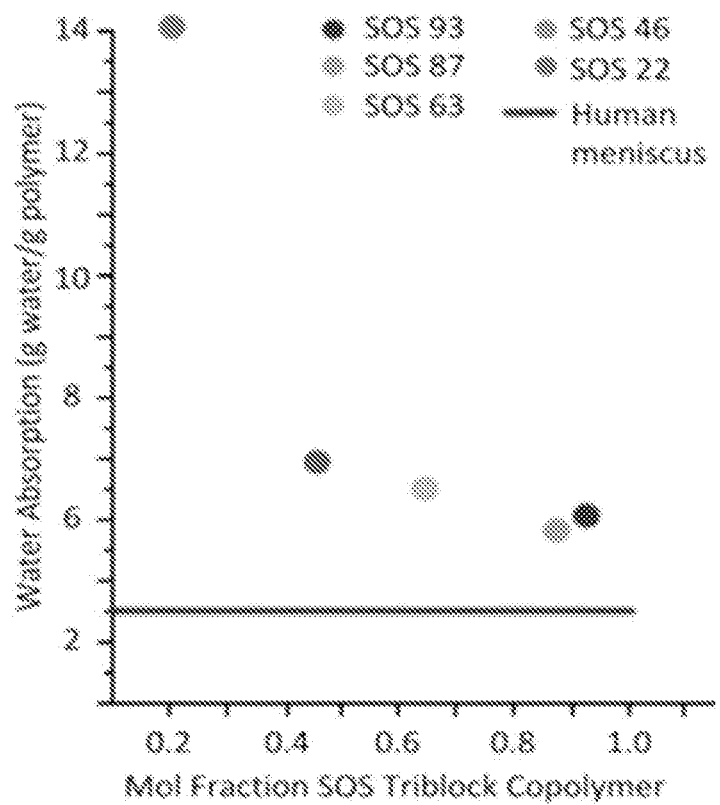
FIG. 30. Plot comparing water absorption (g water/g polymer) as a function of the mol fraction SOS triblock copolymer for SOS93, SOS87, SOS63, SOS46, and SOS22, to the human meniscus (horizontal line at 3:1 water absorption).

An SO/SOS hydrogel composed of 61 mol % SOS swollen with phosphate buffered saline (PBS) was subjected to progressively higher loadings under unconfined compression, as shown at FIG. 30. The first cycle consisted of compression at a rate of 2% strain/s to about 20% strain, and then a return to 0% strain at the same rate. Successive cycles increased the final strain to about 40%, about 60%, about 80%, about 90%, about 95%, and about 99% strain. As shown in the images above and to the right in FIG. 30, the square sample (5 mm×5 mm) remained intact, without catastrophic failure typical of most hydrogel systems. Additionally, cycles confirmed no cycle-to-cycle hysteresis to 60% strain, and minimal cycle-to-cycle hysteresis at strains above 60%.

The origin of the hysteresis in this sample was small crack formation at about 70% strain. Crack propagation appears to be suppressed such that additional damage is limited at higher strains. As the stained image shows, fracture appears to have occurred at an isolated location in the hydrogel, and remained localized to the original fracture location. The absence of microcracks at other locations in the hydrogel suggested that fracture was initiated at a localized defect and was not a product of material limitations in the absence of such stress concentrations.

This experiment was performed on a square sample, for which significant in-plane stresses in the non-radial directions were produced, and which may be the impetus for the original crack initiation event. It is believed that the square sample fractured because of the lateral shear stresses the sample feels to due to the asymmetry in its shape. In a similar compression experiment using a circular sample, two successive cycles to 99% progressed with no damage and perfectly overlapping stress strain behavior.

Regardless, the hydrogel averted catastrophic failure through suppression of crack propagation as a result of the structure's ability to intrinsically redistribute stress. The hydrogel can be compressed to 99% strain (1/100th of its original thickness) without failure. Most hydrogels fracture catastrophically at compressions much less than 80%.

Figure 68:
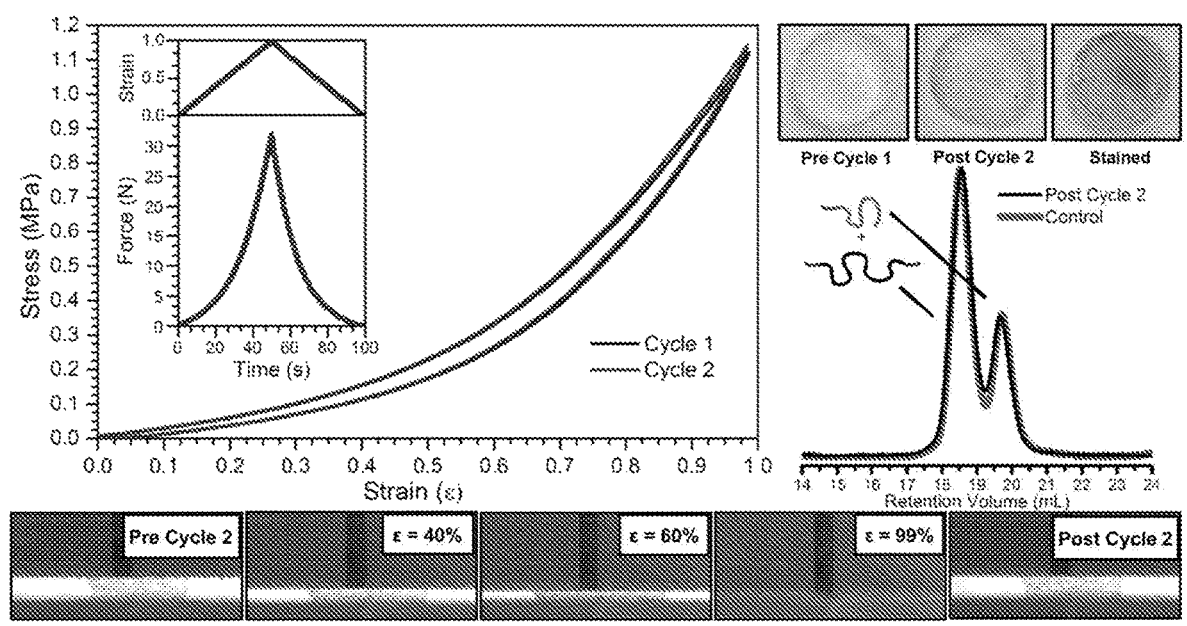
FIG. 68. Overlay of the stress versus strain data from two successive compression cycles to 99% strain (strain rate=2% $s^{-1}$) for a hydrogel (6 mm×1.6 mm, 85 wt % phosphine buffered saline (PBS)) containing 61 mol % SOS triblock copolymer submerged in a phosphate-buffered saline (PBS) bath during testing.

FIG. 68 shows the overlay of the stress versus strain data from two successive compression cycles to 99% strain (strain rate=2% s$^{-1}$) for a hydrogel (6 mm×1.6 mm, 85 wt % phosphine buffered saline (PBS))) containing 61 mol % SOS triblock copolymer, submerged in a phosphate-buffered saline (PBS) bath. SEC data confirmed no change in molecular weight distribution in the constituent block copolymers comprising the hydrogel following consecutive compression cycles. Staining with India ink confirmed the lack of visible crack formation. Video stills (bottom of the figure) depicted the progression of the second compression cycle.

Example 20—Comparison of Hydrogels with Human Meniscal Tissue

Figure 31:
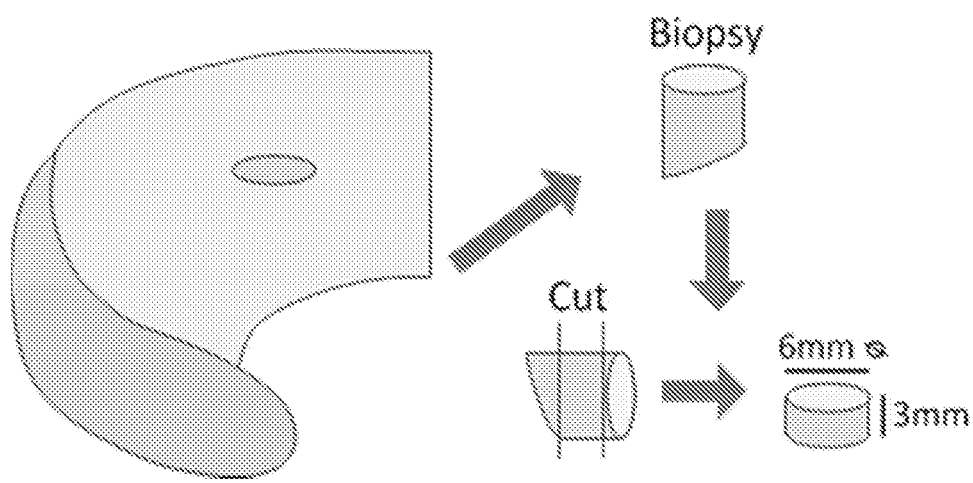
FIG. 31. Process for sectioning human and sheep menisci.

Menisci from seven frozen human cadaveric specimens and five ovine cadaveric specimens were sectioned into medial and lateral anterior and posterior segments and slow thawed in 1× phosphate buffer saline (PBS) solution. Plugs were created using 5 mm diameter biopsy punch taken from the proximal to distal ends and stored at 1.6° C. in 1×PBS for 24 hours to allow equilibrium swelling to occur (FIG. 31). As many plugs as the tissue size allowed where used for each region of interest. A tissue sizing apparatus was used to cut the samples 3 mm thick from the mid-belly of the plug. A total of 10 samples for all regions were tested for human with the exception of the medial human where only 9 samples were tested due to limited tissue. Sample sizes for sheep menisci are as follows: medial lateral n=5, lateral posterior n=6, medial anterior n=8, medial posterior n=8

Hydrogels where created using aluminum cylindrical molds per Example 7. Specifically, the SO/SOS block copolymer was packed between two Kapton™ sheets, melt pressed in a Carver Press (150° C., 500 psi, 10 minutes), and allowed to swell in 1×PBS for 24 hours before testing. Mold dimensions were selected such that the swollen cylindrical plugs where 3-mm thick and 5-mm in diameter. A total of 10 hydrogels were tested.

Samples were mounted between two polished aluminum platens in a heated 1×PBS bath (96-99° F.) and tested using a servo hydraulic testing system (Bionic™ Model 370.02 MTS) equipped with a 2-lb. load cell (Futek™ LSB200) for measuring axial force. The average thickness was measured using calipers and after a 200-mN preload samples were compressed to 12% strain for 5000 cycles at 1 Hz, representing physiological strains, frequency, and the average daily steps taken by U.S. Americans. After initial testing, samples were stored at 1.6° C. in 1×PBS for 24 hours, after which the testing protocol was repeated.

A custom MATLAB (Mathworks, Natick, Mass.) program assessed the data. Modulus values were determined from a linear fit of the 2-10% stress strain curve of each loading cycle. A second order power fit of the modulus versus cycle graph assessed relaxation. A one way analysis of variance (ANOVA) with a post hoc Tukey's test assessed differences between the two runs of a single plug and between groups with values of interest including cycle 1, cycle 10, cycle 25, cycle 50, the final 5000$^{th}$ cycle, and the three coefficients from the power fit (coefficients A, B, and C). Significance was set at p<0.05.

Figure 32:
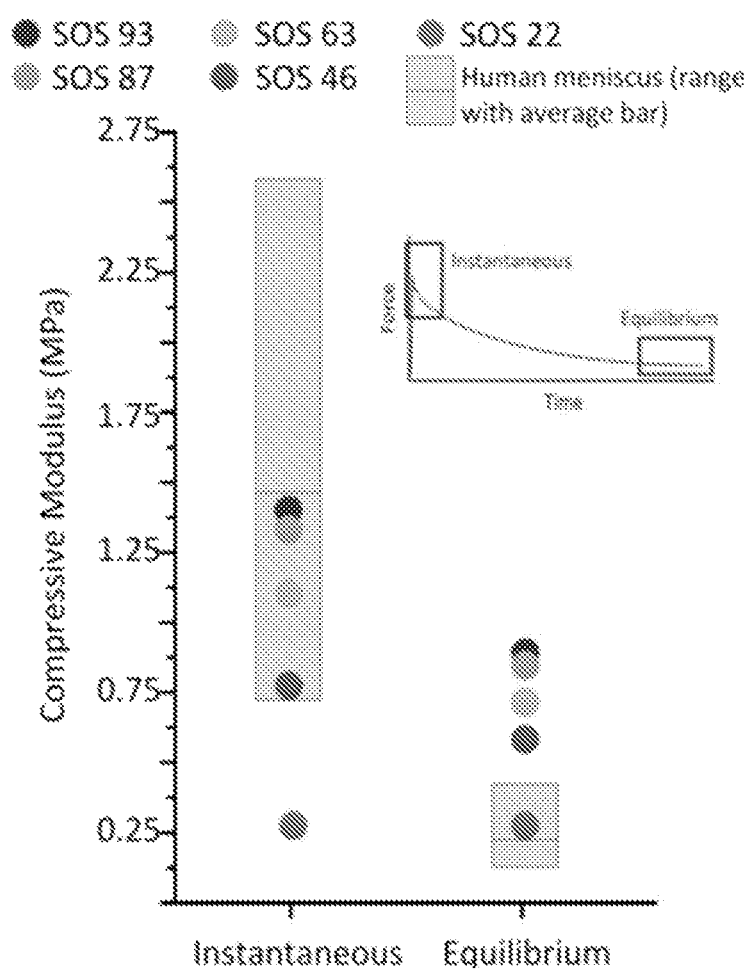
FIG. 32. Plot comparing comparative modulus (MPa) as a function of instantaneous equilibrium for SOS93, SOS87, SOS63, SOS46, and SOS22. The ranges for the modulus of the human meniscus are shown as gray boxes.
Figure 33:
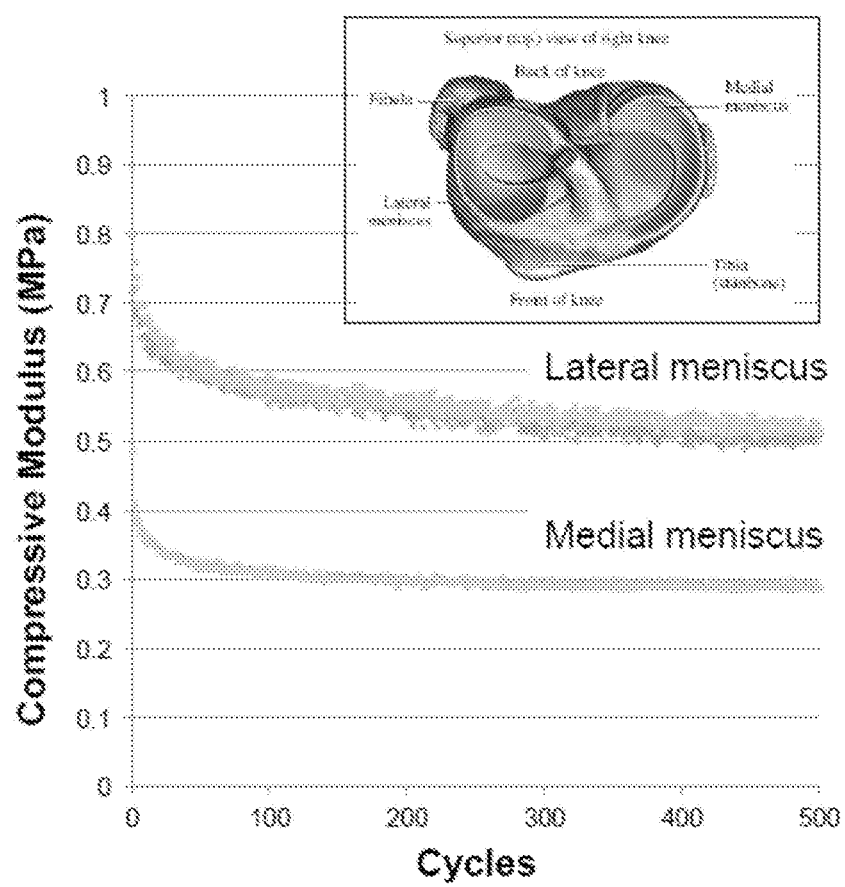
FIG. 33. Mechanical response under cyclic loading for human meniscal tissue. Compare to the mechanical responses at FIG. 11 for the hydrogels disclosed herein.

Indentation relaxation testing was performed to physiological strains of 12% and showed that adjusting the amount of triblock copolymer in the hydrogel altered the compressive properties to be in the same range as human meniscal compressive properties (FIG. 32). The hydrogel network was also tuned to exhibit a modulus and behavior comparable to that of human meniscal tissue. As can be seen by comparing FIGS. 11 and 42, the magnitude and relaxation in the compressive modulus under cyclic loading by hydrogel blends of (22, 46, and 72 mol %) triblock copolymer and the medial and lateral meniscus.

Figure 34A:
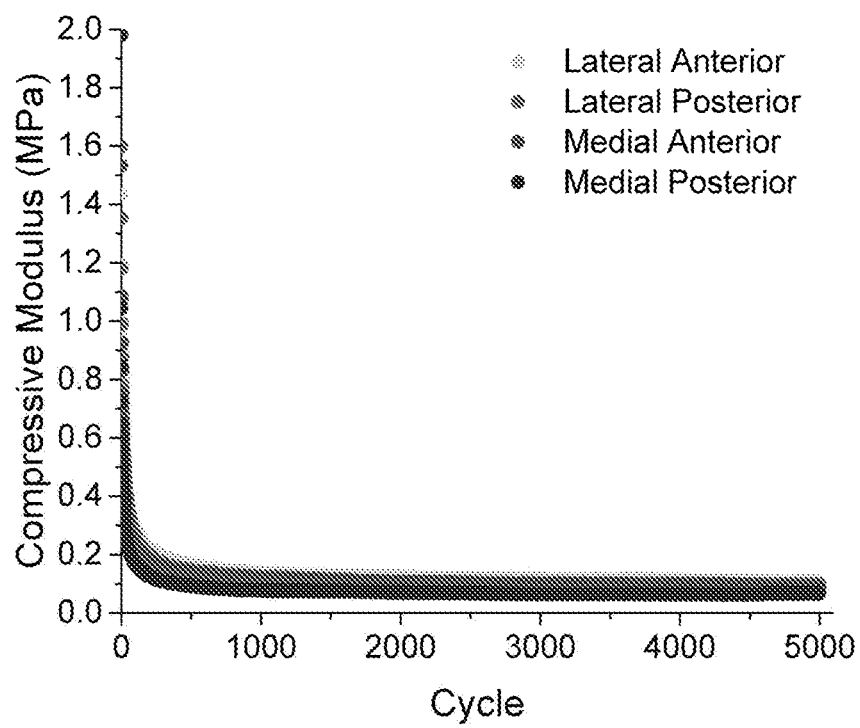
FIG. 34A. The average compressive modulus values for all 5000 cycles for the human meniscus in each region of interest (lateral anterior, lateral posterior, medial anterior, and medial posterior). The first 500 cycles from the FIG. 34A are shown in FIG. 34B.
Figure 34B:
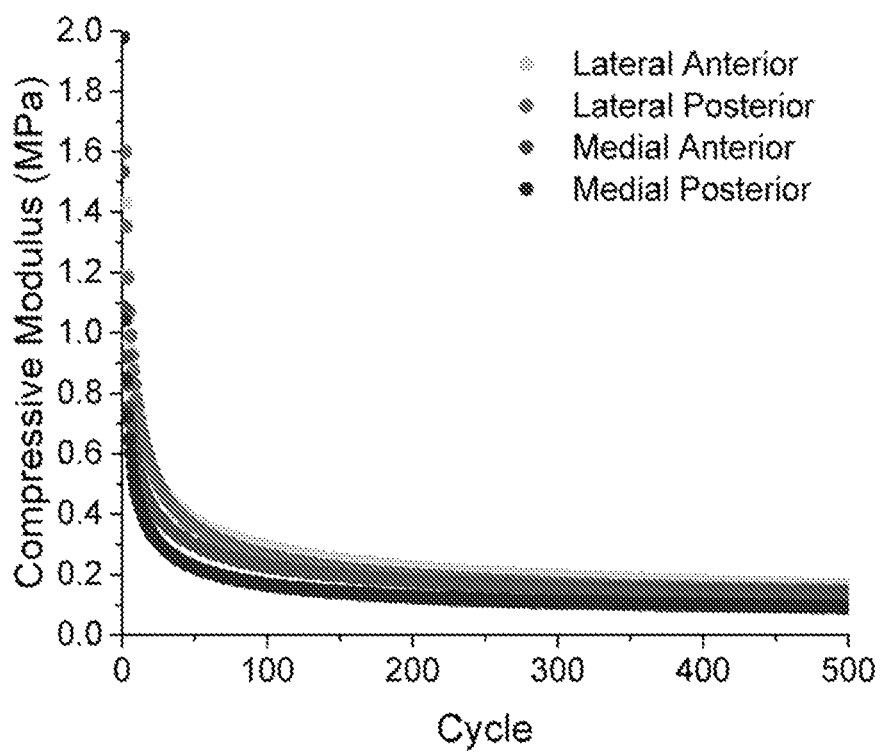
Figure 35A:
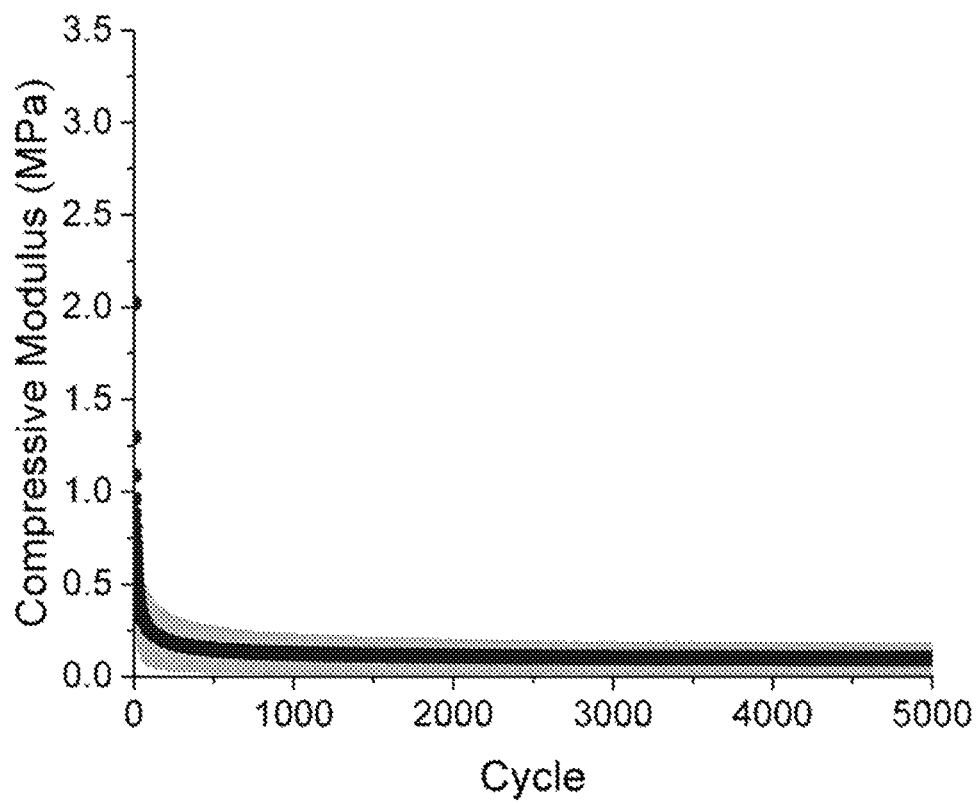
FIGS. 35A&B. The compressive modulus values for the human meniscus averaged for all regions of interest.
Figure 35B:
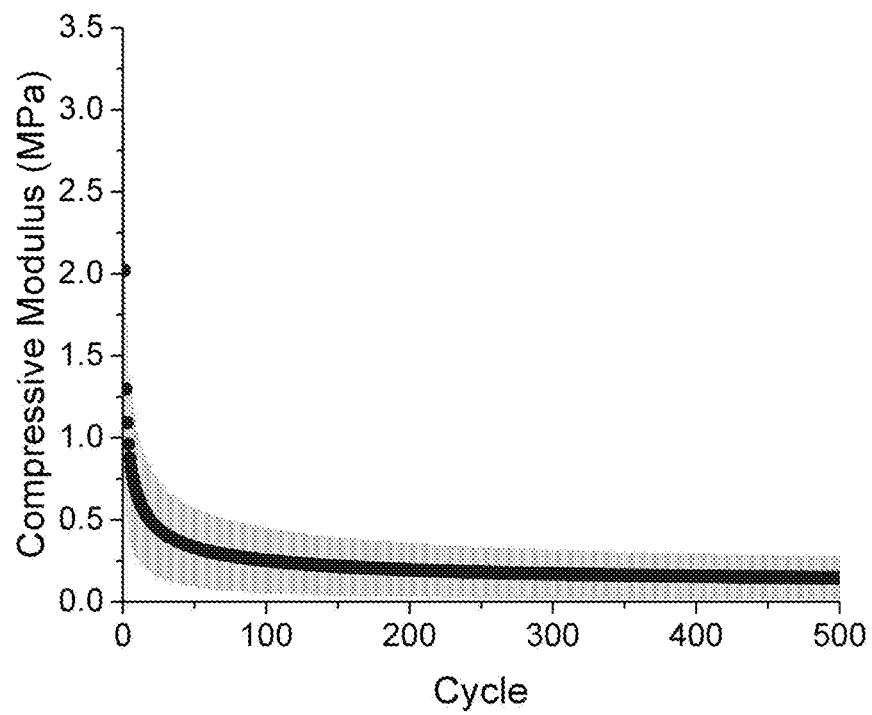
Figure 36A:
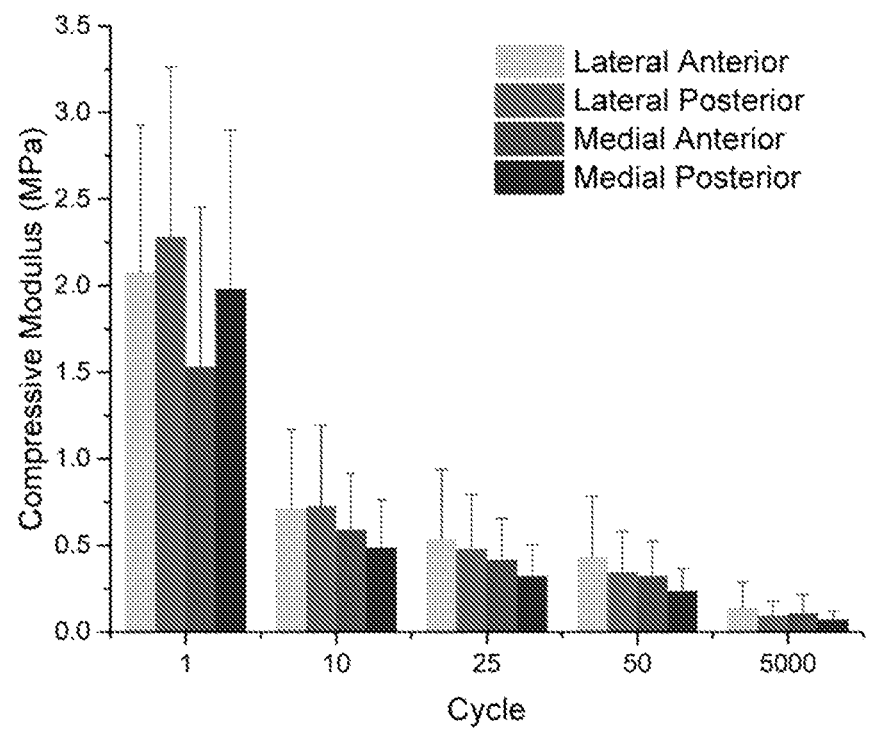
FIG. 36A. Representative cycles (1, 10, 25, 50, and 5000) for the human meniscus in each region of interest.
Figure 36B:
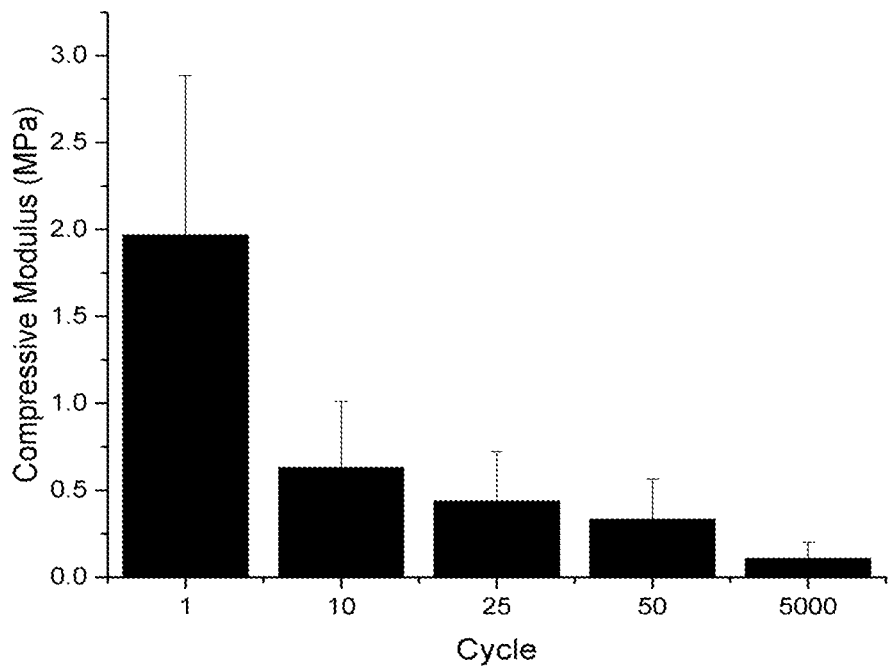
FIG. 36B shows the data from FIG. 36A averaged across all regions.
Figure 37A:
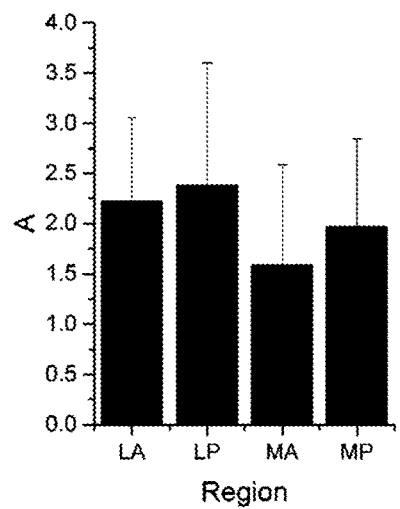
FIGS. 37A-C. The average values for the three coefficients of the power fit (A, B, C, respectively) for the human meniscus broken down by region of interest.
Figure 37B:
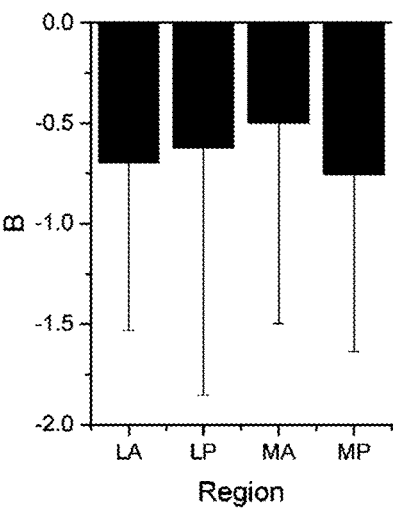
Figure 37C:
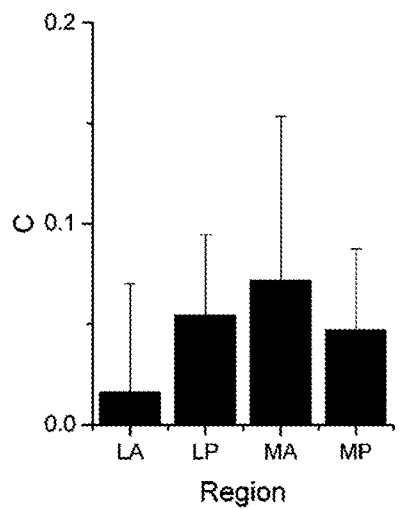

FIG. 34A shows the average compressive modulus values for all 5000 cycles for the human meniscus in each region of interest (lateral anterior, lateral posterior, medial anterior, and medial posterior). The first 500 cycles from the FIG. 34A are shown in FIG. 34B. FIGS. 35A&B show the compressive modulus values for the human meniscus averaged for all regions of interest. FIG. 35A shows all 5000 cycles and FIG. 35B shows only the first 500 cycles of the test. FIG. 36A shows representative cycles (1, 10, 25, 50, and 5000) for the human meniscus in each region of interest. FIG. 36B shows the data from FIG. 36A averaged across all regions. FIGS. 37A-C show the average values for the three coefficients of the power fit (A, B, C, respectively) for the human meniscus broken down by region of interest.

Figure 38A:
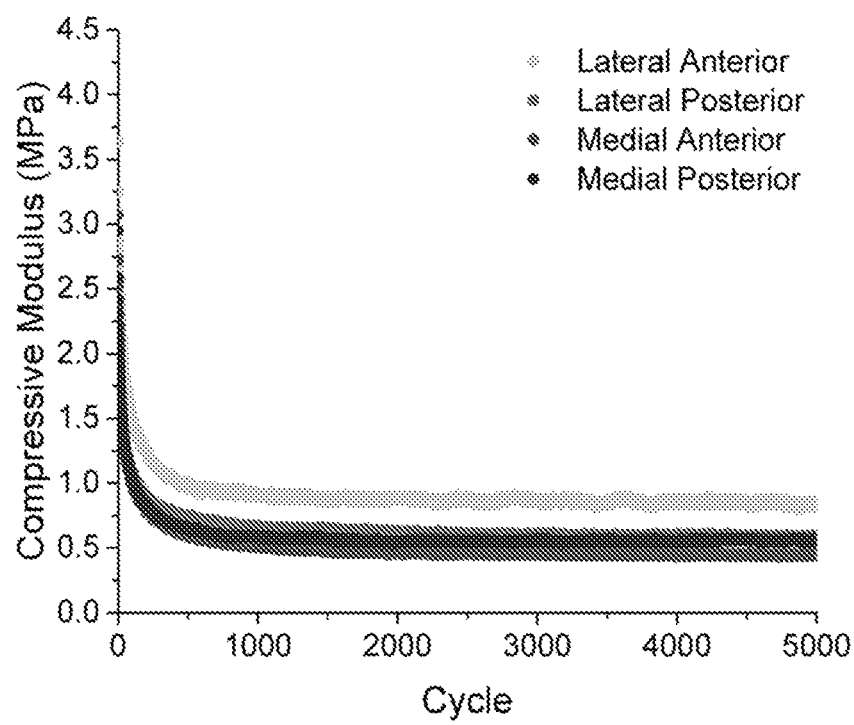
FIG. 38A. The average compressive modulus values for all 5000 cycles for the sheep (ovine) meniscus in each region of interest (lateral anterior, lateral posterior, medial anterior, and medial posterior). The first 500 cycles from the FIG. 38A are shown in FIG. 38B.
Figure 38B:
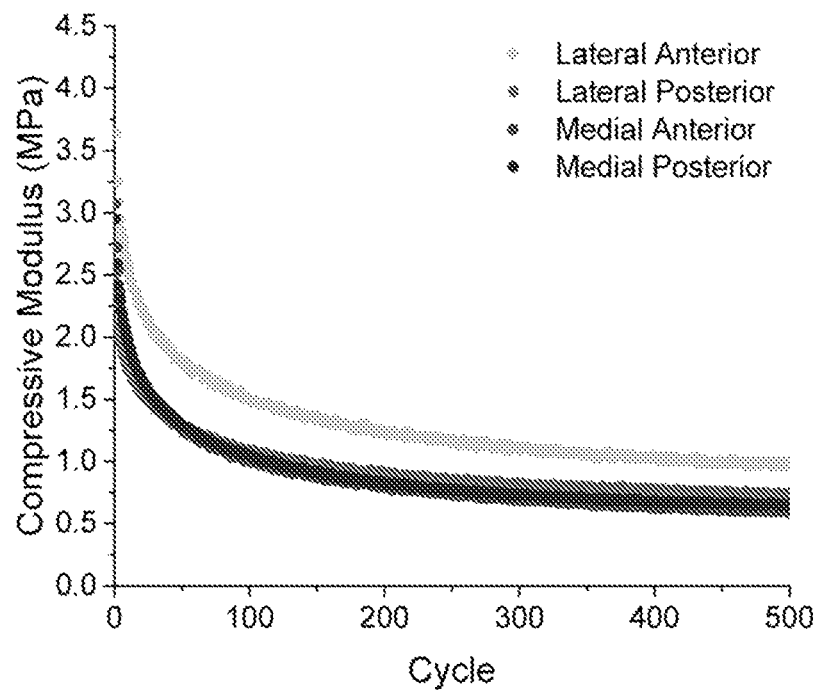
Figure 39A:
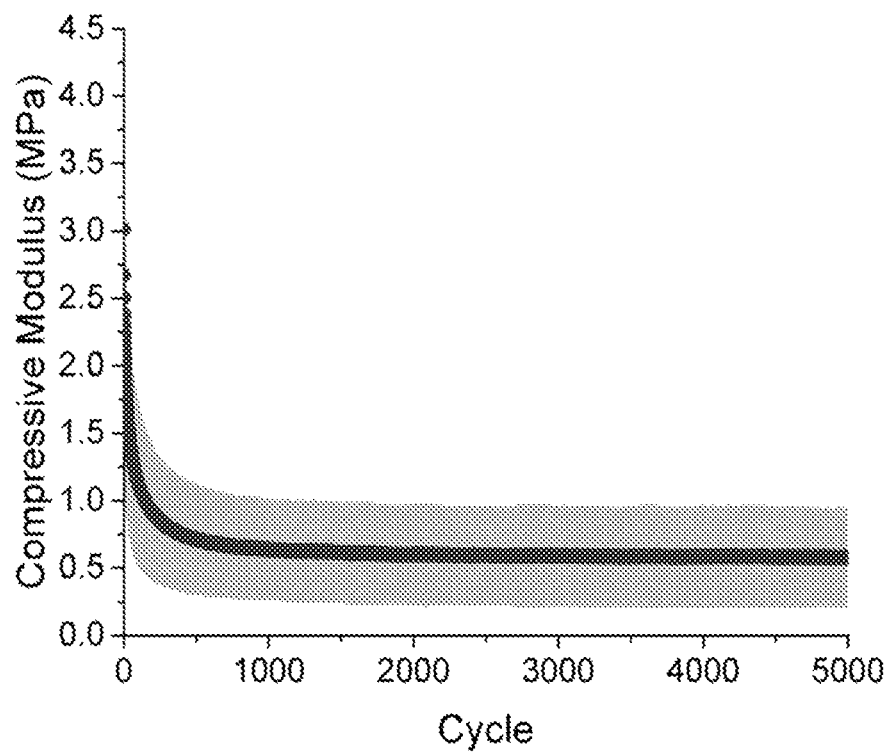
FIGS. 39A&B. The compressive modulus values for the sheep meniscus averaged for all regions of interest.
Figure 39B:
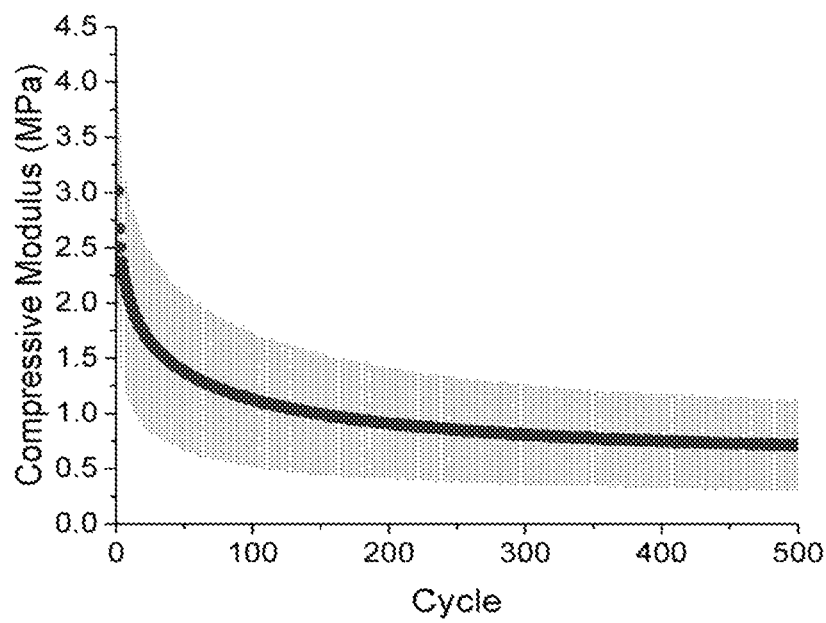
Figure 40A:
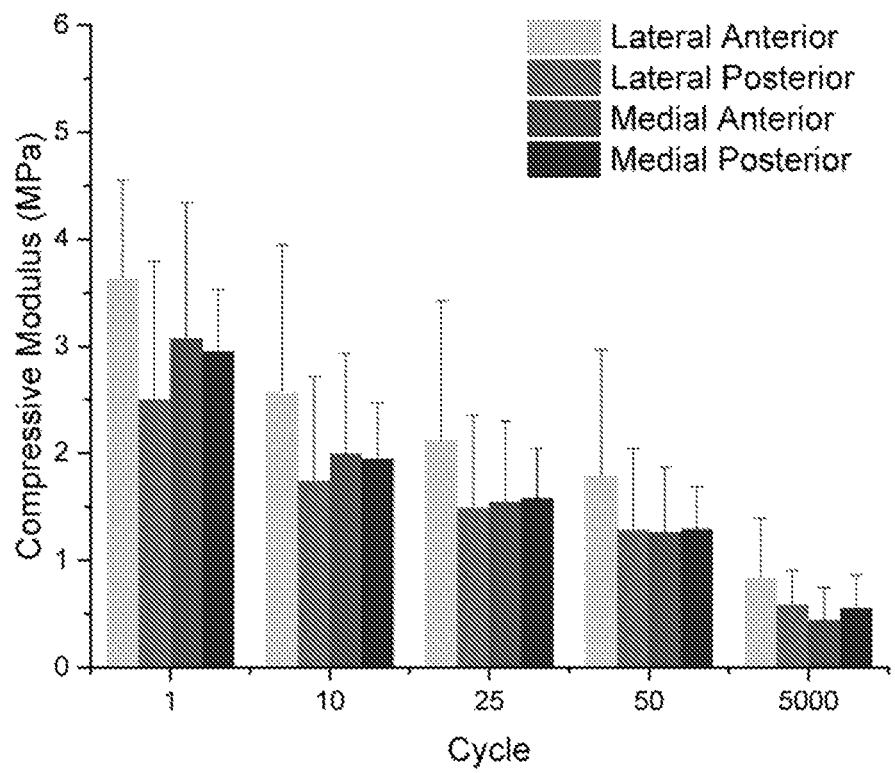
FIG. 40A. Representative cycles (1, 10, 25, 50, and 5000) for the sheep meniscus in each region of interest.
Figure 40B:
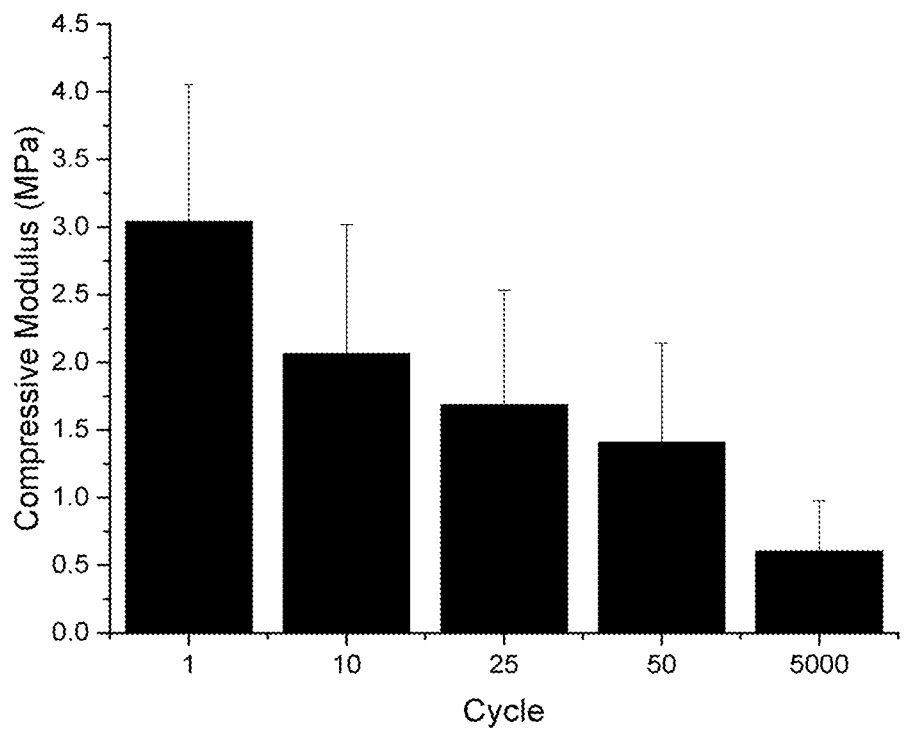
FIG. 40B shows the data from FIG. 40A averaged across all regions.
Figure 41A:
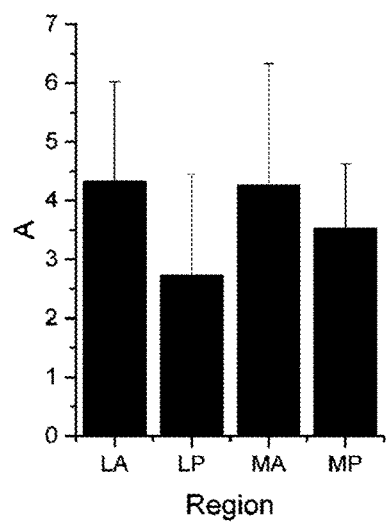
FIGS. 41A-C. The average values for the three coefficients of the power fit (A, B, C, respectively) for the human meniscus broken down by region of interest.
Figure 41B:
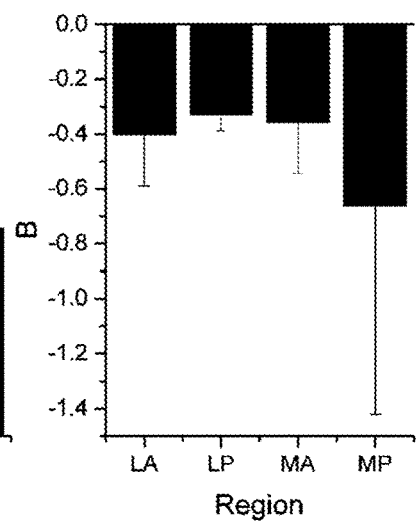
Figure 41C:
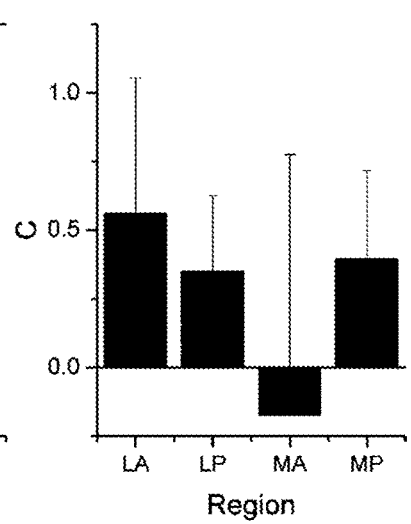

FIG. 38A shows the average compressive modulus values for all 5000 cycles for the sheep (ovine) meniscus in each region of interest (lateral anterior, lateral posterior, medial anterior, and medial posterior). The first 500 cycles from the FIG. 38A are shown in FIG. 38B. FIGS. 39A&B show the compressive modulus values for the sheep meniscus averaged for all regions of interest. FIG. 39A shows all 5000 cycles and FIG. 39B shows only the first 500 cycles of the test. FIG. 40A shows representative cycles (1, 10, 25, 50, and 5000) for the sheep meniscus in each region of interest. FIG. 40B shows the data from FIG. 40A averaged across all regions. FIGS. 41A-C show the average values for the three coefficients of the power fit (A, B, C, respectively) for the human meniscus broken down by region of interest.

Figure 42A:
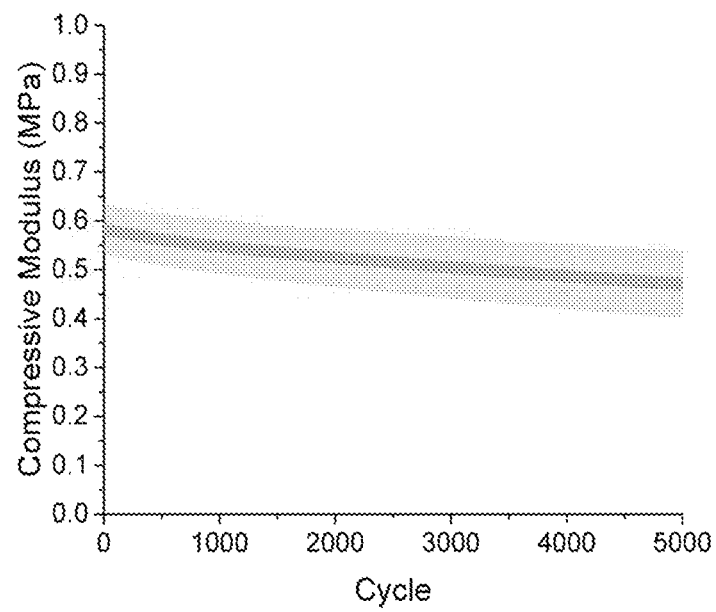
FIG. 42A. The average compressive modulus values for all 500 cycles from the block copolymer hydrogel. The first 500 cycles from FIG. 42A are shown in FIG. 42B.
Figure 42B:
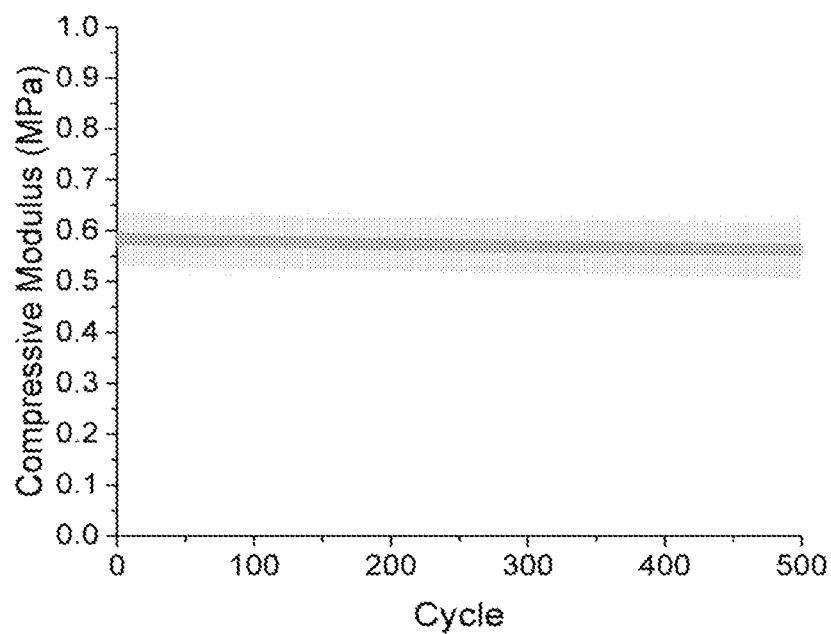
Figure 43:
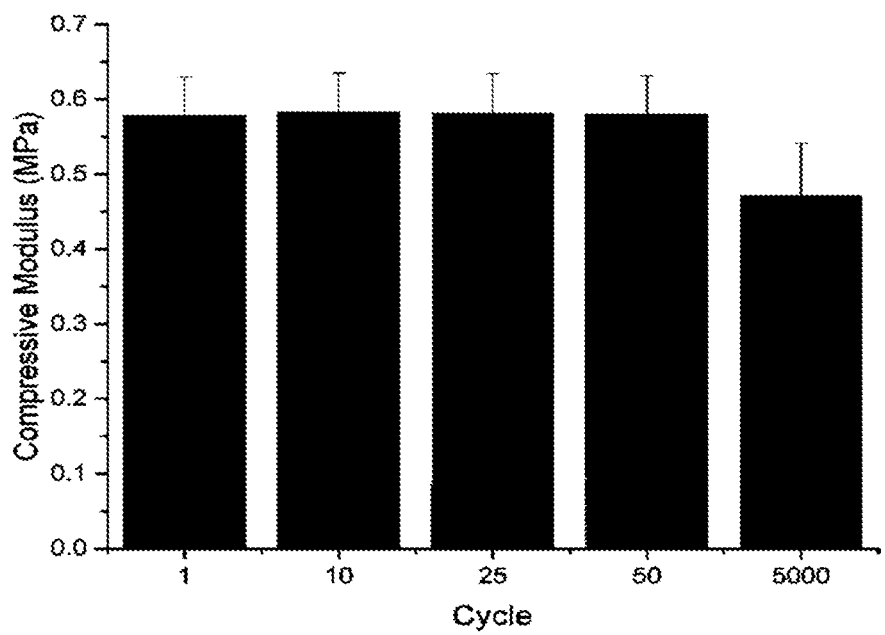
FIG. 43. Representative cycles (1, 10, 25, 50, and 5000) for the block copolymer hydrogel.
Figures 44A, 44B, 44C:
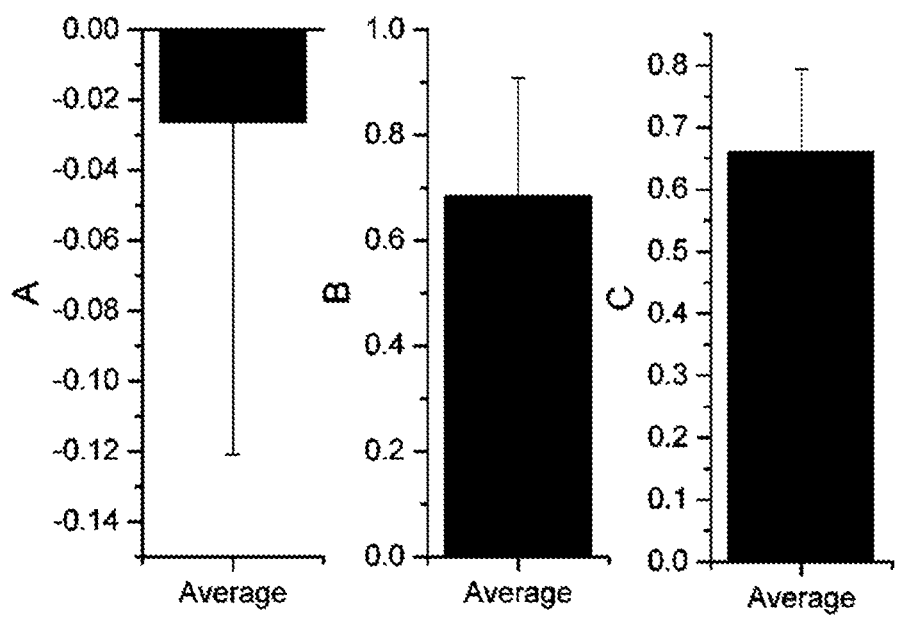
FIGS. 44A-C. The average values for the three coefficients of the power fit (A, B, C, respectively) for the block copolymer hydrogel.
Figure 45:
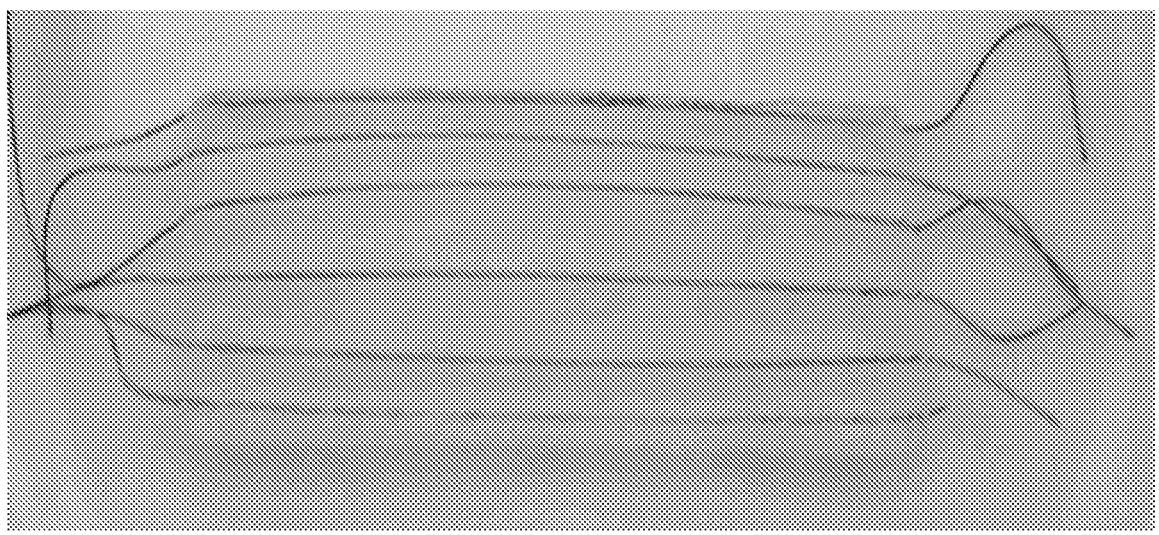
FIG. 45. Hydrogel with polyamide (Nylon™) fibers fixed after UV light exposure.

FIG. 42A shows the average compressive modulus values for all 500 cycles from the block copolymer hydrogel. The first 500 cycles from FIG. 42A are shown in FIG. 42B. FIG. 43 shows representative cycles (1, 10, 25, 50, and 5000) for the block copolymer hydrogel. FIGS. 44A-C show the average values for the three coefficients of the power fit (A, B, C, respectively) for the block copolymer hydrogel.

Example 21—Reinforcement of in Hydrogel Soft Tissue Mimetics

Many soft tissues, including knee menisci, contain biased directional fibers, which provide physiologically-relevant mechanical anisotropy. To achieve this feature in the mimetic, Nylon™ (polyamide) fibers were integrated into the hydrogel. These fibers provided a means for direct surgical attachment to the tibial plateau, and chemically bonded into the SO/SOS network to produce the one-to-two order anisotropy in the circumferential tensile modulus. Chemical attachment between the fibers and SO/SOS network were successful using photoinitiated free radical coupling (short chain polymerization). Fiber density will likely significantly influence energy transfer efficiency.

Figure 46A:
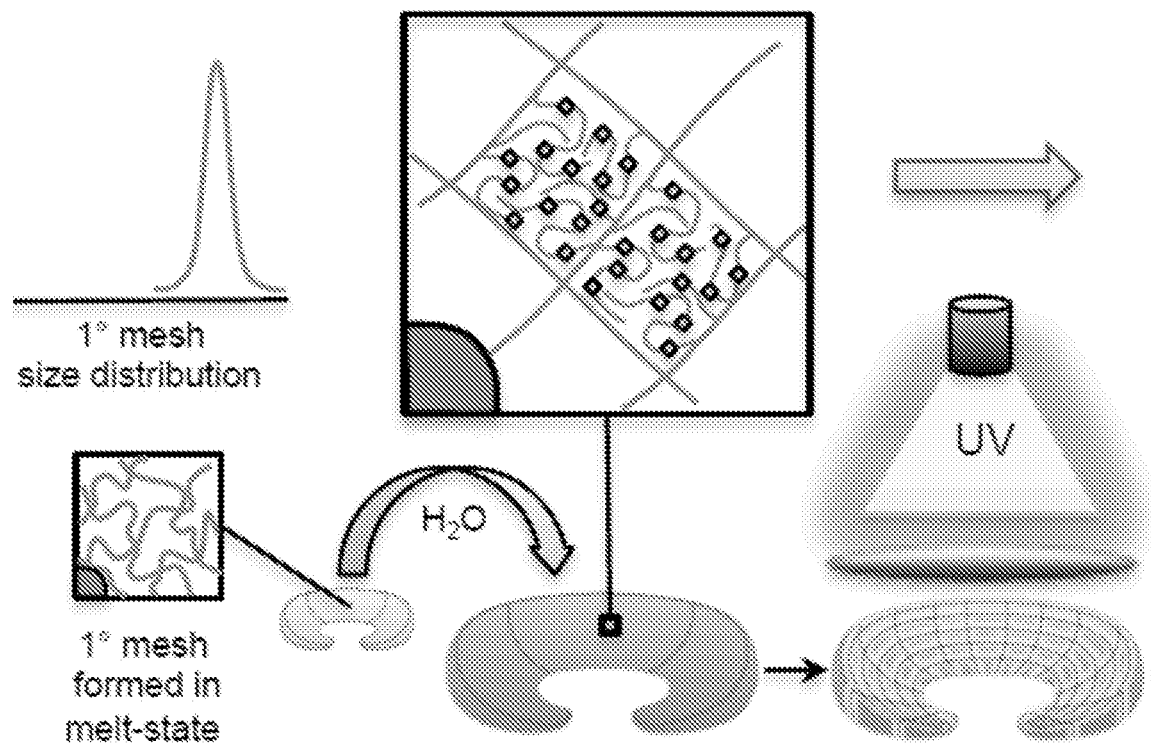
FIGS. 46A&B. Incorporation of photo-crosslinkable groups into the hydrogel matrix will permit highly localized tuning of the crosslink density using UV patterning.
Figure 46B:
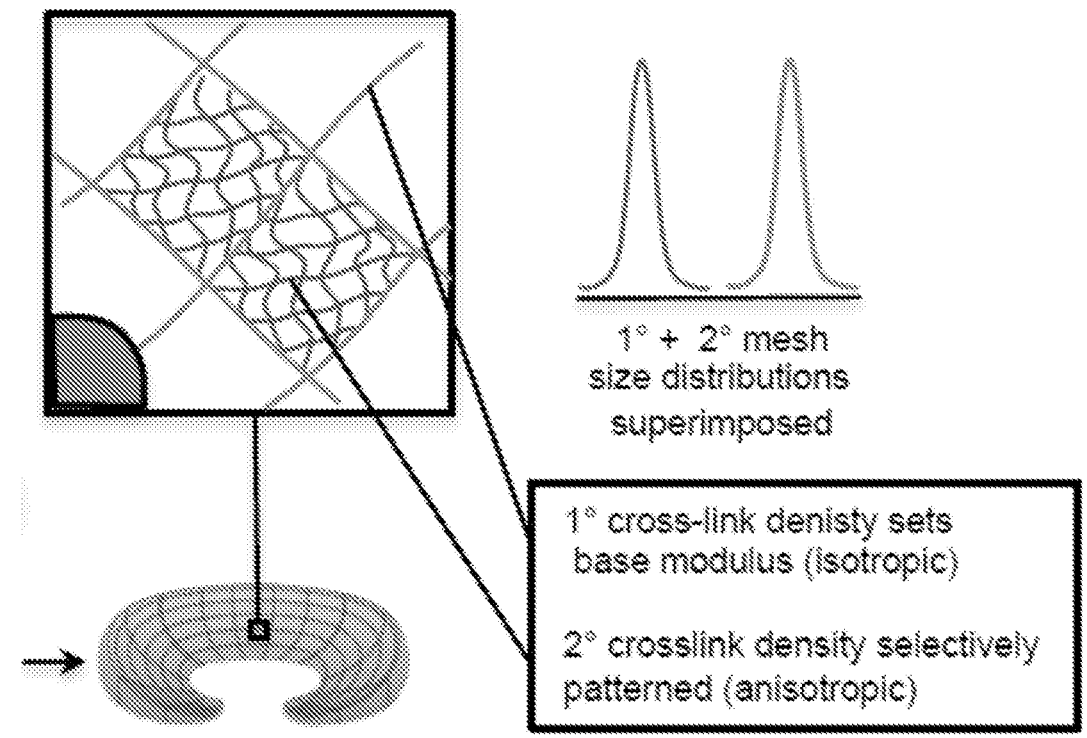
FIG. 46B shows the effects of irradiation. The primary cross-link density sets the base modulus isotropically, while the secondary density is selectively patterned anisotropically (for example, by using a photomask during irradiation). Thus, primary and secondary mesh size distributions are superimposed and layering is consistent with transverse isotropy.

Tie line patterning can be used in both the circumferential and radial directions, with the former projected onto the polyamide fiber locations (FIG. 46). Photopatterning of tie lines in the circumferential direction enhance the circumferential tensile modulus, improve energy transfer efficiency between the hydrogel and fibers, and reinforce the hydrogel against tearing. To study the effect of polyamide fibers in the hydrogel, rectangular coupons (20 mm (L)×10 mm (W)×2 mm (T)) were used with defined SOS compositions (50, 70 and 90 mol %), linear density of polyamide fibers (0.5, 1.0, and 2 fiber/mm), and linear density of tie lines (0.5, 1.0, and 2 lines/mm) (Table 1). Fibers are placed parallel to length (L) of the coupon, which proxies for the circumferential direction. Tie lines are patterned as a square mesh, oriented with mesh lines parallel ("circumferential") and perpendicular ("radial") to the fibers. All polyamide fibers are reinforced by a coincident tie line, where the tie line density equals or exceeds the polyamide fiber density.

SO/SOS networks are produced using melt-state self-assembly at 120° C. with a 10-min anneal). Fibers are size 5-0 (0.1 mm) non-adsorbable polyamide sutures (Dermalon™), surface-modified with acrylate groups. Fibers are threaded into the test coupons using basic suturing needles (5-0 gauge). Patterned tie line widths are fixed at 0.2 mm and are produced from acrylate-modified hyaluronic acid (70-100 kDa, Lifecore™). The hyaluronic acid may also be fluorescently tagged to verify patterning. Irgacure™ 5929 or lithium acylphosphinate are known for their compatibility with biological systems and may be used as water-soluble free radical initiators.

Mechanical testing may be performed in a bath of phosphate-buffered saline (PBS) bath to keep the hydrogels hydrated. Instantaneous and equilibrium compressive properties are obtained using indentation relaxation and unconfined compression tests (Bionic Model 370.02 MTS Corp., Eden Prairie, Minn.). Preliminary tests and subsequent power analysis suggest a sample size of n=7 is sufficient for detecting significant differences. Unconfined compression assesses modulus changes over extended cyclic loading. The influence of cycle frequency on modulus decay rate and magnitude over 1000 cycles is evaluated using frequencies of 0.1, 0.5, 1, and 5 Hz. Minimum time for full recovery is also established for each sample. The long-term impact of cyclic loading is assessed over 280 successive 500-cycle runs, each using 12% strain and loading frequency of 1 Hz. Each composite tested rests between runs at minimum time for full recovery with an overnight rest every 2500 total cycles. This experimental design mimics 8 weeks of daily periodic loading consistent with that anticipated in the ovine model. Tensile elastic modulus is determined from pull-to-failure tests (n=5) at a strain rate of 12%/sec, corresponding to physiological loading rates of the meniscus in the circumferential direction.

Samples are speckle-coated, filmed, and analyzed using a MATLAB (Mathworks, Natick, Mass.) digital image correlation code (E.M.C. Jones, University of Illinois) to determine Poisson's ratio. Trouser tear tests with standardized JIS-K6252 ½ sizes assess the gel's fracture energy (velocity=0.005 mm/s). Explants of the composites are tested in simple shear using a linear variable differential transformer

TABLE 5

Polyamide Fiber Experimental Design

Biphasic Composite Test Sample #

| Variable | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| SOS mol % | | | 50 | | | | | | 70 | | | | | | 90 | | | |
| Fiber density (#/mm) | | 0.5 | | 1.0 | | 2.0 | | 0.5 | | 1.0 | | 2.0 | | 0.5 | | 1.0 | | 2.0 |
| HA IPN density (#/mm) | 0.5 | 1.0 | 2.0 | 1.0 | 2.0 | 2.0 | 0.5 | 1.0 | 2.0 | 1.0 | 2.0 | 2.0 | 0.5 | 1.0 | 2.0 | 1.0 | 2.0 | 2.0 |

The top four candidates are selected for translation into equivalent 3D implants for further mechanical evaluation under anatomical loading. All samples are produced using a single batch of sphere-forming SO diblock (Example 3, 90 kDa total, 90 w % PEG), and SOS triblock copolymer (Example 4, 180 kDa total, 90 w % PEG). Acrylate functionality are added to the SO diblock copolymers. Initial to track displacement between shear plates. Sample sizes for material properties are all based on preliminary data and a statistical power of 90%. All tests will be performed both parallel and perpendicular to fiber direction. Statistical comparison between composites with differing SOS compositions, polyamide fiber density and tie line densities will be assessed using a repeated measure analysis of variance (ANOVA). Sample t-tests for comparing two means will be used to evaluate differences between literature values for the native meniscus and the various composite designs. Statistical significance will be assessed at $p<0.05$.

Material properties including compressive, tensile, and shear moduli, Poisson's ratio, fracture energy, and quantified levels of fatigue and long-term durability for the full range of composite designs are expected to show differences based on SOS composition, polyamide fiber, and the tie lines densities. The impact of increased circumferential tensile modulus and stress distribution efficiency produced by polyamide fiber and tie line densities on long-term fatigue and durability also affects experimental design. As a whole, these results could provide a library of material properties suggesting strategies for further improvements. The top four candidates are selected for translation into equivalent 3D implants for further mechanical evaluation under anatomical loading (see Example 24 below).

Block copolymer molecular weights can be increased for greater modulus at lower SOS compositions. Fiber diameter can be increased (e.g. 3-0 or 0) to enhance surface contact with the matrix, or decreased (e.g 6-0) to allow increased fiber densities. Tie line widths or patterns can be increased or decreased via photomask design. Molecular weights of the hyaluronic acid prior to crosslinking into the tie line can be altered to enhance network connectivity, and acrylate functional group surface concentrations can be controlled using reaction conditions.

The SO copolymer possesses terminal hydroxyl groups to which acrylate functionality can be added, creating an attachment site for integrated polyamide fibers. As mentioned above, the surface of the polyamide fibers can be modified with acrylate functionality, first by the partial oxidation to generate surface hydroxyls followed by analogous acrylate addition. This fiber modification has limited impact on the mechanical integrity of the fiber structure. Both the modified fibers and hydrogels can be molded into composite structures without chemical bonding. Once equilibrium swelling has been established, photoinduced free-radical coupling (short-chain polymerization) of the acrylate groups between fiber and hydrogel establish chemical connectivity. Varying the reaction conditions allows control over the concentration of acrylate functionality added to the block copolymer and polyamide suture surface, so one can tailor the bonding density and energy transfer efficiency between the hydrogel matrix and the polyamide fiber reinforcements. Bonding density can be controlled by adjusting the number of reactive sites between the hydrogel and the fiber surface. Adjusting the density of reactive groups provides considerable flexibility to chemically control the bonding density and mechanical strength. Three suture sizes are used (size 0, 3-0, 5-0). A high bonding density (contact area of 75%) and a low bonding density (25% contact area) are investigated. Samples are prepared with the primary fiber orientation in the longitudinal direction. Fiber density are controlled using a fiber-to-gel ratio of 1:100 (low density) and a ratio of 1:10 (high density). Controlling for these three variables will result in a total of 12 different fiber-reinforced hydrogels that will be compared.

Of note, the native meniscus has an instantaneous modulus of 0.5-3 MPa, an equilibrium compressive modulus 0.05-0.3 MPa, and a tensile modulus from about 43 MPa to about 140 MPa. If tensile elastic modulus values are achieved with the polyamide fibers, silk fibers may be used. The hydrogel could also allow for glycosaminoglycans, hyaluronic acid, chitosan, and other polysaccharides to be incorporated to tailor the mechanics, including photopatterning acrylate-modified glycosaminoglycan into these hydrogel systems, which may be beneficial in tailoring time dependent properties to better mimic the native meniscus.

Example 22—Biocompatiblity of Hydrogel Soft Tissue Mimetics

Polyethylene oxide (PEO) is biocompatible and the polyamide sutures being added are non-absorbable surgical sutures, which are also biocompatible. As described herein, PEO forms a dense corona surrounding the polystyrene, resulting in the PEO being the primary surface polymer to interact with the environment.

The fiber-reinforced hydrogels are subcutaneously implanted on the backs of female Sprague-Dawley rats. Rats are anesthetized with diethyl ether and backs are shaved and scrubbed with betadine solution. A 2-cm incision is made on the midline 3 cm from the tail. Blunt scissor dissection creates a bilateral implant site. The gels are inserted and the incision closed using 5-0 poly dioxanone monofilament synthetic absorbable suture. Animals are allowed to recover, and later sacrificed four (n=10) and fourteen (n=10) days post-surgery. Time points include two groups (n=5): Group one has the hydrogels implanted and Group 2 undergoes a sham surgery. Euthanasia is carried out using $CO_2$ inhalation or sub-cutaneous ketamine sedation followed by a lethal dose of intravenous sodium phenobarbital. Constructs are harvested post-mortem and stored at −80° C. Control animals are used and the surgical procedures are performed without implantation to assess inflammatory effects due to procedure alone.

The implanted fiber-reinforced hydrogels are removed and assessed for surface defects, leukocyte concentration, extracellular acid, and alkaline phosphatase activity. Gels are initially inspected with India ink to establish a visual baseline and assess gross damage. The inflammatory exudate are aspirated from the implantation sight with a 27.5-gauge needle and analyzed for leukocyte concentration using a hemocytometer. Cell counts are taken and slides stained with Wright's stain (Sigma Diagnostics, St. Louis, Mo.) are used to count polymorphonuclear leukocytes, monocytes, and lymphocytes. A p-nitrophenylphosphate (Diagnostic Kit #104; Sigma Diagnostics, St. Louis, Mo.) is also performed to determine the extracellular acid and alkaline phosphatase activity. Wright's stain is used to assess the size and density of adherent cells as a function of cell number/sample area using an Olympus BH2 Microscope (Center Valley, Pa.) and MicroPublisher 5.0 RTV camera (Qlmaging, Surrey, BC, Canada).

Inflammatory exudate is compared to controls euthanized at the same time points and between the 4- and 14-day time points using a two-way repeated analysis of variance (ANOVA). A total of 20 rats are used for this aim, allowing for n=5 in each group/time point. Adherent cell size and density are also collected and compared between time points. Surface defects will be characterized by size and number using four blind graders and Wilcoxon signed rank test. Implanted hydrogels are compared to non-implanted hydrogels as well as between implanted hydrogels at the two time points. Comparisons assess statistical significance at $p<0.05$.

The fiber-reinforced hydrogel should be biocompatible and inflammatory response should be similar to that in the control. Specifically, leukocyte concentration and alkaline phosphatase activity are not increased between the control and implanted animals. Additionally, no adherent cells nor the surface of the gels are damaged after time points of 4 and 14 days of subcutaneous implantation. The results provide information regarding initial inflammatory and cell responses.

Example 23—Incorporating Hyaluronic Acid into SO-SOS Block Copolymers

Hyaluronic acid (HA) was incorporated in the block copolymer hydrogels and crosslinked via a modified Steglich reaction using the water-soluble carbodiimide 1-ethyl-3-(3-dimethylaminopropyl) carbodiimide (EDC). To start, a dry SO/SOS (32 mol % SOS, "SOS32") polymer was swollen in a 1.5 wt. % solution of HA (700 kDa MW) for 48 hours. The resultant HA-hydrogel was removed from HA solution and dried under vacuum for 24 hours. The dry HA-SOS polymer was re-swollen for 72 hours in solution to 1.5× the dry mass of the sample. The solution contained 0.01 M HCl and 4:1 molar equivalents of EDC to infused HA repeat units. The hydrogel was rinsed in a periodically-replaced solution of DI water for 48 hours.

This concentration of 1-ethyl-3-(3-dimethylaminopropyl) carbodiimide (EDC) created an interpenetrating network stable inside the hydrogel for at least 1 week. Higher concentrations produced a more highly crosslinked hyaluronic acid (HA) network but may produce a more brittle HA network. Forming the HA network at sub-equilibrium swollen dimensions has the potential to permanently reduce the extent of swelling possible in the SOS network. This has the added advantage of increasing the osmotic pressure (and thus modulus) in the system, while mechanically activating the HA network toward stress distribution. The resultant HA/SOS hydrogels were characterized, and subjected to unconfined compression testing, uniaxial tensile testing, and cytotoxicity testing via lactate dehydrogenase (LDH) assay under the same conditions as the neat SO/SOS hydrogel. These tests verified the effect of the secondary HA network on the mechanical properties and the general cytotoxicity of the hydrogel.

The difference in mass between the dry SO/SOS polymer and the processed hyaluronic acid (HA) polymer quantified the HA inside of the SO/SOS polymer. This value was compared to thermogravimetric analysis (TGA) to confirm the amount of HA present inside of the hydrogel. Specifically, the TGA showed that the mass percent of HA in the HA-infused SOS32 was between about 9.6 and 10.8 mass %. TGA mass % of HA values were calculated by taking the difference between the SOS32 curve and the HA-infused SOS32 curve at 350° C. and adding that to the difference between those same two curves at 450° C.

Figure 47:
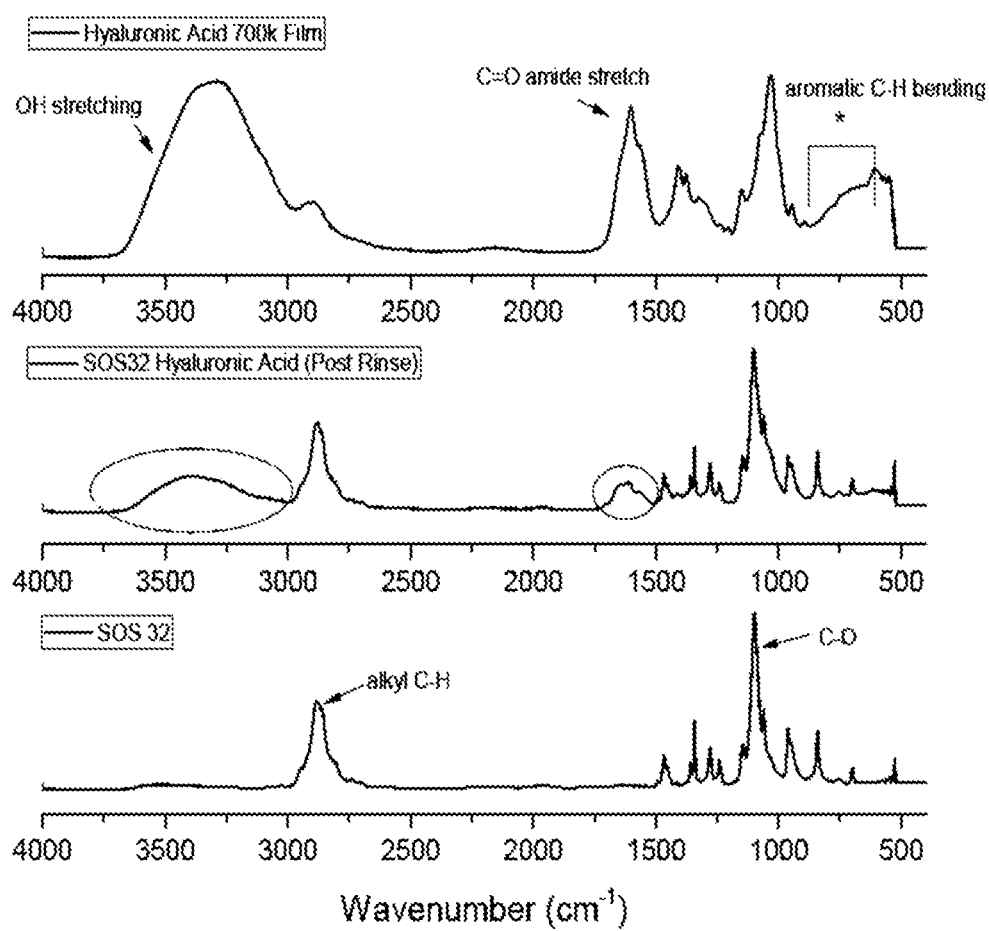
FIG. 47. Attenuated total reflectance Fourier transform infrared (ATR-FTIR) spectra of hyaluronic acid, neat SOS32, and HA-infused SOS32.
Figure 48A:
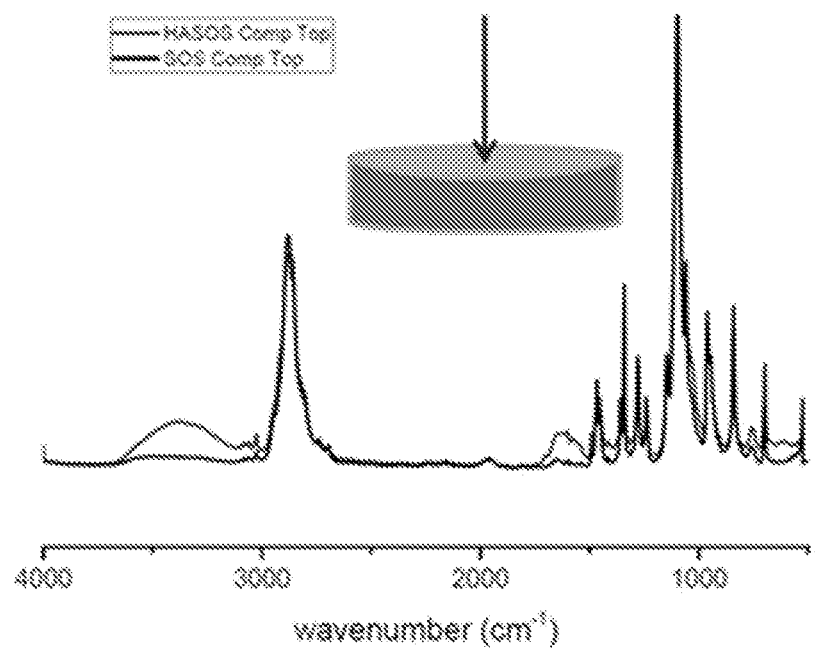
FIG. 48A. ATR-FTIR spectrum of the outer surface of neat and HA-infused SOS32 sample.
Figure 48B:
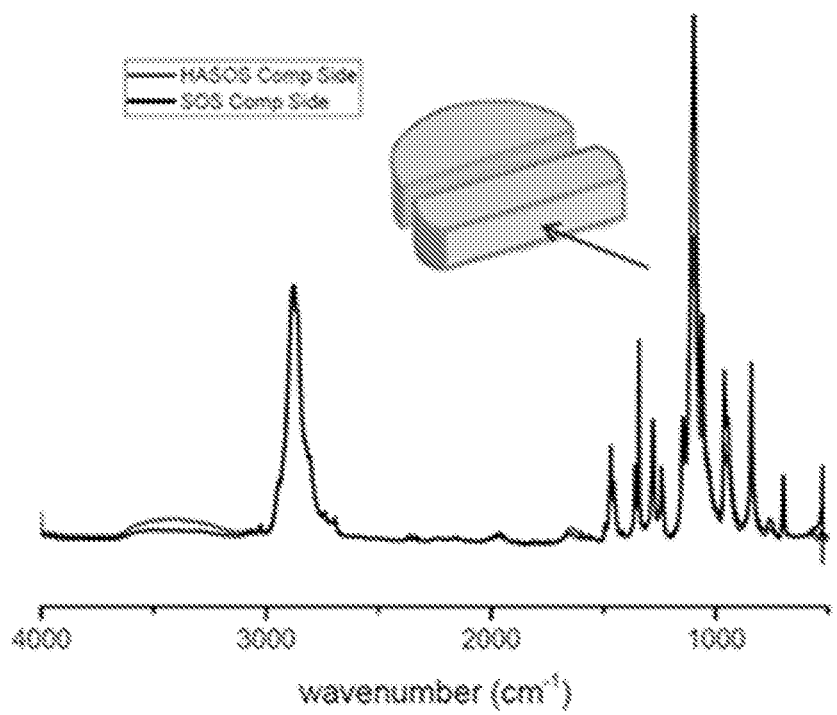
FIG. 48B shows ATR-FTIR spectrum of the center of the these samples.

The dry sample was bisected to expose the center the dry hydrogel to attenuated total reflectance Fourier transform infrared (ATR-FTIR) spectroscopy. The spectra of the outer surface and the center were compared to qualitatively analysis of the hyaluronic acid (HA) in the hydrogel. FIG. 47 shows ATR-FTIR spectra of HA, neat SOS32, and HA-infused SOS32. ATR-FTIR regions belonging to the HA corresponded to amide and hydroxyl stretches not present in the neat SOS32. FIGS. 48A&B show ATR-FTIR spectra of HA-infused SOS32 and neat SOS32, revealing higher concentrations of hyaluronic acid at the surface than at the center of the hydrogel. The ratio of hydroxyl and amide stretches to alkane stretches is higher on the surface than at the center of the materials.

Figure 49:
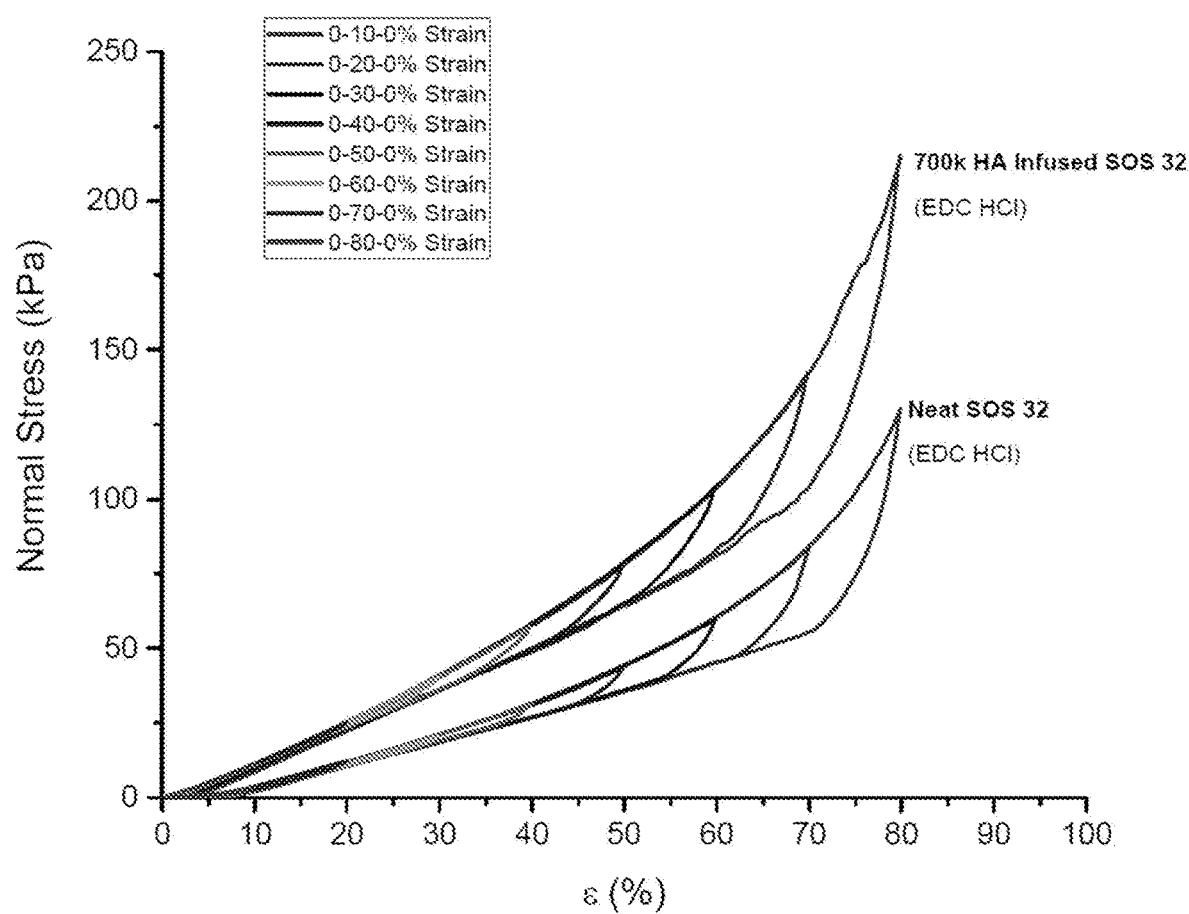
FIG. 49. The progressive unconfined compression testing of hyaluronic acid infused SOS32 and SOS32 hydrogels.

FIG. 49 shows the progressive unconfined compression testing of SOS32 hydrogel infused with crosslinked hyaluronic acid (HA) and neat SOS32 hydrogels. HA-infused SOS32 hydrogel produced a higher (~1.75×) compressive modulus than the neat SOS32. The increased modulus did not diminish the hydrogel's resistance to low cycle material fatigue at various successive strains up to 80% strain.

Figure 50:
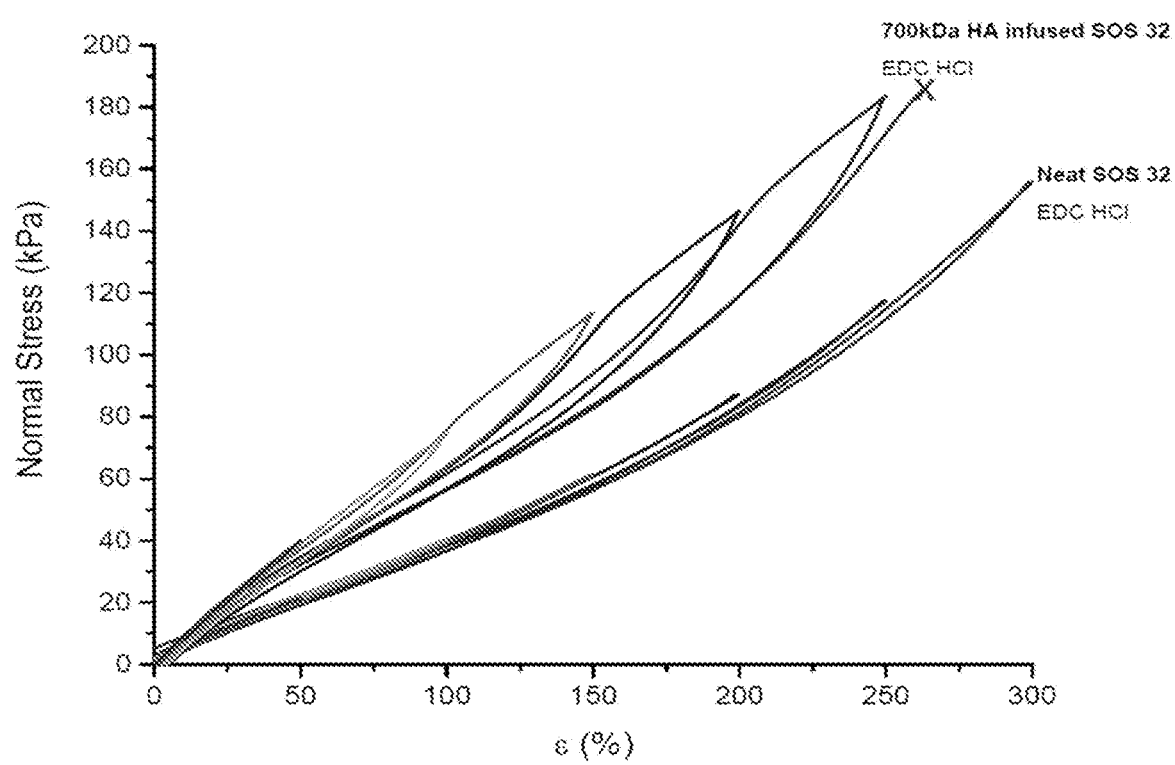
FIG. 50 shows the progressive tensile testing of hyaluronic acid infused SOS32 and SOS32 neat hydrogels at a 2% strain rate.

FIG. 50 shows the progressive tensile testing of SOS32 hydrogel infused with crosslinked hyaluronic acid (HA) and neat SOS32 hydrogels at a 2% strain rate. The HA-infused SOS32 sample demonstrated a higher modulus (~1.4×) than the neat sample. The increased modulus, however, resisted fatigue at low strains (up to 50%) but not at higher strains (>100%) upon successive loading cycles.

Figure 51A:
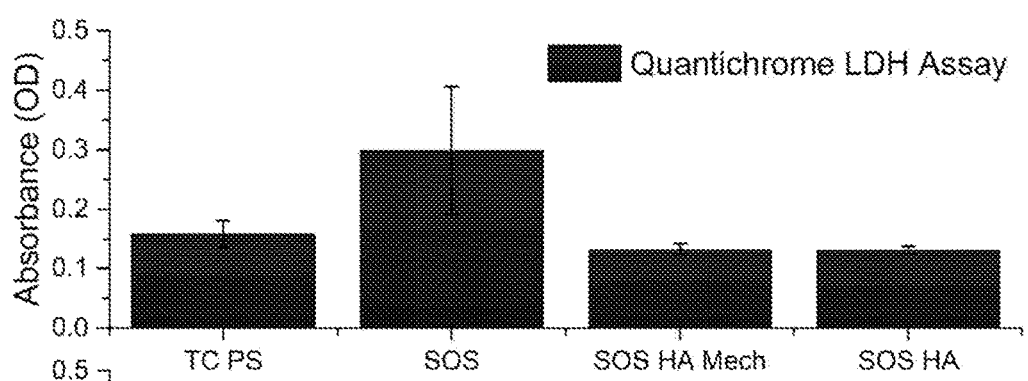
FIGS. 51A&B. The Cayman (FIG. 51A) and QuantiChrom™ lactate dehydrogenase (LDH) (FIG. 51B) assays of tissue culture polystyrene (TC PS), SOS32 neat hydrogel (SOS), SOS hyaluronic acid that underwent mechanical loading (10 runs of 10 12% strain at 1 Hz followed by one cycle of 50% strain (SOS HA Mech), and HA-infused SOS32 (SOS HA) (n=5 for each group).
Figure 51B:
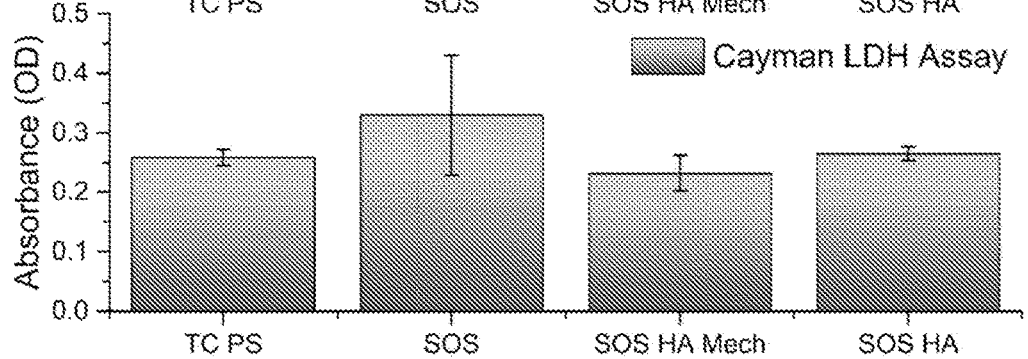

FIGS. 51A&B shows the Cayman (FIG. 51A) and QuantiChrom™ lactate dehydrogenase (LDH) (FIG. 51B) assays of tissue culture polystyrene (TC PS), neat SOS32 hydrogel (SOS), SOS infused with crosslinked hyaluronic acid (HA) that underwent mechanical loading (10 runs of 10 cycles at 12% strain at 1 Hz followed by one cycle of 50% strain (SOS HA Mech), and SOS32 infused with crosslinked HA (SOS HA) (n=5 for each group). The lower the absorbance value on the LDH assay, the lower the general cytotoxicity of that material. The hyaluronic acid infusion into the SOS32 reduced the overall cytotoxicity of the SOS32, which was persistent after mechanical loading.

SOS32 hydrogels infused with crosslinked hyaluronic acid (HA) resided in a DI water bath for a week after the crosslinking of HA and mechanical loading. During this week, unbound HA was rinsed off and the DI water was replaced each day. The HA had a MW of 700 kDa. A 40-kDa HA does not crosslink as efficiently as the 700 kDa. MWs above 100 kDa provided sufficient chain entanglement to crosslink and stay inside the hydrogel after rinsing. HA swelling solutions of 700 kDa has a concentration of 1.5 wt %. It is difficult to obtain higher concentration solutions because of the solubility limit of 700 kDa HA.

Swelling the hydrogels under refrigeration increased the pore size of the hydrogels and accelerated diffusion of hyaluronic acid (HA) into the hydrogel. With a 100 kDa to 200 kDa MW HA, a much higher solubility limit was achieved and may allow for a higher concentration and deeper penetration of HA into the hydrogel This incorporation and crosslinking technique can be used with any SOS-containing hydrogels. Crosslinking is optional, not required.

Example 24—Photopatterning Hyaluronic Acid onto SO Diblock Copolymers

Surface photopatterning of hyaluronic acid on the polymeric materials was explored using a SO diblock copolymer (e.g., Example 3). Two dry SO disks (about 0.1 g) were placed into a 1 mL solution of 0.1 g sodium hyaluronate/mL water and were swollen for 24 hours. Another disk was placed into 1 mL water.

The polymeric materials were designated to 3 groups: (A) No HA (B) HA no XL (C) HA XL. Polymers were subjected to the same reaction conditions, except that group C was subjected to crosslinking through butanediol diglycidyl ether (BDDE). The polymeric material for group C was placed into a solution containing BDDE which is a crosslinker that acts at the primary alcohol on the hyaluronic acid. All polymeric materials were then subjected to a water bath at 40° C. for 8 hours.

Figure 52:
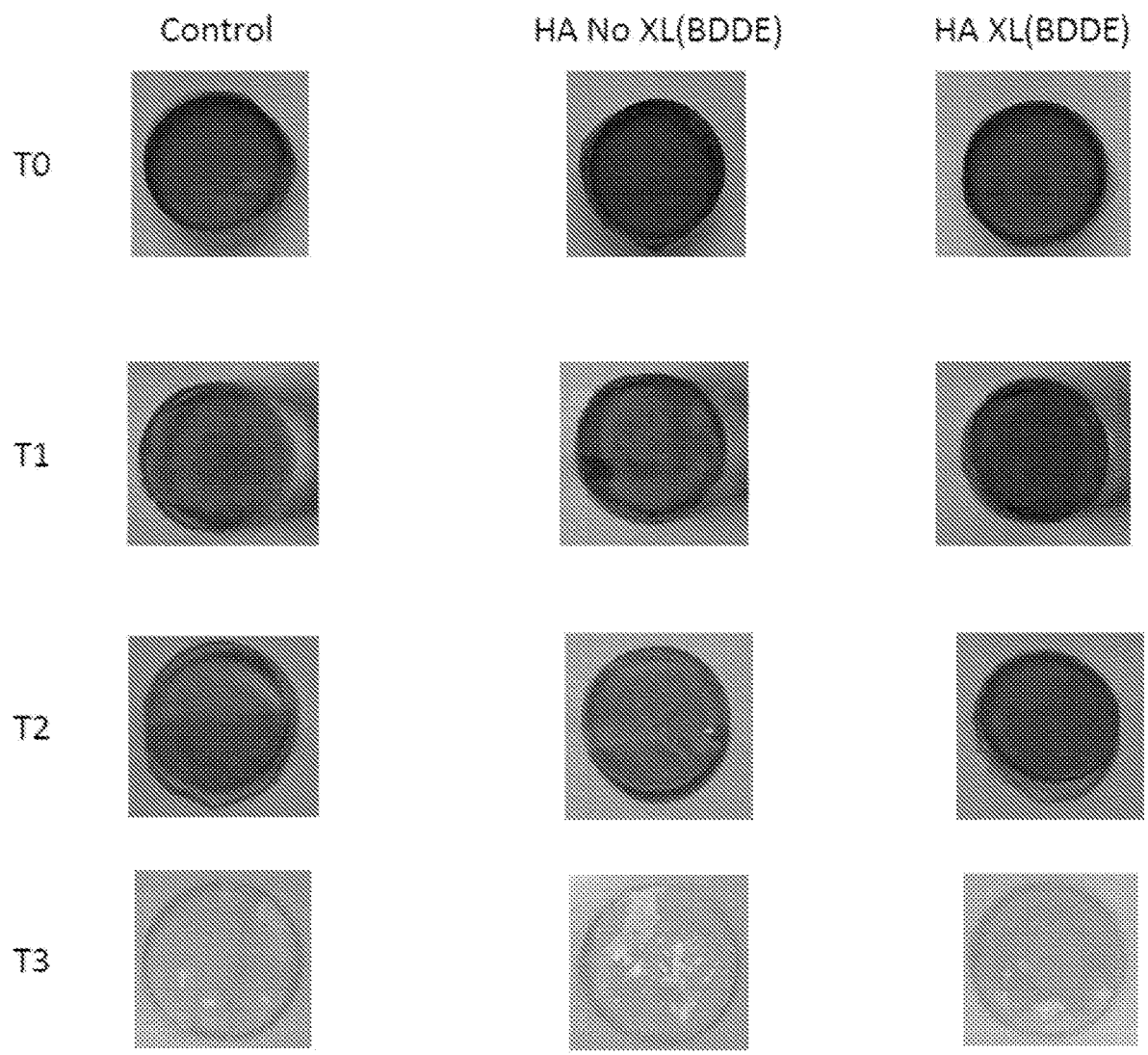
FIG. 52. A grid of photographs showing toluidine Blue O (TBO)-stained polymeric material samples.
Figure 53:
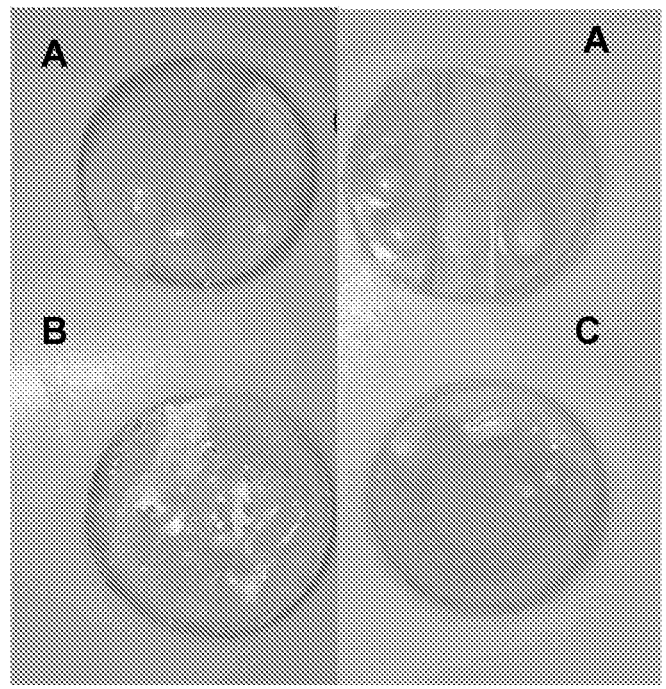
FIG. 53. Comparison photographs of TBO-stained polymeric material samples.

Polymeric materials were then placed into a solution containing Toluidine Blue O (TBO) stain and soaked for 10 minutes. The polymeric materials were soaked in water for 48 hours, until the control showed no color (FIG. 52). The polymeric materials revealed no penetration of HA beyond the surface (FIG. 53). The polymeric materials having HA crosslinked by BDDE showed the darkest color and thus the highest hyaluronan concentration at the surface.

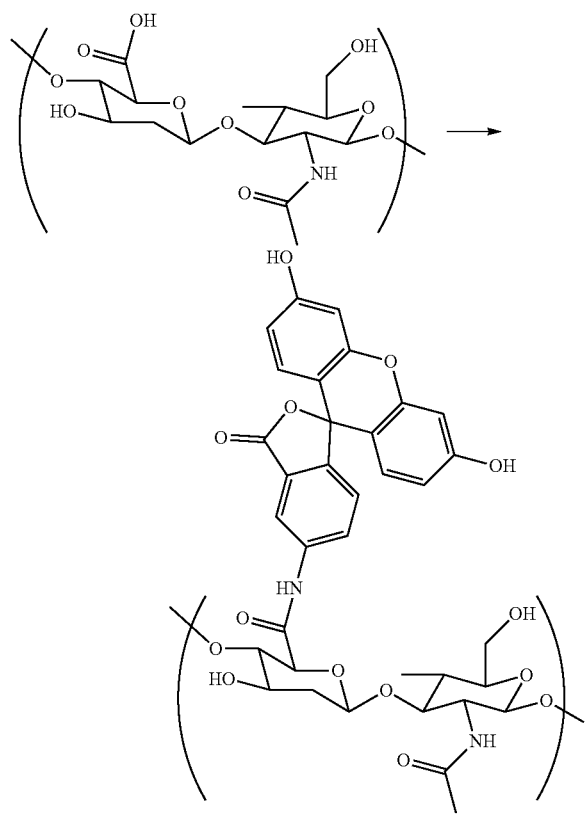

HA was fluorescently labeled with 5-aminofluorescein as depicted in the scheme above. Briefly, 48 mg of HA was dissolved in 12 mL hydrochloric acid/pyridine solution (75/25 wt. %) with a pH 4.75, then 70.5 mg of 5-aminofluorescein and 0.965 g of EDC was added. The resulting mixture reacted overnight. Following reaction, the solution was dialyzed against 3.5 L water in dialysis tubing, changing the surrounding water every 12 hours for 48 hours. Once the dialysis was complete and no unbound 5-aminofluorescein was visibly present, the solution was precipitated in chilled ethanol with 1.25 wt. % sodium acetate. The precipitate was then centrifuged and dissolved in water and the process was repeated. The pellet recovered from the second centrifugation was dissolved in water and the water was then removed through lyophilization.

Figure 54:
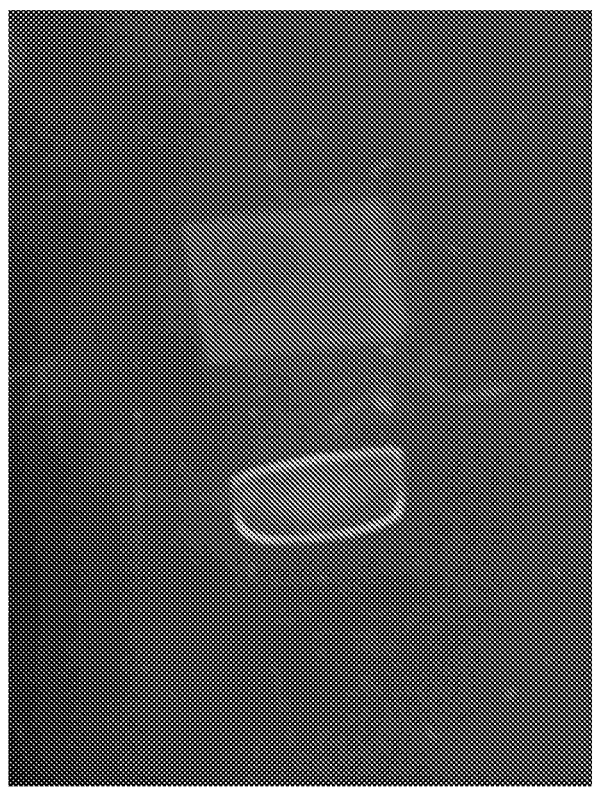
FIG. 54. A photograph of a control polymer host produced by swelling a dry polystyrene block polyethylene oxide (SO) diblock polymer host in an hyaluronic acid (HA) solution and examining it under 365-nm filtered ultraviolet (UV) light.

The recovered hyaluronic acid tagged with 5-aminofluorescein was then dissolved in water at a concentration 5 mg per 6 mL water. A dry SO disk was then swollen in the solution for 24 hours, removed and dabbed to remove any excess solution. A control gel was produced by swelling a dry polymer host disk in an untagged hyaluronic acid solution. The polymer hosts were then examined under a handheld lamp with a 365-nm filter (FIG. 54). The polymer host swollen in the fluorescently tagged HA solution fluoresced, indicating a presence of HA in the gel. The gel swollen in the untagged HA showed no fluorescent behavior.

Polymeric materials were photopatterned the Colorado State University logo by printing multiple layers of ink over the transparency in the shape of the logo after adding an attenuator to prevent (or substantially reduce) photobleaching. The hydrogels with fluorescently-tagged HA were covered with the photomask and irradiated with 365-nm filtered 22 W/cm$^2$ ultraviolet light for 8 minutes, effecting new covalent bonds to hyaluronic acid from solution. The intensity and exposure time of the light described caused photobleaching of the fluorescein tag of the HA. Following exposure to UV light, the sample was placed into water and the non-crosslinked HA was allowed to leave the sample. After 60 hours of washing, the pattern was still present on the gel, indicating that the dark portion of the mask let in light at the correct intensity to crosslink but not to photobleach (FIGS. 55A&B). Due to the attenuator, no photobleaching was observed after exposure (FIG. 56B). Following exposure, the sample was placed in water and rinsed for 2 hours (FIG. 56C) and again for 20 hours (FIG. 56D).

Example 25—3D Printing and Molding Hydrogel Soft Tissue Mimetics

Figure 57A:
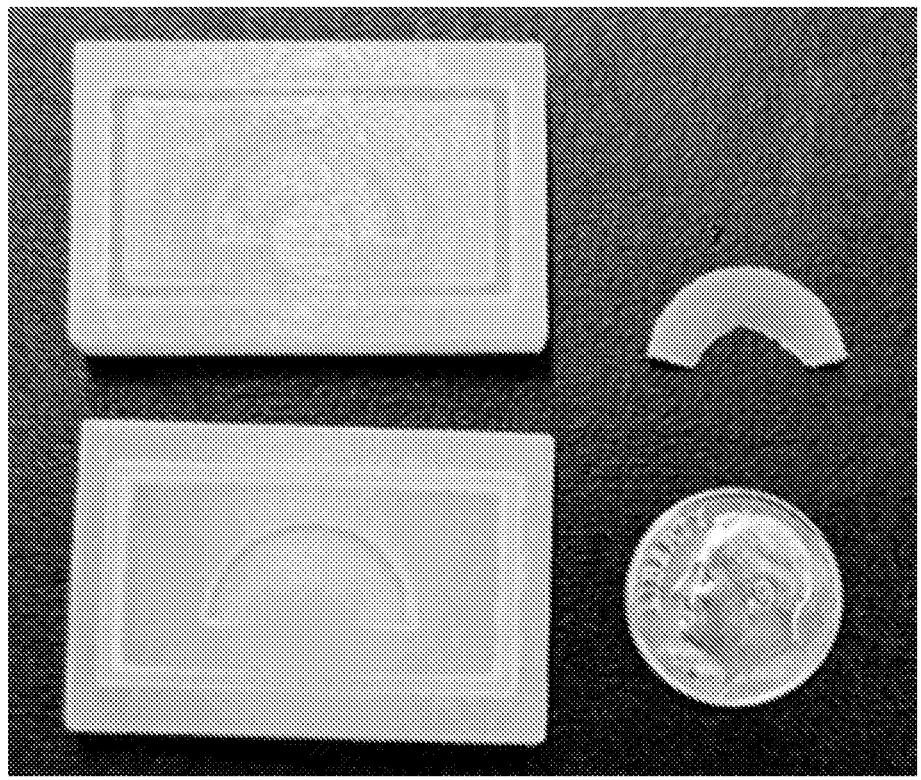
FIGS. 57A-D depict an initial proof-of-concept compression molding experiment validating the ability of the hydrogel polymer to be molded into a crescent shape and swollen to match the size of actual meniscal tissue.
Figures 57B, 57C, 57D:
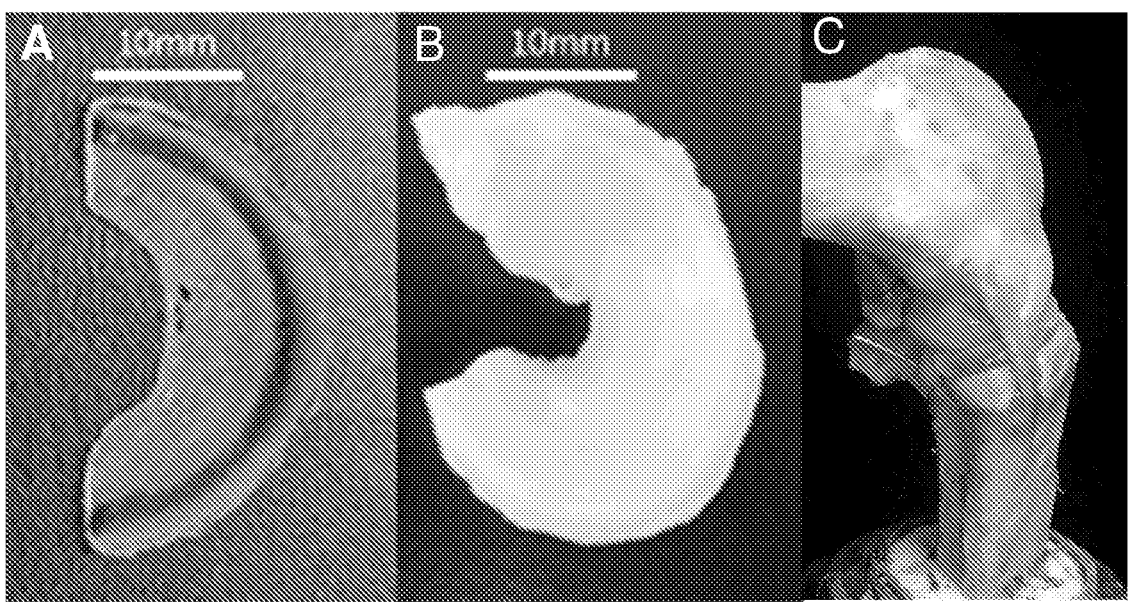

To manufacture a prototype 3D meniscal implant, a simple mold was prepared using a 3D printer with polyjet technology (Objet30 Pro, Stratasys Ltd., United States). This technology jets and UV-cures tiny droplets of liquid polymer. Simplifying the native meniscus geometry and accounting for post-processing swelling, a mold was created using simulated polypropylene material (Durus RGD430, Stratasys Ltd.) (FIG. 57A). The mold was packed with a blend containing 46 mol % SOS triblock copolymer, melt pressed at 75° C. under 10 pounds of pressure for 30 minutes, cooled, then swollen in DI water overnight. At 46% SOS triblock copolymer, the swollen composite was about three times the linear dimension of the dry polymer with a size and shape similar to the sheep meniscus (FIGS. 57B&C).

Methacrylate modified non-absorbable polyamide sutures (size 3-0, MAXON; Syneture Co., Ltd.) were threaded through the copolymer. These fibers extended beyond the gel allowing use as anchors for the construct when threaded through bone tunnels in the tibial plateau. The integration of tie lines formed from hyaluronic acid interpenetrating network was accomplished using hyaluronic acid (about 700 kDa) previously modified with both a fluorescent tag (5-amino fluorescein) and pendent methacrylate functionality (see Example 24). Using a water-soluble free radical initiator (Irgacure™ 5929) the tie lines were isolated to specific locations. These data demonstrate that a biphasic polymer composite can be manufactured and the fluid content, material properties and recovery controlled. A 3D anatomically shaped meniscus can also be manufactured, reinforced with fibers, and integrated with an interpenetrating network of hyaluronic acid.

Imaging software has also been used to create a more accurate meniscal construct. 3DSlicer converted microtomographic (micro computer tomographic, μCT) DICOM images to a 3D-rendered surface (FIGS. 58A&B). A mesh of that surface was prepared in Meshlab, and using the built-in quadratic edge collapse decimation, the number of faces was reduced. A Laplacian smoothing function with three smoothing steps, one-dimensional boundary smoothing, and cotangent weighting removed small artifacts. Internal structures and overhangs were adjusted by hand using MeshMixer and Blender, respectively. FIGS. 59A-F contains some example images revealing differences in the solid model depending on the number of faces and smoothing performed. SolidWorks (Dassault Systems, SolidWorks Corporation, USA) created a parting surface and a negative mold of the original meniscus µCT model. This mold and the meniscal shape itself were printed using acrylonitrile butadiene styrene material (ABS).

The parameter-dependent process of µCT image transformation to a 3D rendered surface are being explored. The 3D model should accurately reflect the tissue imaged at a level of detail compatible with the 3D printing process. This procedure requires image reduction, smoothing, and elimination of overhangs. A set of image reduction guidelines are being developed to efficient convert to 3D printer-optimized surface renderings. The criteria for optimization will be informed by an analysis of the minimum level of detail to accurately capture the meniscus function, balanced against the maximal resolution capabilities of the 3D printing process. For a clean release from the parting surface of the negative mold, the surface detail should be excessively smoothed and reduced.

Alternatively, directly printing the construct from a filament of SOS copolymer would result in a construct having a more similar structure and appearance to its parent image. A Monoprice maker select 3D printer (V2, Monoprice, Inc.) was used, featuring a headed bed and filament with a diameter of 1.75 mm. The resolution of the printer was 100 microns and can print at up to 260° C., making it possible to print with a wide variety of materials, including acrylonitrile butadiene styrene (ABS), polylactic acid (PLA), ColorFabb™ XT Copolyester (Eastman Amphora®), polyethylene terephthalate (PET), thermoplastic polyurethane (TPU), thermoplastic copolyester (TPC), fluorenone polyester (FPE), polyvinyl alcohol (PVA), high impact polystyrene (HIPS), and combinations thereof.

A printable filament from the SO-SOS polymer source is prepared using a microextruder. Extrusion conditions (extruder rate, temperature) that produce uniform filaments of 1.75 mm are determined. Starting conditions are extrapolated from the polymer rheological properties. Once filament has been created, the appropriate extruder temperature, bed temperature, and extruder rate are determined for high quality printing. Four extruder temps (140° C., 160° C., 180° C., and 200° C.), three bed temperatures (50° C., 60° C., and 70° C.), and three extruder rates (30 mm/s, 60 mm/s, and 90 mm/s) provide a total of 36 combinations of conditions. These levels were identified as potential ideal temperatures and rates based on similar materials and the known melting temperature of the SOS copolymer. Three tensile dog bone samples are printed at each condition and tested for max stress, elongation at break, and Young's modulus testing protocol and dog bone dimensions following ASTM standard D412-15a (incorporated herein by reference). Layer height, infill, infill pattern are maintained at 0.20 mm, 70%, and linear for all testing conditions. The condition that results in the greatest Young's modulus and max stress with the least elongation at break will be the chosen conditions.

Example 26—In-Vivo Study of Hydrogel Soft Tissue Mimetics in Surgical Models

Direct 3D printing of the hydrogel construct is viable when the printed construct performs as well or better than the molded construct. To test this, load distribution properties of the 3D printed construct will be compared to both the molded construct as well as native tissue. FIG. 60 shows three-dimensional prints of the negative mold and the meniscus shape printed using a surface mesh reduced to 300 faces with smoothing. Print material used is acrylonitrile butadiene styrene material (ABS). FIG. 60A shows the meniscus shape in one half of the negative mold. FIG. 60B shows the meniscus shape removed from the negative mold.

Pressure film (Tekscan, Boston, Mass.) has been used to create a dynamic pressure map of the contact forces in the tibiofemoral joint (FIG. 61). FIG. 61A ovine knee with excess musculature removed. FIG. 61B depicts a joint more completely dissected showing a Tekscan™ sensor (model 6900) and 3D hydrogel construct. The inset image of FIG. 61B is an example of the pressure distribution data accessible through use of the Tekscan sensors (data from model 4010 shown).

A servohydraulic test system (Bionic Model 370.02 MTS Corp., Eden Prairie, Minn.) and Tekscan™ software test the effectiveness of the two identical, but differently created, constructs in distributing load across the joint. Using five ovine knees, the Tekscan™ film are placed on the tibial plateau under the native menisci, and Tekscan™ software process feedback from the pressure film. The femur is fixed to the actuator while the tibial plateau are mounted in a custom three degree of rotation fixture to allow the joint to settle in a natural position. The joint is loaded to thrice bodyweight at a flexion angle of 0° followed by 90°. The intact meniscus is tested first and used as a benchmark. Next, the medial meniscus is replaced first with the molded construct followed by the 3D printed construct. Substantially identical procedures are used for implantation. The peak pressure, mean pressure, peak pressure location and contact area between the three conditions are compared at the two degrees of flexion (0° and 90°) using a repeated measures analysis of variance (ANOVA).

To be commercially competitive, the hydrogel construct should be easily designed patient-to-patient and implantable using current surgical devices and practices. Construct can be creating using µCT imaging or magnetic resonance imaging (MRI). The image segmentation software Amira (Visage, Berlin, Germany) can be used with MRI slices to recreate the geometry of the menisci. 3D-printed constructs can be produced from the data files created from these reconstructed menisci.

Figures 62A, 62B:
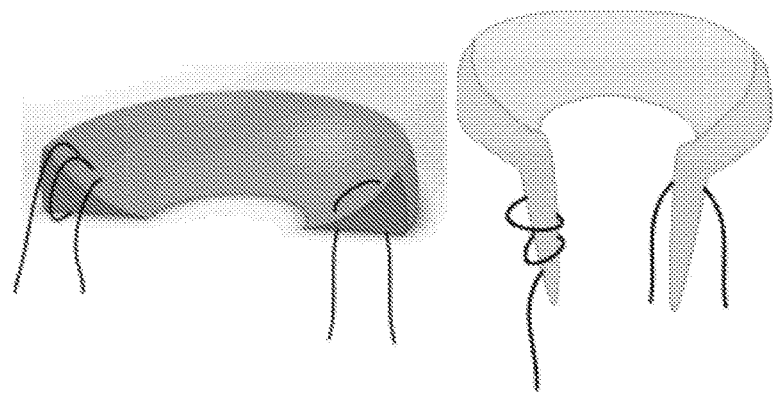
FIGS. 62A&B. Examples of suture-based attachment methods.

Strategies for meniscal allograft transplants fall into two main categories: those that use bone plugs and those that rely primarily on sutures to affix the allograft to surrounding soft tissues. The construct can be implanted with sutures through bone tunnels with endotabs for fixing the sutures as they exit the bone tunnels on the anterior aspect of the tibia. FIGS. 62A&B illustrates this approach.

Figures 63A, 63B, 63C:
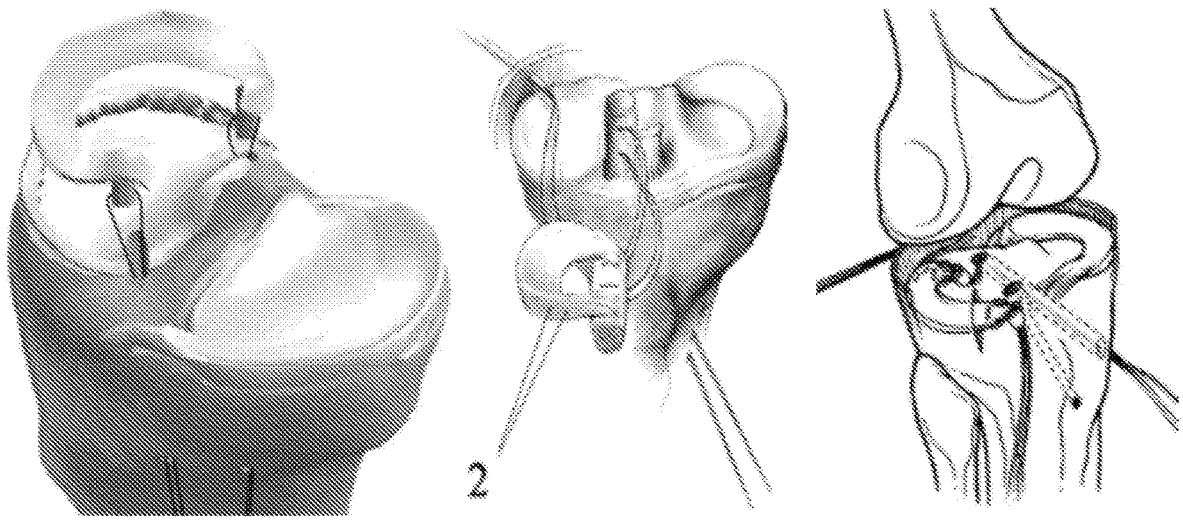
FIGS. 63A-C. Examples of allograft attachment methods using bone plugs for reinforced attachment.
Figures 64A, 64B:
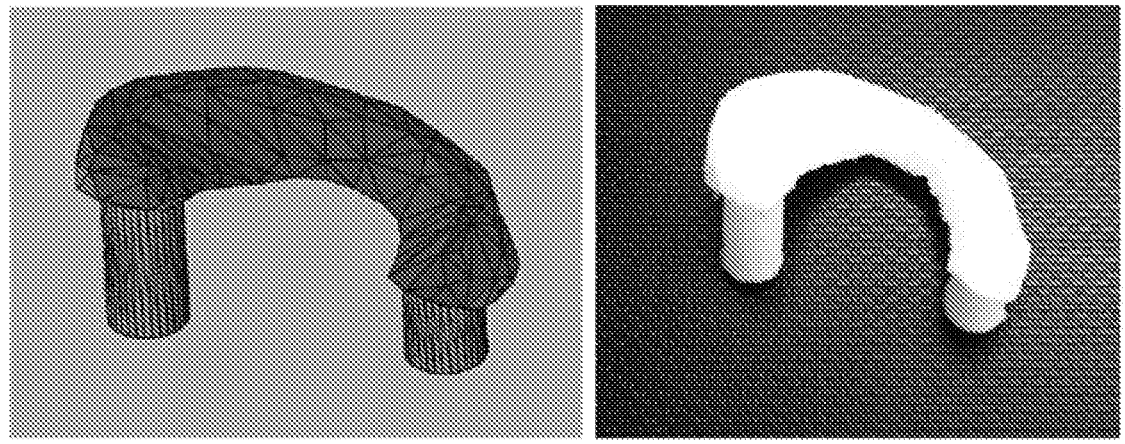
FIG. 64A. Solidworks™ model of a microCT image derived meniscus with extended tabs.
FIG. 64B shows an actual printed 3D construct using polylactic acid at an extruder temp of 210° C. and a bed temperature of 70° C.
Figure 65:
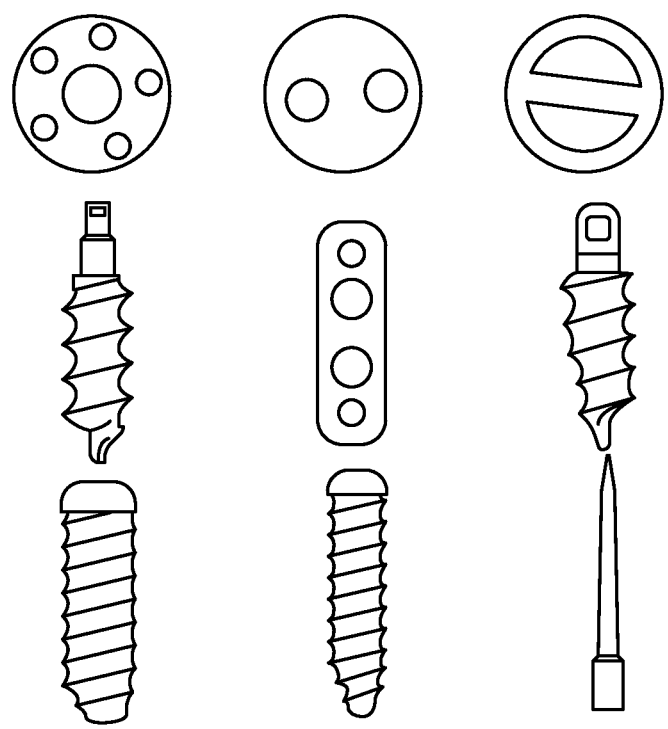
FIG. 65. Examples of surgical screws. The interference screws shown in the lower left of FIG. 65 help secure the extended tabs of the meniscal construct.

When sutures alone are used as the attachment mechanism, they have led to meniscal extrusion and lower fixation strength compared to allografts with bone block. FIG. 63 shows a comparison of the allograft attachment methods, explicitly illustrating the use of bone blocks. Implementing ancillary tabs (plugs) made from the hydrogels described herein or even using a transition from hydrogel into a stiffer polymer through post-printing introduction of a stiffening agent (to the tab) may allow a construct to be more mimetic of an allograft with bone plugs. These tabs can be created in 3D modeling software and printed using the same techniques previously outlined. An example is shown in FIG. 64.

Adding tabs mechanically reduces the stress concentrations in fixation methods, and clinically provide a more stable fixation. Although an allograft with bone eventually integrates into the surrounding bone, additional steps are often taken to fix the implant within the joint. A common surgical technique used in these cases is an interference screw to create a tight fit between the implanted bone and the bone tunnel created for the transplant. A similar technique could be done for fixing 3D printed construct with tabs. FIG.

65 shows several examples of commonly used surgical screws, including interference screws (two in lower left part of the figure).

These two methods of attachment, sutures versus tabbed ends, are tested in situ and evaluated for pullout strength similar to previous studies. Five implants of each type will be performed on the posterior attachment of ovine limbs and specimens will be subjected to both cyclic and pull-to-failure testing. Displacement will be assessed for all specimens following 100, 500, and 1000 cycles. Once 1000 cycles have been completed, samples will be pulled to failure and evaluated for maximum load to failure and stiffness.

It should be appreciated by those of skill in the art that the techniques disclosed in the examples represent techniques discovered by the inventors to function well in the practice of the disclosure. Those of skill in the art should, however, in light of the present disclosure, appreciate that many changes can be made in the specific embodiments that are disclosed and still obtain a like or similar result without departing from the spirit and scope of the disclosure, therefore all matter set forth is to be interpreted as illustrative and not in a limiting sense.

What is claimed is:

1. A soft tissue mimetic formed from a block copolymer hydrogel, the hydrogel comprising:
   a glass formed from a dry blend comprising polystyrene-poly(ethylene oxide) diblock copolymer (SO) and polystyrene-poly(ethylene oxide)-polystyrene triblock copolymer (SOS) in a molar ratio from between 95:5 and 1:99 SO/SOS;
   a liquid medium at a concentration between about 32:1 and about 2:1 liquid medium/SO-SOS by weight, the liquid medium comprising a buffer; and
   one or more reinforcements, wherein the one or more reinforcements are polyamide fibers, methacrylate-functionalized polyamide fibers, acrylate-functionalized polyamide fibers, photo-crosslinked tie lines, or combinations thereof;
   the soft tissue mimetic having a fatigue resistance to at least 500,000 compression cycles, wherein the compression cycles operate with at least 12% compression at a frequency of about 1 Hz, and the compression cycles operate with at least 50% compression at least every eleventh cycle and wherein the fatigue resistance is characterized by a modulus recoverable to at least 80% of its value before the compression cycles were run.

2. The soft tissue mimetic of claim 1, wherein the molar ratio is between about 80:20 and about 20:80 SO/SOS.

3. The soft tissue mimetic of claim 1, wherein the liquid medium is at a concentration between about 16:1 and about 4:1 liquid medium/SO-SOS by weight.

4. The soft tissue mimetic of claim 1, wherein the reinforcements are located circumferentially and radially within the soft tissue mimetic.

5. The soft tissue mimetic of claim 1, further comprising one or more suture tabs adapted for implanting the soft tissue mimetic into a patient.

6. The soft tissue mimetic of claim 1, wherein the fatigue resistance is characterized by a modulus recoverable to at least 92% of its value before the compression cycles were run.

7. The soft tissue mimetic of claim 1, having an instantaneous modulus between about 0.5 MPa and about 3 MPa.

8. The soft tissue mimetic of claim 1, having an equilibrium compressive modulus between about 0.05 and about 0.8 MPa.

9. The soft tissue mimetic of claim 1, having a tensile modulus between about 0.5 MPa and about 140 MPa.

10. A knee meniscus replacement, comprising a lunate body formed from a block copolymer hydrogel and reinforcements circumferentially and radially disposed within the lunate body,
    wherein the block copolymer hydrogel comprises a glass formed from a dry blend comprising polystyrene-poly(ethylene oxide) diblock copolymer (SO) and polystyrene-poly(ethylene oxide)-polystyrene triblock copolymer (SOS) in a molar ratio from between 95:5 and 1:99 SO/SOS; and a liquid medium at a concentration between about 32:1 and about 2:1 liquid medium/SO-SOS by weight,
    wherein the reinforcements are polyamide fibers, methacrylate-functionalized polyamide fibers, acrylate-functionalized polyamide fibers, photo-crosslinked tie lines, or combinations thereof, and
    wherein the knee meniscus replacement has a fatigue resistance to at least 500,000 compression cycles, wherein the compression cycles operate with at least 12% compression at a frequency of about 1 Hz, and the compression cycles operate with at least 50% compression at least every eleventh cycle and wherein the fatigue resistance is characterized by a modulus recoverable to at least 80% of its value before the compression cycles were run.

11. The knee meniscus replacement of claim 10, having an instantaneous modulus between about 0.5 MPa and about 3 MPa.

12. The knee meniscus replacement of claim 10, having an equilibrium compressive modulus between about 0.05 and about 0.8 MPa.

13. The knee meniscus replacement of claim 10, having a tensile modulus between about 0.5 MPa and about 140 MPa.

14. A method for preparing a soft tissue mimetic, the method comprising:
    printing a pair of negative molds having an interior volume defined by a three-dimensional model of a native soft tissue;
    injecting into the interior volume a dry blend comprising polystyrene-poly(ethylene oxide) diblock copolymer (SO) and polystyrene-poly(ethylene oxide)-polystyrene triblock copolymer (SOS) in a molar ratio from between 95:5 and 1:99 SO/SOS;
    heating the SO-SOS dry blend to form an SO-SOS melt;
    allowing the SO-SOS melt to attain ambient temperature to form an SO-SOS glass; and
    contacting the SO-SOS glass with a liquid medium to form a block copolymer hydrogel,
    the soft tissue mimetic having a fatigue resistance to at least 500,000 compression cycles, wherein the compression cycles operate with at least 12% compression at a frequency of about 1 Hz, and the compression cycles operate with at least 50% compression at least every eleventh cycle and wherein the fatigue resistance is characterized by a modulus recoverable to at least 80% of its value before the compression cycles were run.

15. The method of claim 14, wherein the molar ratio is between about 80:20 and about 20:80 SO/SOS.

16. The method of claim 14, wherein the SO-SOS dry blend is heated to a temperature between about 100° C. and about 180° C., under a pressure between about 50 psig and about 800 psig, and for between about 5 minutes and about 50 minutes.

17. The method of claim 14, having a liquid medium concentration between about 16:1 and about 4:1 liquid medium/SO-SOS by weight.

18. The method of claim 14, wherein the fatigue resistance is characterized by a modulus recoverable to at least 92% of its value before the compression cycles were run.

19. The method of claim 14, further comprising placing reinforcement fibers in the negative mold before injecting the SO-SOS dry blend.

20. The method of claim 19, wherein the reinforcement fibers are polyamide fibers, methacrylate-functionalized polyamide fibers, acrylate-functionalized polyamide fibers, or combinations thereof.

21. The method of claim 20, further comprising photo-crosslinking a portion of the block copolymer hydrogel to form a reinforcement tie line.

22. The method of claim 14, wherein the soft tissue mimetic is a knee meniscus replacement.

23. The method of claim 14, further comprising hydrogenating the polystyrene.

24. The soft tissue mimetic of claim 1, wherein chain ends of the SO are functionalized with azide and alkyne groups.

25. The method of claim 14, wherein chain ends of the SO are functionalized with azide and alkyne groups, and wherein the method further comprises coupling the SO chain ends in the liquid medium to modify the SO/SOS molar ratio.

26. The soft tissue mimetic of claim 1, wherein the buffer is phosphate-buffered saline (PBS), Ringer's solution, or combinations thereof.

27. The soft tissue mimetic of claim 26, wherein the buffer is phosphate-buffered saline (PBS).

28. The knee meniscus replacement of claim 10, wherein the liquid medium comprises a buffer.

29. The knee meniscus replacement of claim 28, wherein the buffer is phosphate-buffered saline (PBS), Ringer's solution, or combinations thereof.

30. The knee meniscus replacement of claim 29, wherein the buffer is phosphate-buffered saline (PBS).

31. The method of claim 14, wherein the liquid medium comprises a buffer.

32. The method of claim 31, wherein the buffer is phosphate-buffered saline (PBS), Ringer's solution, or combinations thereof.

33. The method of claim 32, wherein the buffer is phosphate-buffered saline (PBS).

* * * * *